United States Patent
Li et al.

(10) Patent No.: US 9,594,085 B2
(45) Date of Patent: Mar. 14, 2017

(54) INTEGRATED QUANTIFICATION METHOD FOR PROTEIN MEASUREMENTS IN CLINICAL PROTEOMICS

(71) Applicant: Integrated Diagnostics, Inc., Seattle, WA (US)

(72) Inventors: Xiao-Jun Li, Bellevue, WA (US); Stephen W. Hunsucker, Seattle, WA (US); Clive Hayward, Seattle, WA (US); Paul Edward Kearney, Montreal (CA); Lik Wee Lee, Seattle, WA (US)

(73) Assignee: INTEGRATED DIAGNOSTICS, INC., Seattle, WA (US)

( * ) Notice: Subject to any disclaimer, the term of this patent is extended or adjusted under 35 U.S.C. 154(b) by 25 days.

(21) Appl. No.: 14/612,959

(22) Filed: Feb. 3, 2015

(65) Prior Publication Data

US 2015/0219666 A1 Aug. 6, 2015

Related U.S. Application Data

(60) Provisional application No. 61/935,061, filed on Feb. 3, 2014.

(51) Int. Cl.
| | |
|---|---|
| G01N 33/68 | (2006.01) |
| G01N 33/574 | (2006.01) |
| G06F 19/20 | (2011.01) |
| G06F 19/24 | (2011.01) |

(52) U.S. Cl.
CPC ... *G01N 33/6848* (2013.01); *G01N 33/57423* (2013.01); *G06F 19/20* (2013.01); *G06F 19/24* (2013.01); *G01N 2458/15* (2013.01); *G01N 2570/00* (2013.01); *G01N 2800/12* (2013.01)

(58) Field of Classification Search
None
See application file for complete search history.

(56) References Cited

U.S. PATENT DOCUMENTS

| | | |
|---|---|---|
| 7,183,188 B2 | 2/2007 | Krönke et al. |
| 2007/0099251 A1 | 5/2007 | Zhang et al. |
| 2007/0202539 A1 | 8/2007 | Aebersold et al. |
| 2007/0269895 A1 | 11/2007 | Aebersold et al. |
| 2008/0188479 A1 | 8/2008 | O'Connor et al. |
| 2010/0279382 A1 | 11/2010 | Aebersold et al. |
| 2012/0270254 A1 | 10/2012 | Liao et al. |
| 2013/0217057 A1 | 8/2013 | Kearney et al. |
| 2013/0230877 A1 | 9/2013 | Kearney et al. |

FOREIGN PATENT DOCUMENTS

| | | |
|---|---|---|
| WO | WO 03/015613 A2 | 2/2003 |
| WO | WO 2012/166722 A1 | 12/2012 |
| WO | WO 2013/096845 A2 | 6/2013 |
| WO | WO 2013/096862 A2 | 6/2013 |

OTHER PUBLICATIONS

Kitteringham et al. J. Chromatography 2009 vol. 877 p. 1229-1239.*
Lange et al. Molecular Systems Biology 4:222, p. 1-14.*
Lebert et al. "Production and Use of Stable Isotope-Labeled Proteins for Absolute Quantitative Proteomics," *Methods in Molecular Biology*, 2011, vol. 753, Ch 7, pp. 93-115.
Kim et al. "Up-Regulation of Peroxiredoxin 1 in Lung Cancer and Its Implication as a Prognostic and Therapeutic Target," *Clinical Cancer Research*, vol. 14, No. 8, Jan. 1, 2008, pp. 2326-2333.
Li, XJ. et al., "A blood-based proteomic classifier for the molecular characterization of pulmonary nodules." *Sci. Trans. Med.* 2013, 5:207ra142.
Vachani et al., "Validation of a Multi-Protein Plasma Classifier to Identify Benign Lung Nodules," *J. of Thoracic. Oncol.* vol. 10, No. 4, Apr. 2015, pp. 629-637.
Chang, CY et al, "Targeted protein quantification using spare reference labeling," *Nat. Methods* 2014, 11:301-304.
International Search Report and Written Opinion, mailed Jun. 3, 2015, for International Application No. PCT/US2015/014257.
International Search Report and Written Opinion, mailed Feb. 19, 2015, for International Application No. PCT/US2014/056637.
Abbatiello, S.E. et al. "Design, Implementation and Multisite Evaluation of a System Suitability Protocol for the Quantitative Assessment of Instrument Performance in Liquid Chromatography-Multiple Reaction Monitoring-MS (LC-MRM-MS)", *Molecular & cellular proteomics: MCP* 12, 2623-2639 (2013).
Addona, T.A. et al. "Multi-site assessment of the precision and reproducibility of multiple reaction monitoring-based measurements of proteins in plasma", *Nature biotechnology* 27, 633-641 (2009).
Addona, T.A. et al. "A pipeline that integrates the discovery and verification of plasma protein biomarkers reveals candidate markers for cardiovascular disease", *Nature biotechnology* 29, 635-643 (2011).
Anderson, L. & Hunter, C.L. "Quantitative mass spectrometric multiple reaction monitoring assays for major plasma proteins", *Molecular & cellular proteomics: MCP* 5, 573-588 (2006).

(Continued)

*Primary Examiner* — Jacob Cheu
(74) *Attorney, Agent, or Firm* — Cooley LLP; Ivor Elrifi; Matthew Pavao

(57) ABSTRACT

Methods are provided for determining the expression level of target proteins in a subject. A plurality of respective peptide transitions are generated from a plurality of proteins obtained from a biological sample from the subject, wherein the plurality of proteins comprises both target and normalizing proteins. A mass spectroscopy (MS) signal intensity is measured from the plurality of respective peptide transitions and a plurality of corresponding stable isotope-labeled internal standard (SIS) peptide transitions. For each of the plurality of proteins, a response ratio is calculated between the MS signal intensity of the respective peptide transition and the corresponding SIS peptide transition. The response ratio for each target protein is normalized by a sample-dependent normalization factor calculated from the response ratio for each normalizing protein, wherein the normalized response ratios provide a determination of the expression level of the target proteins.

22 Claims, 8 Drawing Sheets

(56) References Cited

OTHER PUBLICATIONS

Anderson, N.L. & Anderson, N.G. "The human plasma proteome: history, character, and diagnostic prospects", *Molecular & cellular proteomics: MCP* 1, 845-867 (2002).
Barr, J. R. et al. "Isotope dilution—mass spectrometric quantification of specific proteins: model application with apolipoprotein A-1", *Clinical chemistry* 42, 1676-1682 (1996).
Boedigheimer, M.J. et al. "Sources of variation in baseline gene expression levels from toxicogenomics study control animals across multiple laboratories", *BMC genomics* 9, 285 (2008).
Chen, C. et al. "Removing batch effects in analysis of expression microarray data: an evaluation of six batch adjustment methods", *PloS one* 6, e17238 (2011).
Deng, M.C. et al. "Noninvasive discrimination of rejection in cardiac allograft recipients using gene expression profiling", *American journal of transplantation: official journal of the American Society of Transplantation and the American Society of Transplant Surgeons* 6, 150-160 (2006).
Farrah, T. et al. "A high-confidence human plasma proteome reference set with estimated concentrations in Peptide Atlas", *Molecular & cellular proteomics: MCP* 10, M110 006353 (2011).
Gerber, S.A., Rush, J., Stemman, O., Kirschner, M.W. & Gygi, S.P. "Absolute quantification of proteins and phosphoproteins from cell lysates by tandem MS", *Proceedings of the National Academy of Sciences of the United States of America* 100, 6940-6945 (2003).
Griffin, N.M. et al. "Label-free, normalized quantification of complex mass spectrometry data for proteomic analysis", *Nature biotechnology* 28, 83-89 (2010).
Hanke, S., Besir, H., Oesterhelt, D. & Mann, M. "Absolute SILAC for accurate quantitation of proteins in complex mixtures down to the attomole level", *Journal of proteome research* 7, 1118-1130 (2008).
Huttenhain, R., Malmstrom, J., Picotti, P. & Aebersold, R. "Perspectives of targeted mass spectrometry for protein biomarker verification", *Current opinion in chemical biology* 13, 518-525 (2009).
Huttenhain, R. et al. "Reproducible quantification of cancer-associated proteins in body fluids using targeted proteomics" *Sci Trans. Med* 4, 142ra94 (2012).
Kuhn, E. et al. "Interlaboratory evaluation of automated, multiplexed peptide immunoaffinity enrichment coupled to multiple reaction monitoring mass spectrometry for quantifying proteins in plasma", *Molecular & cellular proteomics: MCP* 11, M111 013854 (2012).
Kuzyk, M.A. et al. Multiple reaction monitoring-based, multiplexed, absolute quantitation of 45 proteins in human plasma, *Molecular & cellular proteomics: MCP* 8, 1860-1877 (2009).
Li, XJ et al. "An integrated quantification method to increase the precision, robustness, and resolution of protein measurement in human plasma samples", Integrated Quantification for Clinical Proteomics, 2015, vol. 12, No. 3, 59 pages.
Ludwig, C., Claassen, M., Schmidt, A. & Aebersold, R. "Estimation of absolute protein quantities of unlabeled samples by selected reaction monitoring mass spectrometry", *Molecular & cellular proteomics: MCP* 11, M111 013987 (2012).
Qian, W.J. et al "Enhanced detection of low abundance human plasma proteins using a tandem IgY12-SuperMix immunoaffinity separation strategy", *Molecular & cellular proteomics: MCP* 7, 1963-1973 (2008).
Paik, S. et al. "A multigene assay to predict recurrence of tamoxifentreated, node-negative breast cancer", *The New England journal of medicine* 351, 2817-2826 (2004).
Picard, G. et al. "PSAQ standards for accurate MS-based quantification of proteins: from the concept to biomedical applications", *Journal of mass spectrometry: JMS* 47, 1353-1363 (2012).
Picotti, P. et al. "High-throughput generation of selected reactionmonitoring assays for proteins and proteomes", *Nature methods* 7, 43-46 (2010).
Reimer, J. et al. "Effect of cyclization of N-terminal glutamine and carbamidomethyl-cysteine (residues) on the chromatographic behavior of peptides in reversed-phase chromatography", *Journal of chromatography, A* 1218, 5101-5107 (2011).
Rivers, J., Simpson, D.M., Robertson, D.H., Gaskell, S.J. & Beynon, R.J. "Absolute multiplexed quantitative analysis of protein expression during muscle development using QconCAT", *Molecular & cellular proteomics: MCP* 6, 1416-1427 (2007).
Shi, T. et al. "Advancing the sensitivity of selected reaction monitoringbased targeted quantitative proteomics", *Proteomics* 12, 1074-1092 (2012).
Singh, S., Springer, M., Steen, J., Kirschner, M.W. & Steen, "FLEXIQuant: a novel tool for the absolute quantification of proteins, and the simultaneous identification and quantification of potentially modified peptides", *Journal of proteome research* 8, 2201-2210 (2009).
Whiteaker, J.R. et al. "A targeted proteomics-based pipeline for verification of biomarkers in plasma", *Nature biotechnology* 29, 625-634 (2011).
Zeiler, M., Straube, W.L., Lundberg, E., Uhlen, M. & Mann, M. "A Protein Epitope Signature Tag (PrEST) library allows Silac-based absolute quantification and multiplexed determination of protein copy numbers in cell lines", *Molecular & cellular proteomics: MCP* 11, 0111 009613.
Zhang, H. et al. "Methods for peptide and protein quantitation by liquid chromatography—multiple reaction monitoring mass spectrometry", *Molecular & cellular proteomics: MCP* 10, M110006593 (2011).

\* cited by examiner

FIG. 1

INTEGRATED QUANTIFICATION METHOD FOR PROTEIN MEASUREMENTS IN CLINICAL PROTEOMICS

RELATED APPLICATIONS

This application claims the benefit of, and priority to, U.S. Provisional Application No. 61/935,061 filed Feb. 3, 2014, the content of which is incorporated herein by reference in its entirety.

INCORPORATION-BY-REFERENCE OF SEQUENCE LISTING

The contents of the text file named "IDIA_012_001US_ST25.txt", which was created on Feb. 20, 2015 and is 211 KB in size, are hereby incorporated by reference in their entireties.

BACKGROUND

Multiple reaction monitoring (MRM), also known as selected reaction monitoring (SRM) mass spectrometry (MS), allows for fast and reproducible measurement of tens to hundreds of proteins in complex biological samples such as bio-fluids, tissues, and cultured cells. There is tremendous interest in applying the technology to develop blood-based clinical tests for the diagnosis, prognosis or treatment stratification of various diseases. Due to the high complexity of the human blood proteome, proteomic analysis of blood samples typically consists of multiple experimental steps and is prone to variation (FIG. 1A). In addition, changes in laboratory conditions (e.g., operators, instruments, reagents) are expected during routine laboratory operations in clinical testing. Therefore, controlling analytical variability to satisfy rigorous quality control requirements for blood-based clinical testing using MRM-MS platforms has been challenging.

The principle of stable isotope labeling (SIL) is currently used in MS-based quantitative proteomics to control experimental variability. Protein abundance is measured by comparing MS signal intensities of endogenous peptides with those of their corresponding stable isotope-labeled internal standard (SIS) peptides. Three SIL approaches are potentially suitable for clinical testing (FIG. 1B). The first approach utilizes SIS peptides for protein quantification (SISQuan) and is the simplest one for implementation. SIS peptides are synthesized, optimized for MS analysis and spiked into samples before or after protein digestion to control variation in post-digestion procedures. However, variation occurring before or during digestion is not controlled. The second approach spikes full-length SIS proteins into samples before any analytical procedure takes place. While this approach offers the best control of analytical variability, it is applicable only to soluble proteins. Quality control of the production, the storage, etc., of SIS proteins as standards is challenging for routine laboratory operations. The third approach spikes either artificial or truncated SIS proteins into samples before protein digestion. It controls most variation in protein digestion and variation in subsequent procedures. However, it cannot control variation occurring before digestion and faces similar implementation challenges as the second approach. None of the above SIL approaches can control pre-analytical variability associated with sample collection and handling.

Thus, there is a need for a simple and robust method that provides sufficient control of pre-analytical and analytical variability for routine clinical testing on MS-based proteomics platforms. The present invention addresses that need.

SUMMARY

In one embodiment, the present invention provides a method for determining the expression level of target proteins in a subject. A plurality of respective peptide transitions are generated from a plurality of proteins obtained from a biological sample from the subject, wherein the plurality of proteins comprises both target and normalizing proteins. A mass spectroscopy (MS) signal intensity is measured from the plurality of respective peptide transitions and a plurality of corresponding stable isotope-labeled internal standard (SIS) peptide transitions. For each of the plurality of proteins, a response ratio is calculated between the MS signal intensity of the respective peptide transition and the corresponding SIS peptide transition. The response ratio for each target protein is normalized by a sample-dependent normalization factor calculated from the response ratio for each normalizing protein, wherein the normalized response ratios provide a determination of the expression level of the target proteins.

According to another embodiment, the determination of the expression level of the target proteins provides a diagnosis of lung disease for the subject.

According to yet another embodiment, the normalizing proteins are selected based on their ability to reduce intensity drift (D) of each of the plurality of respective peptide transitions, wherein intensity drift evaluates the deviation in abundance of each peptide transition from the overall median abundance of each peptide transition.

According to one embodiment, the normalizing proteins are selected based on their ability to reduce the median technical coefficient of variation (CV) of the plurality of proteins.

According to another embodiment, the plurality of proteins comprise at least two normalizing proteins selected from the group consisting of PEDF (Pigment epithelium-derived factor), MASP1 (Mannan-binding lectin serine protease 1), GELS (Gelsolin), LUM (Lumican), C163A (Scavenger receptor cysteine-rich type 1 protein M130), and PTPRJ (Receptor-type tyrosine-protein phosphatase eta).

According to yet another embodiment, the plurality of proteins comprise six normalizing proteins including PEDF_HUMAN, MASP1_HUMAN, GELS_HUMAN, LUM_HUMAN, C163A_HUMAN, and PTPRJ_HUMAN.

According to one embodiment, the plurality of respective peptide transitions comprise LQSLFDSPDFSK (SEQ ID NO: 25) (692.34, 593.30), TGVITSPDFPNPYPK (SEQ ID NO: 26) (816.92, 258.10), TASDFITK (SEQ ID NO: 27) (441.73, 710.40), SLEDLQLTHNK (SEQ ID NO: 28) (433.23, 499.30), INPASLDK (SEQ ID NO: 29)(429.24, 630.30), and VITEPIPVSDLR (SEQ ID NO: 30)(669.89, 896.50).

According to another embodiment, the target proteins comprise at least five of KIT_HUMAN, FRIL_HUMAN, COIA1_HUMAN, PRDX1_HUMAN, TENX_HUMAN, ENPL_HUMAN, GRP78_HUMAN, BGH3_HUMAN, ALDOA_HUMAN, GGH_HUMAN, CD14_HUMAN, LG3BP_HUMAN, TSP1_HUMAN, IBP3_HUMAN, TETN_HUMAN, and ISLR_HUMAN.

According to yet another embodiment, the target proteins comprise ALDOA_HUMAN, FRIL_HUMAN, COIA1_HUMAN, LG3BP_HUMAN, and TSP1_HUMAN.

According to yet another embodiment, the target proteins comprise ALDOA_HUMAN, FRIL_HUMAN, KIT_HUMAN, GGH_HUMAN, and TSP1_HUMAN.

According to one embodiment, the target proteins comprise KIT_HUMAN, FRIL_HUMAN, COIA1_HUMAN, PRDX_HUMAN, TENX_HUMAN, ENPL_HUMAN, TENX_HUMAN, ENPL_HUMAN, GRP78_HUMAN, BGH3_HUMAN, ALDOA_HUMAN, GGH_HUMAN, CD14_HUMAN, LG3BP_HUMAN, IBP3_HUMAN, TETN_HUMAN, and ISLR_HUMAN.

According to another embodiment, the biological sample is selected from the group consisting of tissue, blood, plasma, serum, whole blood, urine, saliva, genital secretion, cerebrospinal fluid, sweat, excreta, or bronchoalveolar lavage.

According to yet another embodiment, the plurality of proteins are obtained by immunoaffinity depletion.

According to one embodiment, the measuring step is performed by selected reaction monitoring mass spectrometry (SRM-MS).

According to another embodiment, the plurality of respective peptide transitions are generated by enzymatically digesting the plurality of proteins.

The methods of the current invention may include generation of the respective peptide transitions by fragmentation of the plurality of proteins by trypsin digestion. The methods of the current invention can include various manners to assess the expression of the plurality of proteins, including mass spectrometry (MS), liquid chromatography-selected reaction monitoring/mass spectrometry (LC-SRM-MS), reverse transcriptase-polymerase chain reaction (RT-PCR), microarray, serial analysis of gene expression (SAGE), gene expression analysis by massively parallel signature sequencing (MPSS), immunoassays, immunohistochemistry (IHC), transcriptomics, or proteomics.

According to yet another embodiment, the response ratio (R) is defined as:

$$R_{p,s}=A_{p,s}/\hat{A}_{p,s}$$

where $A_{p,s}$ is the peak area of the signal intensity of peptide transition p in the biological sample s, and $\hat{A}_{p,s}$ is the peak area of the signal intensity the corresponding SIS peptide transition.

According to one embodiment, the sample-dependent normalization factor (S) is defined as:

$$S_s^I = \mathrm{median}\left(\frac{R_{1,s}}{\check{R}_1}, \frac{R_{2,s}}{\check{R}_2}, \ldots, \frac{R_{N,s}}{\check{R}_N}\right)$$

where $S_s^I$ is the sample-dependent normalization factor calculated from the response ratios (R) of the N peptide transitions from normalizing proteins in the biological sample s, where $R_{n,s}$ is response ratio of peptide transitions from normalizing proteins n in the sample and $\check{R}_n$ is a scaling constant for the peptide normalizer that ensures values of $\{R_{n,s}/\check{R}_n\}$ among all peptide transitions from normalizing proteins to be same on average.

According to another embodiment, the normalized response ratio (Ř) is defined as:

$$\check{R}_{p,s}=R_{p,s}/S_s^I,$$

where p is peptide transition, s is the biological sample, $R_{p,s}$ is the response ratio of peptide p in biological sample s, and $S_s^I$ is the sample-dependent normalization factor.

According to yet another embodiment, the intensity drift (D) is defined by:

$$D_{p,s}=(I_{p,s}-\check{I}_p)/\check{I}_p$$

where p is peptide transition, s is the biological sample, $I_{p,s}$ is the abundance of peptide transition p in the sample s, and $\check{I}_p$ is the corresponding median value in all technical replica.

According to one embodiment, the plurality of respective peptide transitions and the plurality of corresponding stable isotope-labeled internal standard (SIS) peptide transitions are mixed together within a sample before the measuring step.

According to another embodiment, the determination of the expression level of the target proteins is independent of the volume of the sample.

In one embodiment, the subject has a pulmonary nodule, wherein the pulmonary nodule has a diameter of 30 mm or less. Preferably, the pulmonary nodule has a diameter of about 8 and 30 mm.

In one embodiment, the subject has a lung condition. The lung condition may be cancer or a non-cancerous lung condition. In another embodiment, the lung cancer is non-small cell lung cancer. The non-cancerous lung conditions include chronic obstructive pulmonary disease, hamartoma, fibroma, neurofibroma, granuloma, sarcoidosis, bacterial infection or fungal infection.

The subject can be a mammal. Preferably, the subject is a human.

One embodiment of the current invention includes assessing the expression of a plurality of proteins by liquid chromatography-selected reaction monitoring/mass spectrometry (LC-SRM-MS). In another aspect of the invention, at least one transition for each peptide is determined by liquid chromatography-selected reaction monitoring/mass spectrometry (LC-SRM-MS).

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In the case of conflict, the present specification, including definitions, will control. In addition, the materials, methods, and examples are illustrative only and are not intended to be limiting. Other features and advantages of the invention will be apparent from the following detailed description and claim.

BRIEF DESCRIPTION OF THE DRAWINGS

FIG. 1 is a chart providing an overview of experimental variations and control methods. Panel (A) describes exemplar sources of variations. Systematic variations affect all proteins or peptides similarly. Protein- or peptide-specific variations affect only particular proteins or peptides. Random variations are not listed because they are not controllable. Panel (B) describes control of variations by different quantification methods in the analysis of plasma samples on a depletion-MRM-MS platform. Panel (C) provides an overview of three assessment studies and a combined HPS dataset.

DETAILED DESCRIPTION

Figure 2:
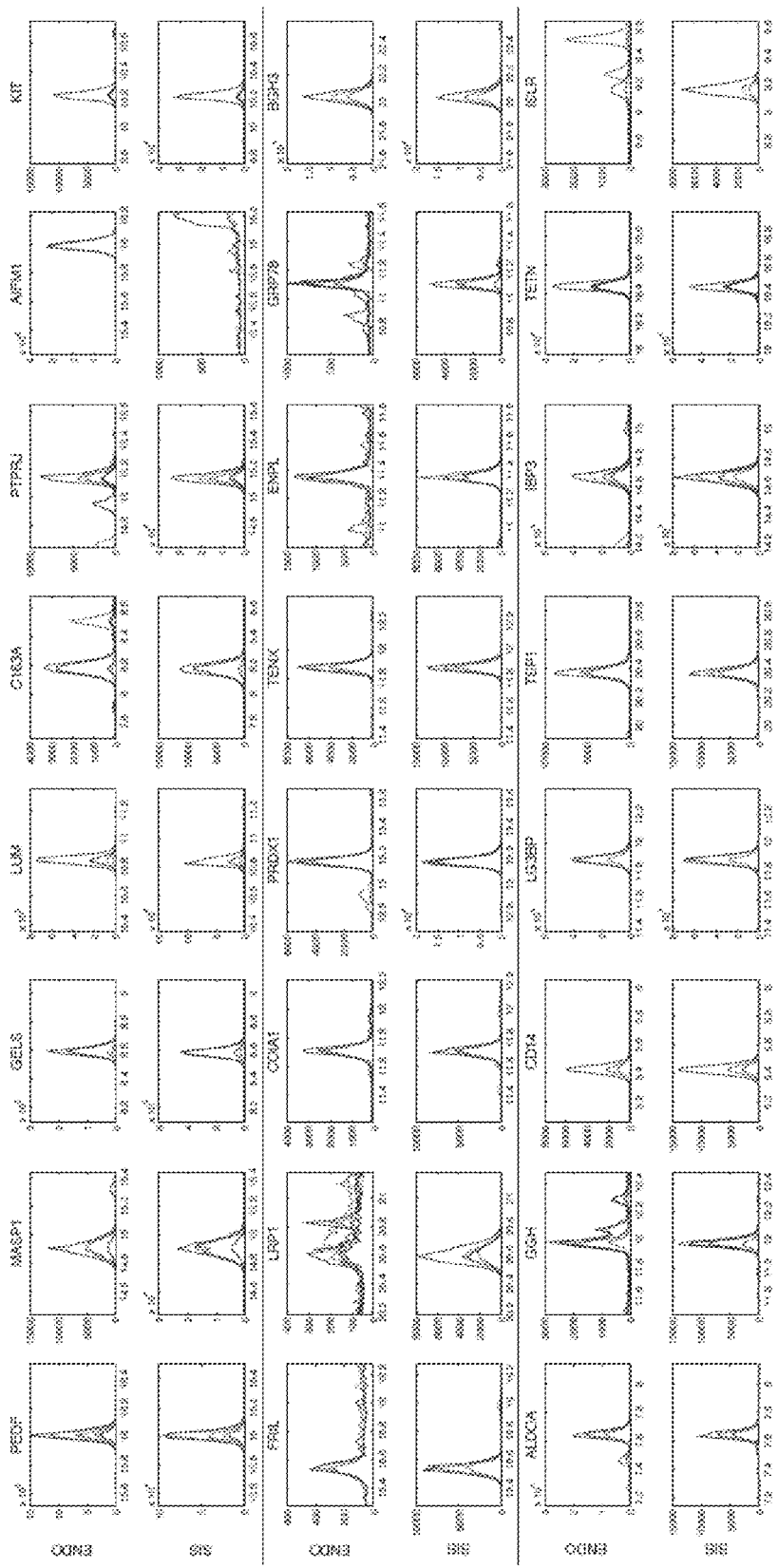
FIG. 2 is a set of chromatograms showing the transitions of both endogenous and SIS peptides of individual proteins. Proteins are plotted in the same order as in Table 1. Transitions of endogenous peptides are plotted in the first, third, and fifth rows. Transitions of the corresponding SIS peptides are plotted in the second, fourth and sixth rows.

The disclosed invention derives from the surprising discovery that endogenous protein normalization (EPN) and SISQuan may act synergistically in the control of different types of variations present in clinical proteomics. By selecting endogenous normalizing proteins for their ability to reduce both technical drift and technical variations of other proteins, rather than for their "housekeeping" properties, EPN may be combined with SISQuan in a unique fashion to provide numerous benefits and advantages over prior methods.

In summary, the quantification methods of the present invention demonstrate superiority to prior quantification methods such as SISQuan. The methods of the present invention are robust, simple to implement, capable of reducing pre-analytical and analytical variability, and able to improve the measurement of biological differences. All of these features make the methods of the present invention an ideal technique for MS-based quantitative proteomics, e.g., for applications in biomarker research and in routine clinical testing.

A. Definitions

The term "pulmonary nodules" (PNs) as used herein refers to lung lesions that can be visualized by radiographic techniques. A pulmonary nodule is any nodules less than or equal to three centimeters in diameter. In one example a pulmonary nodule has a diameter of about 0.8 cm to 3 cm.

The term "masses" or "pulmonary masses" as used herein refers to lung nodules that are greater than three centimeters maximal diameter.

The term "blood biopsy" as used herein refers to a diagnostic study of the blood to determine whether a patient presenting with a nodule has a condition that may be classified as either benign or malignant.

The term "acceptance criteria" as used herein refers to the set of criteria to which an assay, test, diagnostic or product should conform to be considered acceptable for its intended use. As used herein, acceptance criteria are a list of tests, references to analytical procedures, and appropriate measures, which are defined for an assay or product that will be used in a diagnostic. For example, the acceptance criteria for the classifier refer to a set of predetermined ranges of coefficients.

The term "partial AUC factor or pAUC factor" as used herein is greater than expected by random prediction. At specificity=0.80 the pAUC factor is the trapezoidal area under the ROC curve from 0.0 to 0.2 False Positive Rate/(0.2*0.2/2).

The term "robust" as used herein refers to a test or procedure that is not seriously disturbed by violations of the assumptions on which it is based. For the present invention, a robust test is a test wherein the proteins or transitions of the mass spectrometry chromatograms have been manually reviewed and are "generally" free of interfering signals.

The term "coefficients" as used herein refers to the weight assigned to each protein used to in the logistic regression model to score a sample.

In certain embodiments of the invention, it is contemplated that in terms of the logistic regression model of MC CV, the model coefficient and the coefficient of variation (CV) of each protein's model coefficient may increase or decrease, dependent upon the method (or model) of measurement of the protein classifier. For each of the listed proteins in the panels, there is about, at least, at least about, or at most about a 2-, 3-, 4-, 5-, 6-, 7-, 8-, 9-, or 10-, -fold or any range derivable therein for each of the coefficient and CV. Alternatively, it is contemplated that quantitative embodiments of the invention may be discussed in terms of as about, at least, at least about, or at most about 10, 20, 30, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more, or any range derivable therein.

The term "classifying" as used herein with regard to a lung condition refers to the act of compiling and analyzing expression data for using statistical techniques to provide a classification to aid in diagnosis of a lung condition, particularly lung cancer.

The term "classifier" as used herein refers to an algorithm that discriminates between disease states with a predetermined level of statistical significance. A two-class classifier is an algorithm that uses data points from measurements from a sample and classifies the data into one of two groups. In certain embodiments, the data used in the classifier is the relative expression of proteins in a biological sample. Protein expression levels in a subject can be compared to levels in patients previously diagnosed as disease free or with a specified condition. Table 5 lists representative rule-in classifiers (e.g., panels 1, 4, and 5).

The "classifier" maximizes the probability of distinguishing a randomly selected cancer sample from a randomly selected benign sample, i.e., the AUC of ROC curve.

In addition to the classifier's constituent proteins with differential expression, it may also include proteins with minimal or no biologic variation to enable assessment of variability, or the lack thereof, within or between clinical specimens; these proteins may be termed endogenous proteins and serve as internal controls for the other classifier proteins.

The term "normalization" or "normalizer" as used herein refers to the expression of a differential value in terms of a standard value to adjust for effects which arise from technical variation due to sample handling, sample preparation and mass spectrometry measurement rather than biological variation of protein concentration in a sample. For example, when measuring the expression of a differentially expressed protein, the absolute value for the expression of the protein can be expressed in terms of an absolute value for the expression of a standard protein that is substantially constant in expression. This prevents the technical variation of sample preparation and mass spectrometry measurement from impeding the measurement of protein concentration levels in the sample. A skilled artisan could readily recognize that any normalization methods and/or normalizers suitable for the present invention can be utilized.

The term "condition" as used herein refers generally to a disease, event, or change in health status.

The term "treatment protocol" as used herein includes further diagnostic testing typically performed to determine whether a pulmonary nodule is benign or malignant. Treatment protocols include diagnostic tests typically used to diagnose pulmonary nodules or masses such as for example, CT scan, positron emission tomography (PET) scan, bronchoscopy or tissue biopsy. Treatment protocol as used herein is also meant to include therapeutic treatments typically used to treat malignant pulmonary nodules and/or lung cancer such as for example, chemotherapy, radiation or surgery.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore the term diagnosis includes: a. prediction (determining if a patient will likely develop a hyperproliferative disease); b. prognosis (predicting whether a patient will likely have a better or worse outcome at a pre-selected time in the future); c. therapy selection; d. therapeutic drug monitoring; and e. relapse monitoring.

In some embodiments, for example, classification of a biological sample as being derived from a subject with a lung condition may refer to the results and related reports generated by a laboratory, while diagnosis may refer to the act of a medical professional in using the classification to identify or verify the lung condition.

The term "providing" as used herein with regard to a biological sample refers to directly or indirectly obtaining the biological sample from a subject. For example, "providing" may refer to the act of directly obtaining the biological sample from a subject (e.g., by a blood draw, tissue biopsy, lavage and the like). Likewise, "providing" may refer to the act of indirectly obtaining the biological sample. For example, providing may refer to the act of a laboratory receiving the sample from the party that directly obtained the sample, or to the act of obtaining the sample from an archive.

As used herein, "lung cancer" preferably refers to cancers of the lung, but may include any disease or other disorder of the respiratory system of a human or other mammal. Respiratory neoplastic disorders include, for example small cell carcinoma or small cell lung cancer (SCLC), non-small cell carcinoma or non-small cell lung cancer (NSCLC), squamous cell carcinoma, adenocarcinoma, broncho-alveolar carcinoma, mixed pulmonary carcinoma, malignant pleural mesothelioma, undifferentiated large cell carcinoma, giant cell carcinoma, synchronous tumors, large cell neuroendocrine carcinoma, adenosquamous carcinoma, undifferentiated carcinoma; and small cell carcinoma, including oat cell cancer, mixed small cell/large cell carcinoma, and combined small cell carcinoma; as well as adenoid cystic carcinoma, hamartomas, mucoepidermoid tumors, typical carcinoid lung tumors, atypical carcinoid lung tumors, peripheral carcinoid lung tumors, central carcinoid lung tumors, pleural mesotheliomas, and undifferentiated pulmonary carcinoma and cancers that originate outside the lungs such as secondary cancers that have metastasized to the lungs from other parts of the body. Lung cancers may be of any stage or grade. Preferably the term may be used to refer collectively to any dysplasia, hyperplasia, neoplasia, or metastasis in which the protein biomarkers expressed above normal levels as may be determined, for example, by comparison to adjacent healthy tissue.

Examples of non-cancerous lung condition include chronic obstructive pulmonary disease (COPD), benign tumors or masses of cells (e.g., hamartoma, fibroma, neurofibroma), granuloma, sarcoidosis, and infections caused by bacterial (e.g., tuberculosis) or fungal (e.g., histoplasmosis) pathogens. In certain embodiments, a lung condition may be associated with the appearance of radiographic PNs.

As used herein, "lung tissue" and "lung cancer" refer to tissue or cancer, respectively, of the lungs themselves, as well as the tissue adjacent to and/or within the strata underlying the lungs and supporting structures such as the pleura, intercostal muscles, ribs, and other elements of the respiratory system. The respiratory system itself is taken in this context as representing nasal cavity, sinuses, pharynx, larynx, trachea, bronchi, lungs, lung lobes, aveoli, aveolar ducts, aveolar sacs, aveolar capillaries, bronchioles, respiratory bronchioles, visceral pleura, parietal pleura, pleural cavity, diaphragm, epiglottis, adenoids, tonsils, mouth and tongue, and the like. The tissue or cancer may be from a mammal and is preferably from a human, although monkeys, apes, cats, dogs, cows, horses and rabbits are within the scope of the present invention. The term "lung condition" as used herein refers to a disease, event, or change in health status relating to the lung, including for example lung cancer and various non-cancerous conditions.

"Accuracy" refers to the degree of conformity of a measured or calculated quantity (a test reported value) to its actual (or true) value. Clinical accuracy relates to the proportion of true outcomes (true positives (TP) or true negatives (TN)) versus misclassified outcomes (false positives (FP) or false negatives (FN)), and may be stated as a sensitivity, specificity, positive predictive values (PPV) or negative predictive values (NPV), or as a likelihood, odds ratio, among other measures. The term "biological sample" as used herein refers to any sample of biological origin potentially containing one or more biomarker proteins. Examples of biological samples include tissue, organs, or bodily fluids such as whole blood, plasma, serum, tissue, lavage or any other specimen used for detection of disease.

The term "subject" as used herein refers to a mammal, preferably a human.

The term "biomarker protein" as used herein refers to a polypeptide in a biological sample from a subject with a lung condition versus a biological sample from a control subject. A biomarker protein includes not only the polypeptide itself, but also minor variations thereof, including for example one or more amino acid substitutions or modifications such as glycosylation or phosphorylation.

The term "biomarker protein panel" as used herein refers to a plurality of biomarker proteins. In certain embodiments, the expression levels of the proteins in the panels can be correlated with the existence of a lung condition in a subject. In certain embodiments, biomarker protein panels comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 proteins. In certain embodiments, the biomarker proteins panels comprise 2-5 proteins, 5-10 proteins, 10-20 proteins or more.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Biomarker levels may change due to treatment of the disease. The changes in biomarker levels may be measured by the present invention. Changes in biomarker levels may be used to monitor the progression of disease or therapy.

"Altered", "changed" or "significantly different" refer to a detectable change or difference from a reasonably comparable state, profile, measurement, or the like. One skilled in the art should be able to determine a reasonable measurable change. Such changes may be all or none. They may be incremental and need not be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively the change may be 1-fold, 1.5-fold 2-fold, 3-fold, 4-fold, 5-fold or more, or any values in between 1-fold and five-fold. The change may be statistically significant with a p value of 0.1, 0.05, 0.001, or 0.0001.

Using the methods of the current invention, a clinical assessment of a patient is first performed. If there exists is a higher likelihood for cancer, the clinician may rule in the disease which will require the pursuit of diagnostic testing options yielding data which increase and/or substantiate the likelihood of the diagnosis. "Rule in" of a disease requires a test with a high specificity.

"FN" is false negative, which for a disease state test means classifying a disease subject incorrectly as non-disease or normal.

"FP" is false positive, which for a disease state test means classifying a normal subject incorrectly as having disease.

The term "rule in" refers to a diagnostic test with high specificity that optionally coupled with a clinical assessment indicates a higher likelihood for cancer. If the clinical assessment is a lower likelihood for cancer, the clinician may adopt a stance to rule out the disease, which will require diagnostic tests which yield data that decrease the likelihood of the diagnosis. "Rule out" requires a test with a high sensitivity. Accordingly, the term "ruling in" as used herein is meant that the subject is selected to receive a treatment protocol.

The term "rule out" refers to a diagnostic test with high sensitivity that optionally coupled with a clinical assessment indicates a lower likelihood for cancer. Accordingly, the term "ruling out" as used herein is meant that the subject is selected not to receive a treatment protocol.

The term "sensitivity of a test" refers to the probability that a patient with the disease will have a positive test result. This is derived from the number of patients with the disease who have a positive test result (true positive) divided by the total number of patients with the disease, including those with true positive results and those patients with the disease who have a negative result, i.e., false negative.

The term "specificity of a test" refers to the probability that a patient without the disease will have a negative test result. This is derived from the number of patients without the disease who have a negative test result (true negative) divided by all patients without the disease, including those with a true negative result and those patients without the disease who have a positive test result, e.g., false positive. While the sensitivity, specificity, true or false positive rate, and true or false negative rate of a test provide an indication of a test's performance, e.g., relative to other tests, to make a clinical decision for an individual patient based on the test's result, the clinician requires performance parameters of the test with respect to a given population.

The term "positive predictive value" (PPV) refers to the probability that a positive result correctly identifies a patient who has the disease, which is the number of true positives divided by the sum of true positives and false positives.

The term "negative predictive value" or "NPV" is calculated by TN/(TN+FN) or the true negative fraction of all negative test results. It also is inherently impacted by the prevalence of the disease and pre-test probability of the population intended to be tested. The term NPV refers to the probability that a negative test correctly identifies a patient without the disease, which is the number of true negatives divided by the sum of true negatives and false negatives. A positive result from a test with a sufficient PPV can be used to rule in the disease for a patient, while a negative result from a test with a sufficient NPV can be used to rule out the disease, if the disease prevalence for the given population, of which the patient can be considered a part, is known.

The term "disease prevalence" refers to the number of all new and old cases of a disease or occurrences of an event during a particular period. Prevalence is expressed as a ratio in which the number of events is the numerator and the population at risk is the denominator.

The term disease incidence refers to a measure of the risk of developing some new condition within a specified period of time; the number of new cases during some time period, it is better expressed as a proportion or a rate with a denominator.

Lung cancer risk according to the "National Lung Screening Trial" is classified by age and smoking history. High risk—age ≥55 and ≥30 pack-years smoking history; Moderate risk—age ≥50 and ≥20 pack-years smoking history; Low risk—<age 50 or <20 pack-years smoking history.

The clinician must decide on using a diagnostic test based on its intrinsic performance parameters, including sensitivity and specificity, and on its extrinsic performance parameters, such as positive predictive value and negative predictive value, which depend upon the disease's prevalence in a given population.

Additional parameters which may influence clinical assessment of disease likelihood include the prior frequency and closeness of a patient to a known agent, e.g., exposure risk, that directly or indirectly is associated with disease causation, e.g., second hand smoke, radiation, etc., and also the radiographic appearance or characterization of the pulmonary nodule exclusive of size. A nodule's description may include solid, semi-solid or ground glass which characterizes it based on the spectrum of relative gray scale density employed by the CT scan technology.

"Mass spectrometry" refers to a method comprising employing an ionization source to generate gas phase ions from an analyte presented on a sample presenting surface of a probe and detecting the gas phase ions with a mass spectrometer.

B. Development of InteQuan

Figure 1:
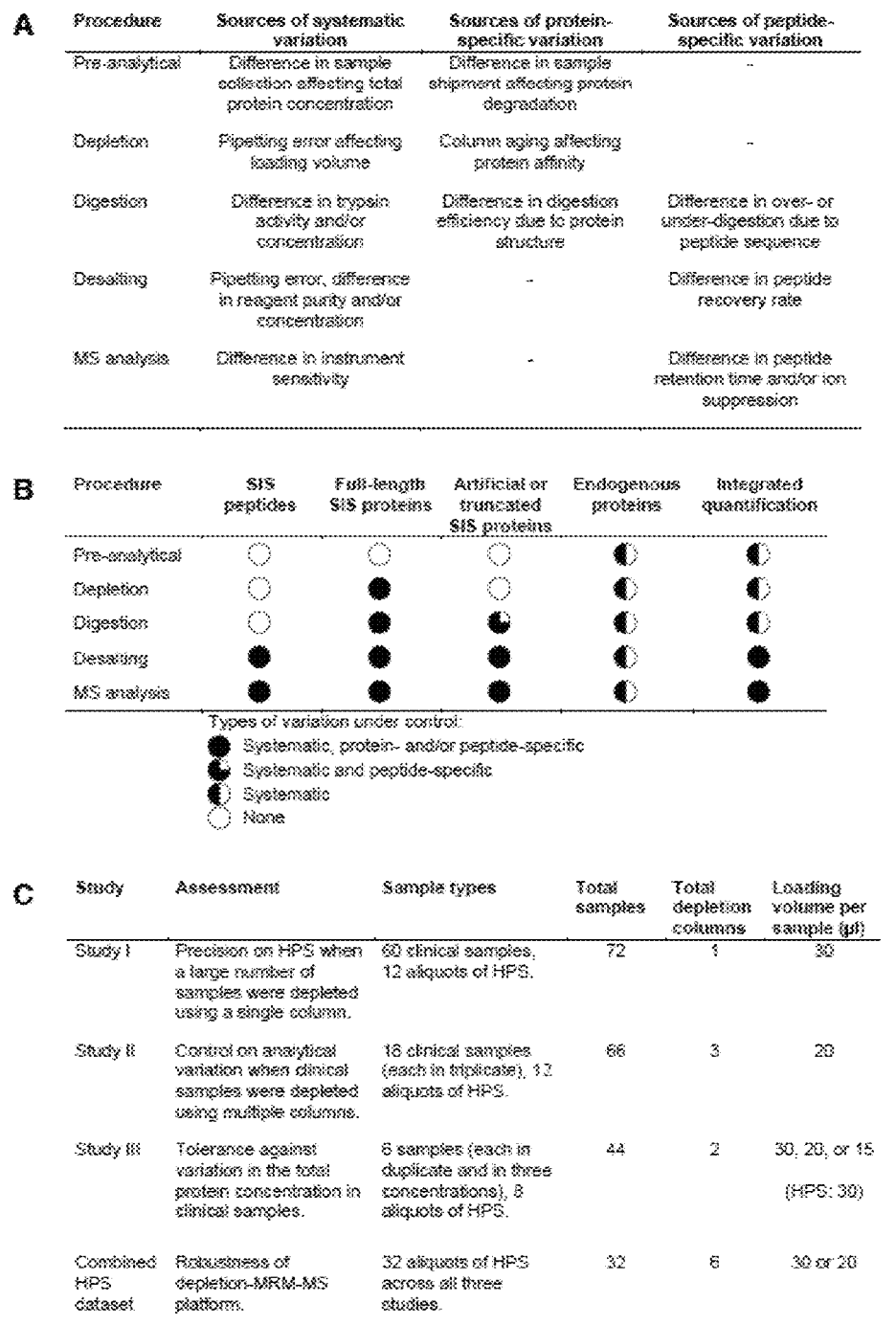

Hundreds of human plasma samples were analyzed in a prior label-free discovery study of lung cancer biomarkers, using immunoaffinity-based protein depletion coupled with MRM-MS (depletion-MRM-MS) (Li, X J et al, *Sci. Tranl. Med.* 2013, 5:207ra142). Six endogenous normalizing proteins were identified in this study out of 371 protein candidates. Since the normalizing proteins were processed and analyzed together with target proteins of interest, it was expected that they would serve as monitors for systematic variation in both pre-analytical and analytical procedures (FIG. 1B). It has been verified that experimental variability was reduced after normalization by a panel of the six proteins.

Although this method of endogenous protein normalization (EPN) and similar approaches have been reported previously in quantitative proteomics, the approach taken by the present invention is unique. The six normalizing proteins were selected by their ability to compensate both the drift of depletion columns and the technical variation of other proteins, rather than their "housekeeping" properties as utilized in other approaches. However, the EPN quantification method used in our previous study is a label-free approach and cannot control analytical variability as narrowly as the three SIL approaches.

The present invention comprises more accurate MRM assays for target proteins of interest, using the SIL approach of SIS peptides. As described herein, neither SIL nor EPN is ideal for protein quantification in clinical proteomics. To deal with this challenge, the methods of the present invention describe a new quantification method, named integrated quantification (InteQuan), which uniquely combines the advantageous features of two methods: EPN and SISQuan. As further described in the Examples below, six endogenous normalizing proteins were used to compensate systematic variation in pre-analytical procedures and in depletion and digestion, while SIS peptides were used to control variation in desalting and MS analysis (FIG. 1B).

To mimic an actual clinical testing scenario, the details of the methods of the present invention were defined based on data from a different study (Vachani et al., Validation of a Multi-Protein Plasma Classifier to Identify Benign Lung Nodules, *J. Thoracic Onc.* (doi: 10.1097/JTO.0000000000000447)) before assessing its performance in three independent studies (FIG. 1C), Studies I-III, which are further described in the Examples. No one has previously described such a method to quantify individual proteins before. A recent work used "sparse reference labeling" to anchor protein abundance that can be valuable for biomarker discovery (Chang, C T et al, Targeted protein quantification using spare reference labeling, *Nat. Methods* 2014, 11:301-304). Nevertheless, individual proteins were essentially quantified in a label-free approach in the study, leaving peptide-specific variation in MS analysis uncontrolled and thus reducing its validity for routine clinical testing. The methods of the present invention, utilizing aspects of the newly developed InteQuan, demonstrate increased precision, robustness, and resolution of protein measurement in the three independent assessment studies, Studies I-III (FIG. 1 C).

C. Advantages of InteQuan

At least three aspects of InteQuan and the methods of the present invention enhance their relevance towards the development of blood-based laboratory-developed tests using MRM-MS platforms. First, the target proteins used in the development of InteQuan were all potential lung cancer biomarkers. Second, endogenous proteins in low ng/ml to low µg/ml plasma concentrations were quantified in both clinical plasma samples and in the standard HPS samples. Third, the longitudinal assessment on the robustness of the depletion-MRM-MS platform was performed in settings similar to actual laboratory operations for clinical testing. In contrast, medium- to high-abundant endogenous proteins, spike-in peptides or spike-in proteins were quantified on single plasma samples, in settings of academic research rather than clinical testing, and using different MRM-MS platforms in other studies. Nevertheless, the precision obtained from the development of InteQuan was comparable to the precision reported in those studies. Furthermore, the precision of the whole depletion-MRM-MS platform was assessed in the development of InteQuan, not just the precision of MRM-MS platforms as in some studies.

In one aspect, the selection of proper endogenous normalizing proteins provides the advantageous performance of InteQuan relative to other quantification methods. According to error propagation theory, normalization by endogenous proteins has two opposite effects. On one hand, it reduces the overall variability in protein measurement by cancelling out systematic variation that similarly affects target and normalizing proteins. On the other hand, it increases the overall variability by transferring protein-specific and random variation of normalizing proteins to target proteins.

Three strategies were applied to ensure a favorable outcome from the normalization process utilized in various aspects of the methods of the present invention. First, a large dataset was generated to capture both technical variability on the platform and biological variability of the intended patient population. Owing to considerations of cost, a label-free approach was used to quantify proteins in the study. Second, six normalizing proteins were selected for their performance in reducing column drift and technical CV of other proteins. In other words, the proteins were specifically selected to fulfill the role of normalizers. Third, the six normalizing proteins were used as a panel that was more stable compared to individual proteins. In addition, although plasma concentration was not used as a selection criterion, the wide concentration range (three orders of magnitude) of the six normalizing proteins was likely beneficial. Similar strategies should be used for selecting endogenous normalizing proteins on other MS platforms and/or for other proteomics projects. In our case, the six normalizing proteins were selected from a pool of 371 protein candidates based on a set of label-free depletion-MRM-MS data.

Figure 8:
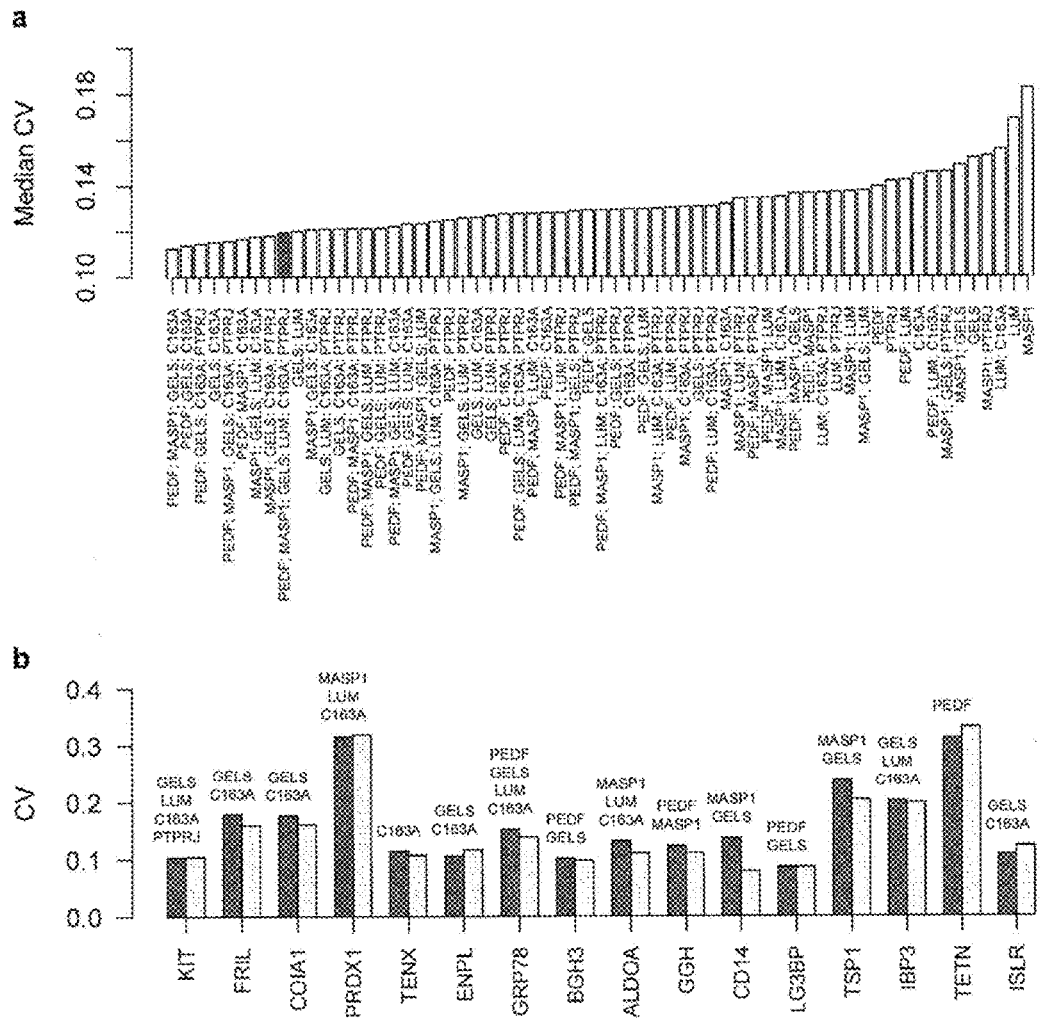
FIG. 8 is a pair of graphs showing an assessment of alternative normalization panels for InteQuan. Panel (A) shows the median coefficient of variation (CV) of the target proteins after normalization by all possible combination of six normalizing proteins. Panel (B) shows the CV of the target proteins as evaluated using the "optimal" panel versus using the full panel.

It is possible that other proteins outside the pool may serve as normalizers for on other MS platforms. As shown later in FIG. 8, different combinations of normalizers may be used. Accordingly, the methods of endogenous normalizing protein selection described herein may be used to select normalizing proteins for different MS platform techniques and/or focused on quantifying biomarkers for diseases other than lung disease.

InteQuan measures the abundance of the target proteins relative to the abundance of the endogenous normalizing proteins, which explains its high tolerance against variation in the total protein concentration. When testing actual clinical samples, pre-analytical variability (due to differences in patient posture, diurnal cycle, sample collection, and/or sample handling, etc.) and analytical variability (due to differences in sample loading volume, instrument performance, and/or operator, etc.) are hard to avoid and all contribute to the overall variability of the assay. Thus, a high tolerance against such variation is a desirable feature that will increase the reproducibility of clinical tests.

In summary, InteQuan has been developed as a quantification method for, e.g, MS-based quantitative proteomics, and has demonstrated its superiority to SISQuan in three independent studies and on a combined HPS dataset described in the Examples. The InteQuan method is robust, simple to implement, capable of reducing pre-analytical and analytical variability, and able to improve the measurement of biological differences. All these features make the method an ideal technique for MS-based quantitative proteomics, e.g., for applications in biomarker research and in routine clinical testing.

D. Applications of InteQuan

According to one aspect of the methods of the present invention, the abundance or expression level of protein biomarkers for lung disease may be measured by MS. MS analyzes the mass spectrum produced by an ion after its production by the vaporization of its parent protein and its separation from other ions based on its mass-to-charge ratio. The most common modes of acquiring MS data are 1) full scan acquisition resulting in the typical total ion current plot (TIC), 2) selected ion monitoring (SIM), and 3) selected reaction monitoring (SRM).

In certain embodiments of the methods provided herein, biomarker protein expression levels are measured by LC-SRM-MS. LC-SRM-MS is a highly selective method of tandem mass spectrometry which has the potential to effectively filter out all molecules and contaminants except the desired analyte(s). This is particularly beneficial if the analysis sample is a complex mixture which may comprise several isobaric species within a defined analytical window. LC-SRM-MS methods may utilize a triple quadrupole mass spectrometer which, as is known in the art, includes three quadrupole rod sets. A first stage of mass selection is performed in the first quadrupole rod set, and the selectively transmitted ions are fragmented in the second quadrupole rod set. The resultant transition (product) ions are conveyed to the third quadrupole rod set, which performs a second stage of mass selection. The product ions transmitted through the third quadrupole rod set are measured by a detector, which generates a signal representative of the numbers of selectively transmitted product ions. The RF and DC potentials applied to the first and third quadrupoles are tuned to select (respectively) precursor and product ions that have m/z values lying within narrow specified ranges. By specifying the appropriate transitions (m/z values of precursor and product ions), a peptide corresponding to a targeted protein may be measured with high degrees of sensitivity and selectivity. Signal-to-noise ratio is superior to conventional tandem mass spectrometry (MS/MS) experiments, which select one mass window in the first quadrupole and then measure all generated transitions in the ion detector. LC-SRM-MS.

The expression level of a biomarker protein can be measured using any suitable method known in the art, including but not limited to mass spectrometry (MS), reverse transcriptase-polymerase chain reaction (RT-PCR), microarray, serial analysis of gene expression (SAGE), gene expression analysis by massively parallel signature sequencing (MPSS), immunoassays (e.g., ELISA), immunohistochemistry (IHC), transcriptomics, and proteomics.

According to one aspect of the methods, the measuring step is performed by selected reaction monitoring mass spectrometry, using a compound that specifically binds the protein being detected or a peptide transition. In one embodiment, the compound that specifically binds to the protein being measured is an antibody or an aptamer.

According to one aspect of the methods, the biological sample includes such as for example tissue, blood, plasma, serum, whole blood, urine, saliva, genital secretion, cerebrospinal fluid, sweat and excreta.

In some embodiments of the methods, the determination of the abundance or expression level of the target proteins provides a diagnosis of lung disease. Accordingly, the methods of the present invention may serve as diagnostic methods.

In certain embodiments, the diagnostic methods disclosed herein can be used in combination with other clinical assessment methods, including for example various radiographic and/or invasive methods. Similarly, in certain embodiments, the diagnostic methods disclosed herein can be used to identify candidates for other clinical assessment methods, or to assess the likelihood that a subject will benefit from other clinical assessment methods.

To evaluate the diagnostic performance of a particular set of peptide transitions, a ROC curve is generated for each significant transition.

An "ROC curve" as used herein refers to a plot of the true positive rate (sensitivity) against the false positive rate (specificity) for a binary classifier system as its discrimination threshold is varied. A ROC curve can be represented equivalently by plotting the fraction of true positives out of the positives (TPR=true positive rate) versus the fraction of false positives out of the negatives (FPR=false positive rate). Each point on the ROC curve represents a sensitivity/specificity pair corresponding to a particular decision threshold.

AUC represents the area under the ROC curve. The AUC is an overall indication of the diagnostic accuracy of 1) a biomarker or a panel of biomarkers and 2) a ROC curve. AUC is determined by the "trapezoidal rule." For a given curve, the data points are connected by straight line segments, perpendiculars are erected from the abscissa to each data point, and the sum of the areas of the triangles and trapezoids so constructed is computed. In certain embodiments of the methods provided herein, a biomarker protein has an AUC in the range of about 0.75 to 1.0. In certain of these embodiments, the AUC is in the range of about 0.8 to 0.85, 0.85 to 0.9, 0.9 to 0.95, or 0.95 to 1.0.

According to one aspect of the methods of the present invention, the subject has or is suspected of having a pulmonary nodule or a pulmonary mass. The pulmonary nodule has a diameter of less than or equal to 3.0 cm. The pulmonary mass has a diameter of greater than 3.0 cm. In some embodiments, the pulmonary nodule has a diameter of about 0.8 cm to 3.0 cm. The subject may have stage IA lung cancer (i.e., the tumor is smaller than 3 cm).

The high abundance of certain proteins in a biological sample such as plasma or serum can hinder the ability to assay a protein of interest, particularly where the protein of interest is expressed at relatively low concentrations. Several methods are available to circumvent this issue, including enrichment, separation, and depletion. Enrichment uses an affinity agent to extract proteins from the sample by class, e.g., removal of glycosylated proteins by glycocapture. Separation uses methods such as gel electrophoresis or isoelectric focusing to divide the sample into multiple fractions that largely do not overlap in protein content. Depletion typically uses affinity columns to remove the most abundant proteins in blood, such as albumin, by utilizing advanced technologies such as IgY14/Supermix (Sigma St. Louis, Mo.) that enable the removal of the majority of the most abundant proteins.

In certain embodiments of the methods provided herein, a biological sample may be subjected to enrichment, separation, and/or depletion prior to assaying biomarker or putative biomarker protein expression levels. In certain of these embodiments, blood proteins may be initially processed by a glycocapture method, which enriches for glycosylated proteins, allowing quantification assays to detect proteins in the high pg/ml to low ng/ml concentration range. Exemplary methods of glycocapture are well known in the art (see, e.g., U.S. Pat. No. 7,183,188; U.S. Patent Appl. Publ. No. 2007/0099251; U.S. Patent Appl. Publ. No. 2007/0202539; U.S. Patent Appl. Publ. No. 2007/0269895; and U.S. Patent Appl. Publ. No. 2010/0279382). In other embodiments, blood proteins may be initially processed by a protein depletion method, which allows for detection of commonly obscured biomarkers in samples by removing abundant proteins. In one such embodiment, the protein depletion method is a Supermix (Sigma) depletion method.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention

EXAMPLES

Example 1

Protein Quantification in Human Plasma Samples

A total of 21 lung cancer biomarker candidates were identified in a prior discovery study (Li, X J et al, *Sci. Tranl. Med.* 2013, 5:207ra142). Two of the 21 candidates (GSLG1 and EF1A1) were eliminated from this study due to weak signals on a new MRM-MS platform. Another candidate (FIBA) was eliminated due to its affinity to the depletion column. With reference to Table 1, the remaining 18 candidates were targeted for quantification in human plasma samples.

TABLE 1

List of six normalizing proteins and eighteen target proteins of interest

| Protein name | Concentration[a] (ng/ml) | Transition[b] (peptide (SEQ ID NO)_Q1_Q3) | FDR[c] | $F_n$[d] | $Ř_n$[e] |
|---|---|---|---|---|---|
| Pigment epithelium-derived factor | 7200 | LQSLFDSPDFSK (SEQ ID NO: 25) _692.34_593.30 | 1.40E−04 | 0.971 | 1.756 |
| Mannan-binding lectin serine protease 1 | 240 | TGVITSPDFPNPYPK (SEQ ID NO: 26) _816.92_258.10 | 5.75E−04 | 0.957 | 0.360 |
| Gelsolin | 16000 | TASDFITK(SEQ ID NO: 27) _441.73_710.40 | 3.18E−04 | 0.852 | 0.502 |
| Lumican | 4000 | SLEDLQLTHNK (SEQ ID NO: 28)_433.23_499.30 | 3.82E−04 | 0.838 | 10.846 |
| Scavenger receptor cysteine-rich type 1 protein M130 | 94 | INPASLDK (SEQ ID NO: 29)_429.24_630.30 | 1.19E−03 | 0.823 | 0.392 |
| Receptor-type tyrosine-protein phosphatase eta | 9.9 | VITEPIPVSDLR (SEQ ID NO: 30)_669.89_896.50 | 1.44E−03 | 0.926 | 0.275 |
| Apoptosis-inducing factor 1, mitochondrial | 1.4 | ELWFSDDPNVTK (SEQ ID NO: 31)_725.85_558.30 | 3.70E−02 | Assay specificity not verified | |
| Mast/stem cell growth factor receptor | 8.2 | YVSELHLTR (SEQ ID NO: 32) _373.21_428.30 | 2.40E−03 | 0.730 | |
| Ferritin light chain | 12 | LGGPEAGLGEYLFER(SEQ ID NO: 33) _804.40_1083.60 | 4.30E−05 | 0.844 | |
| Prolow-density lipoprotein receptor-related protein 1 | 20 | TVLWPNGLSLDIPAGR(SEQ ID NO: 34) _855.00_1209.70 | 1.40E−04 | Assay specificity not verified | |
| Collagen alpha-1(XVIII) chain | 35 | AVGLAGTFR(SEQ ID NO: 35) _446.26_721.40 | 6.70E−04 | 0.732 | |
| Peroxiredoxin-1 | 60 | QITVNDLPVGR (SEQ ID NO: 36)_606.30_970.50 | 1.90E−05 | 1.714 | |
| Tenascin-X | 70 | YEVTVVSVR(SEQ ID NO: 37) _526.29_293.10 | 1.10E−03 | 0.699 | |
| Endoplasmin | 88 | SGYLLPDTK(SEQ ID NO: 38) _497.27_308.10 | 1.10E−03 | 0.649 | |
| 78 kDa glucose-regulated protein | 100 | TWNDPSVQQDIK (SEQ ID NO: 39) _715.85_288.10 | 1.80E−03 | 1.140 | |
| Transforming growth factor-beta-induced protein ig-h3 | 140 | LTLLAPLNSVFK(SEQ ID NO: 40) _658.40_804.50 | 1.40E−04 | 0.779 | |

TABLE 1-continued

List of six normalizing proteins and eighteen target proteins of interest

| Protein name | Con-<br>centration[a]<br>(ng/ml) | Transition[b]<br>(peptide (SEQ ID NO)_Q1_Q3) | FDR[c] | $F_n{}^d$ | $\check{R}_n{}^e$ |
|---|---|---|---|---|---|
| Fructose-bisphosphate aldolase A | 250 | ALQASALK(SEQ ID NO: 41) _401.25_617.40 | 3.70E−05 | 0.777 | |
| Gamma-glutamyl hydrolase | 250 | YYIAASYVK(SEQ ID NO: 42) _539.28_638.40 | 1.70E−03 | 0.834 | |
| Monocyte differentiation antigen CD14 | 420 | ATVNPSAPR(SEQ ID NO: 43) _456.80_527.30 | 4.30E−04 | 0.789 | |
| Galectin-3-binding protein | 440 | VEIFYR (SEQ ID NO: 44)_413.73_598.30 | 2.80E−05 | 0.842 | |
| Thrombospondin-1 | 510 | GFLLLASLR(SEQ ID NO: 45) _495.31_559.40 | 1.90E−05 | 0.625 | |
| Insulin-like growth factor-binding protein 3 | 5700 | FLNVLSPR (SEQ ID NO: 46)_473.28_685.40 | 2.80E−05 | 0.790 | |
| Tetranectin | 58000 | LDTLAQEVALLK(SEQ ID NO: 47) _657.39_871.50 | 3.70E−05 | 0.760 | |
| Immunoglobulin superfamily containing leucine-rich repeat protein | | ALPGTPVASSQPR(SEQ ID NO: 48) _640.85_841.50 | 4.40E−03 | 0.850 | |

[a]Predicted plasma concentration [26].
[b]The transition that was used for quantification.
[c]False discovery rate for peptide MRM assay (peptide Q value) [6].
[d]Correction factor {$F_n$} in Study II in which a new lot of SIS peptides were used.
[e]Scaling constant {$\check{R}_n$} for InteQuan.
[f]Scaling constant {$\check{A}_n$} for EPN.

With further reference to Table 1, six endogenous normalizing proteins were selected from a pool of 371 protein candidates in a previous label-free discovery study (Li, X J et al, *Sci. Tranl. Med.* 2013, 5:207ra142). The predicted plasma concentration of the six proteins, estimated from the occurrence of protein detection in human plasma or serum samples by the proteomics community, ranged from 9.9 ng/ml (PTPRJ) to 16 µg/ml (GELS). All six proteins were used as normalizing proteins for InteQuan and for EPN in this study.

Human plasma samples were analyzed on a depletion-MRM-MS platform. SIS peptides of the target and the normalizing proteins were synthesized and spiked into peptide samples after digestion. The specificity of MRM assays to the corresponding proteins was verified for all proteins except for LRP1 and AIFM1. As shown in FIG. 2, MRM signals of verified assays were well above the corresponding noise level; endogenous and SIS peptides coeluted and had comparable intensity ratios between different transitions. The highest false discovery rate (FDR) of the original assays was 0.44% (ISLR, see Table 1).

Figure 7:
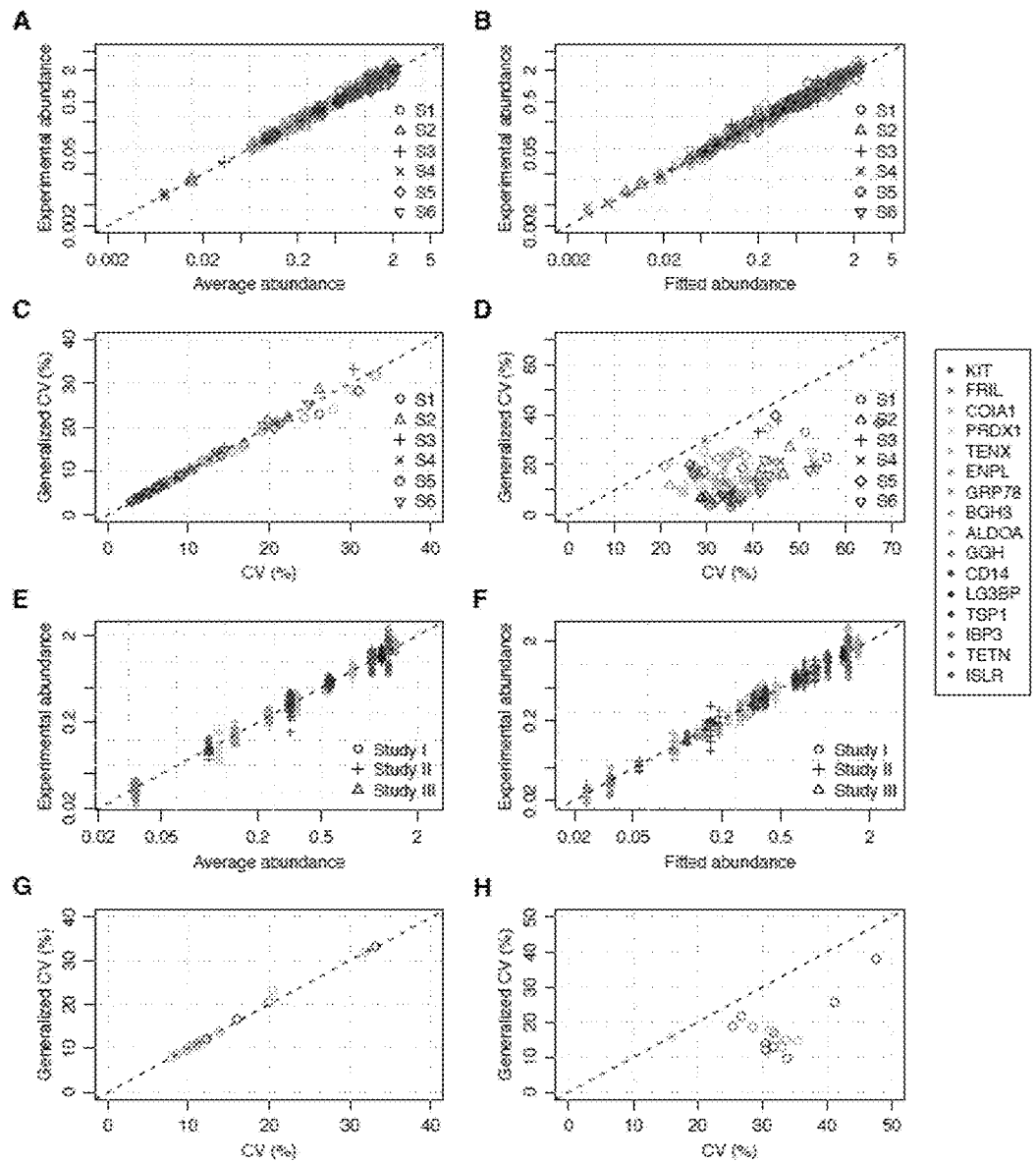
FIG. 7 is a set of graphs showing the calculation of generalized coefficient of variation (CV). Panels (A-D) show the results of all six clinical samples in Study III described in the Examples. Panels (E-H) show the results of the 29 HPS samples across all three studies described in the Examples. Panels (A, E) show the average InteQuan abundance versus experimental InteQuan abundance of individual proteins in individual samples. Panels (B, F) show the fitted SISQuan abundance versus experimental SISQuan abundance of individual proteins in individual samples. Panels (C, G) show the standard CV versus the generalized CV of InteQuan abundance. Panels (D, H) show the standard CV versus the generalized CV of SISQuan abundance.

As shown later in FIG. 7B, proteins were also measured within the respective linear dynamic range of the assays. Two blank samples were processed and analyzed at the end of each experimental batch in Study II and III to monitor possible carryover from previous samples (see Table 2). MRM signals in those blank samples were just above noise level (data not shown), indicating that carryover was not a problem for the depletion-MRM-MS platform. After validating the MRM assays, LRP1 and AIFM1 were both eliminated from further analysis. The predicted plasma concentration of the 16 remaining target proteins spanned four orders of magnitude from 8.2 ng/ml (KIT) to 58 µg/ml (TETN).

TABLE 2

Sample layout in the three assessment studies[a,b]

| Position | Study I Batch | | | Study II Batch | | | Study III[c] Batch | |
|---|---|---|---|---|---|---|---|---|
| | 1 | 2 | 3 | 1 | 2 | 3 | 1 | 2 |
| 1 | HPS | HPS | HPS | HPS | HPS | HPS | HPS | HPS |
| 2 | S1 | S21 | S41 | S1 | S13 | S16 | S1-L1 | S1-L0 |
| 3 | S2 | S22 | S42 | S2 | S2 | S2 | S1-L0 | S1-L2 |
| 4 | S3 | S23 | S43 | S3 | S14 | S17 | S1-L2 | S1-L1 |
| 5 | S4 | S24 | S44 | S4 | S4 | S4 | S2-L0 | S2-L1 |
| 6 | S5 | S25 | S45 | S5 | S15 | S18 | S2-L2 | S2-L0 |
| 7 | S6 | S26 | S46 | S6 | S6 | S6 | S2-L1 | S2-L2 |
| 8 | HPS | HPS | HPS | HPS | HPS | HPS | HPS | HPS |
| 9 | S7 | S27 | S47 | S1 | S13 | S16 | S3-L2 | S3-L0 |
| 10 | S8 | S28 | S48 | S7 | S7 | S7 | S3-L1 | S3-L2 |
| 11 | S9 | S29 | S49 | S3 | S14 | S17 | S3-L0 | S3-L1 |
| 12 | S10 | S30 | S50 | S8 | S8 | S8 | S4-L1 | S4-L2 |
| 13 | S11 | S31 | S51 | S5 | S15 | S18 | S4-L0 | S4-L1 |
| 14 | S12 | S32 | S52 | S9 | S9 | S9 | S4-L2 | S4-L0 |
| 15 | S13 | S33 | S53 | HPS | HPS | HPS | HPS | HPS |
| 16 | S14 | S34 | S54 | S1 | S13 | S16 | S5-L1 | S5-L0 |
| 17 | HPS | HPS | HPS | S10 | S10 | S10 | S5-L2 | S5-L1 |
| 18 | S15 | S35 | S55 | S3 | S14 | S17 | S5-L0 | S5-L2 |
| 19 | S16 | S36 | S56 | S11 | S11 | S11 | S6-L0 | S6-L1 |
| 20 | S17 | S37 | S57 | S5 | S15 | S18 | S6-L1 | S6-L2 |
| 21 | S18 | S38 | S58 | S12 | S12 | S12 | S6-L2 | S6-L0 |
| 22 | S19 | S39 | S59 | HPS | HPS | HPS | HPS | HPS |
| 23 | S20 | S40 | S60 | NC | NC | NC | NC | NC |
| 24 | HPS | HPS | HPS | NC | NC | NC | NC | NC |

[a]HPS, human plasma standard. NC, negative control (0.15M (NH$_4$)HCO$_3$).
[b]Samples with no data were highlighted in box and were lost due to 1) unexpected pump stoppage and restarting during depletion (the first HPS in Study I), 2) sample exhaustion (the sample in Study III) or 3) sample contamination during solid-phase extraction (all other samples).
[c]The loading volume for sample labeled as L0, L1, and L2 was 30, 20 or 15 µl, respectively.

The target proteins were quantified based on MRM-MS data using four different methods (raw MS data, EPN, SISQuan and InteQuan). In this study, the abundance of a protein was evaluated based on the MRM signal intensity of the strongest transition from the protein. Thus, no distinction was made between protein abundance, peptide abundance and transition abundance. For raw MS data, protein abundance was measured by the peak area of the strongest transition of the protein. For EPN, protein abundance using the raw MS data was divided by a sample-dependent normalization factor that was calculated from the peak areas of the six normalizing proteins. Six scaling constants, one for each of the six normalizing proteins, were used in the calculation of the normalization factor. For SISQuan, protein abundance was measured by the response ratio between the peak area of the strongest transition of the target protein and the peak area of the matching transition of the corresponding SIS peptide. For InteQuan, protein abundance using SISQuan was divided by a sample-dependent normalization factor that was calculated from the response ratios of the six normalizing proteins. As with EPN, six scaling constants were used in the calculation of the normalization factor. In the study, we mainly focused on comparing the new InteQuan method with the widely used SISQuan method.

With reference to Table 1, all scaling constants for InteQuan and for EPN were determined from a different study of 100 clinical samples and 20 aliquots of a human plasma standard (HPS) sample. See Vachani et al., Validation of a Multi-Protein Plasma Classifier to Identify Benign Lung Nodules, J. Thoracic Oncology (doi: 10.1097/JTO.0000000000000447). None of the scaling constants were modified in this study. Therefore, the assessment of the four quantification methods was based on independent datasets.

A. Clinical Samples

Archival K2-EDTA plasma samples were obtained from subjects that provided informed consent and with approval by either the Ethics Review Board at Institut Universitaire de Cardiologie et de Pneumologie de Quebec or the Institutional Review Boards at New York University and University of Pennsylvania. All samples were collected prior to surgery or from patients without surgery. Disease status of patients was histopathologically confirmed. All cancer patients were at Stage I or II. Clinical data associated with subjects were handled in accordance with the guidance established by the Health Insurance Portability and Accountability Act of 1996 to ensure subject privacy.

B. Selection of Endogenous Normalizing Proteins

In a prior discovery study, 72 cancer and 71 benign samples were analyzed in five experimental batches along with 15 aliquots of a pooled HPS sample that was purchased from Bioreclamation (Hicksville, N.Y.) (Li, X J et al, *Sci. Tranl. Med.* 2013, 5:207ra142). The HPS samples were embedded among clinical samples and analyzed repeatedly to monitor analytical variability in the experiment. The clinical samples were used to represent biological variability and possible pre-analytical variability.

Endogenous normalizing proteins were selected from proteins whose strongest transitions were detected in all samples. Each protein candidate was used to normalize the abundance of other proteins and evaluated based on the following criteria: (A) Its rank, as a normalizer, in reducing median technical CV of other proteins; (B) its rank in compensating median column drift, that is a technical variation associated with depletion; (C) its own median technical CV on HPS samples; and (D) its own median biological CV on clinical samples.

In the end, six endogenous normalizing proteins were selected. Owing to considerations of cost, the selection of endogenous normalizing proteins was performed in a label-free approach.

C. Immunoaffinity Chromatography

Experimental protocols for sample preparation were adapted and modified from a recent study (Li, X J. *Sci. Transl. Med.* 2013, 5:207ra142). Immunoaffinity columns containing a 2:1 ratio of IgY14 and SuperMix resins were purchased from Sigma Aldrich (St. Louis). Each column was conditioned with 0.15 M $(NH_4)HCO_3$ at 0.5 ml/min for 45 min. Prior to immunoaffinity separation of each sample batch, column performance was assessed with replicate injections of aliquots of the HPS sample.

To isolate low abundance proteins, 45, 50, or 60 µl of plasma were diluted in 0.15M $(NH_4)HCO_3$ to a final volume of 135, 150, or 180 µl, respectively, and filtered using a 0.45 µm AcroPrep 96-well filter plate (Pall Life Sciences). Immunoaffinity separation was conducted on a IgY14-SuperMix column connected to an high performance liquid chromatography (HPLC) system (Agilent 1260 Infinity Bioinert Quaternary liquid chromatography (LC)) using 3 buffers (loading/washing: 0.15 M $(NH_4)HCO_3$; stripping/elution: 0.1 M glycine, pH 2.5; and neutralization: 0.01 M Tris-HCl and 0.15 M NaCl, pH 7.4) with a cycle comprised of load, wash, elute, neutralization, and re-equilibration lasting 36 min. The total plasma volume loaded onto the depletion column was 15, 20, or 30 µl, respectively. The unbound and bound fractions were monitored at 280 nm and were baseline resolved after separation. Unbound fractions (containing the low abundance proteins) were collected for downstream processing and analysis and lyophilized prior to enzymatic digestion. Every 24 samples were grouped as an experimental batch and were processed sequentially in a throughput of one batch per day.

D. Enzymatic Digestion

Lyophilized fractions containing low abundance proteins were digested with trypsin after being reconstituted under mild denaturing conditions in 200 µl of 1:1 0.1 M $(NH_4)HCO_3$ trifluoroethanol (TFE) (v/v) and then allowed to incubate on an orbital shaker for 30 min at room temperature (RT). Samples were diluted in 800 µl of 0.1 M $(NH_4)HCO_3$ and digested with 0.4 µg trypsin (Princeton Separations) per sample for 16+/−2 hours at 37° C. Following digestion samples were stored at −70° C. for 2 hours and then lyophilized. Samples within each study were digested in parallel.

E. Stable Isotope-labeled Standard Peptides

A total of 26 SIS peptides were purchased from New England Peptide (Gardner, Mass.), including one SIS peptide for each of the six normalizing proteins and the 18 target proteins in Table 1. SIS peptides of two additional proteins (S10A6 and PROF1) were included as potential biomarkers earlier on but were later eliminated. Each SIS peptide was purified to 95% or greater as determined by reversed phase HPLC; mass determination for each peptide was confirmed to be within 0.1% of the calculated mass by matrix-assisted laser desorption/ionization (MALDI)-time of flight (TOF) MS. The concentration of the stock solution for each peptide was determined by amino acid analysis. The SIS peptide mixture was produced per specified formulation in 10% acetonitrile, 0.1% formic acid final concentration with 100 fmol/µL BSA digest added for stability. Concentrations of individual SIS peptides were tailored so that their MRM-MS signal intensities were comparable to those of the corresponding endogenous peptides. The mixture was aliquoted into individual 300 µL single use microfuge tubes and stored at −80° C. Aliquots of the SIS peptide mixture were thawed on wet ice, mixed briefly and spiked into peptide samples after enzymatic digestion and lyophilization and during solubilization just prior to solid-phase extraction. Two different preparations (lots) of the SIS peptide mixture were prepared and used in this study. The stability of SIS peptides was monitored based on their MRM signal intensities. No evidence for the instability of SIS peptides was observed over a period of 20 months (data not shown).

F. Solid-Phase Extraction

Aliquots of the SIS peptide mixture were spiked into the lyophilized peptide samples, followed by reconstitution in 350 µl of 0.01 M (NH$_4$)HCO$_3$, incubation on an orbital shaker for 15 min at RT, reduction using 30 µl of 0.05 M TCEP, incubation for 1 hour at RT, and dilution in 375 µl of 90% water/10% acetonitrile/0.2% trifluoroacetic acid. The solid phase extraction plate (Empore C18, 3M Bioanalytical Technologies) was conditioned according to the manufacturer's protocol, and after sample loading were washed in 500 µl of 95% water/5% acetonitrile/0.1% trifluoroacetic acid and eluted by 200 µl of 52% water/48% acetonitrile/0.1% trifluoroacetic acid into a collection plate. The eluate was split into 2 equal aliquots and was taken to dryness in a vacuum concentrator. One aliquot was used immediately for mass spectrometry, while the other was stored at −80° C. Samples were reconstituted in 12 µl of 90% water/10% acetonitrile/0.2% formic acid just prior to LC-MRM-MS analysis. Samples within each study were processed in parallel in this step.

G. Optimization of MRM Assays

MRM assays of endogenous peptides of the target and normalizing proteins were developed previously on a 5500 QTrap® reversed-phase LC-MRM-MS platform (AB Sciex). The specificity of the assays was verified with a FDR of 3.70% or lower. These assays, along with MRM assays of the corresponding SIS peptides, were transferred to and optimized on a 6490 Triple Quadrupole LC-MRM-MS platform (Agilent) based on the highly purified synthetic SIS peptides. The optimal assays were further tested on processed HPS samples to check for signal intensity and possible interference. Unless specified, the signal of the assays was well above noise and within the respective linear dynamic range. In addition to the low FDRs of the original assays, the specificity of the transitions to the corresponding proteins was further verified from the co-elution of endogenous and SIS peptides and from the consistency between the peptides on intensities of different transitions. Seventeen additional proteins were analyzed for exploratory purposes without optimizing their transitions or spiking in the corresponding SIS peptides. The 17 extra proteins were not analyzed in this study. A total of 302 transitions from 38 proteins were measured in this study.

H. MRM-MS Analysis

Peptide samples were separated using a capillary reversed-phase LC column (Agilent Poroshell 120 EC-C18; 2.1 mm×100 mm, particle size 2.7 µm) and an Agilent 1290 Infinity HPLC system. The mobile phases were (A) 0.1% formic acid in water and (B) 0.1% formic acid in acetonitrile. The samples were injected (8 µl) and separated using a linear gradient (98% A to 70% A) at 0.4 mL/minute for 21.7 min. Peptides were eluted directly into the electrospray source of the mass spectrometer (6490 Triple Quadrupole, Agilent) operating in scheduled MRM positive-ion mode (Q1 resolution: wide; Q3 resolution: unit; detection window variable: 124 to 240 seconds; cycle time: 1.0 seconds). Peak areas of transitions were integrated by MassHunter (Agilent) and manually curated to ensure quality. Samples within each experiment were analyzed sequentially.

I. Four Quantification Methods

In this study the abundance of a protein was evaluated based on the MRM signal intensity of the strongest transition of the protein and no distinctions between protein abundance, peptide abundance and transition abundance were made. Without losing generality, the four quantification methods were described in terms of peptide quantification as follows.

Raw MS data. In this label-free quantification approach, the abundance of peptide p in sample s was measured by its raw peak area ($A_{p,s}$) without normalization.

Endogenous protein normalization (EPN). In this label-free quantification approach, the abundance of peptide p in sample s was measured by its normalized peak area $\tilde{A}_{p,s} = A_{p,s}/S_s^E$, where $S_s^E$ was a sample-dependent normalization factor and was calculated from the peak areas of a predetermined set of N=6 endogenous, normalizing peptides in the sample. More specifically, $$S_s^E = \text{median}\left(\frac{A_{1,s}}{\breve{A}_1}, \frac{A_{2,s}}{\breve{A}_2}, \ldots, \frac{A_{N,s}}{\breve{A}_N}\right) \quad \text{(EQN. 1)}$$

where $A_{p,s}$ was the peak area of peptide normalizer n (with n=1, ..., N) in the sample and $\breve{A}_n$ was a scaling constant for the normalizer that ensured values of $\{A_{n,s}/\breve{A}_n\}$ among all normalizers to be the same on average. The scaling constants $\{\breve{A}_n\}$ were determined as the median values (over all clinical samples) of $\{A_{n,s}\}$ in an independent study of 120 samples.

Quantification using SIS peptides (SISQuan). In this labeled quantification approach, the abundance of peptide p in sample s was measured by the response ratio between the endogenous peptide to the corresponding SIS peptide, that is $R_{p,s} = A_{p,s}/\hat{A}_{p,s}$ where $\hat{A}_{p,s}$ was the peak area of the SIS peptide.

Integrated quantification (InteQuan). In this labeled quantification approach, the abundance of peptide p in sample s was measured by its normalized response ratio $\tilde{R}_{p,s} = R_{p,s}/S_s^I$, where $S_s^I$ was a sample-dependent normalization factor and was calculated from the response ratios of the N peptide normalizers in the sample. More specifically, $$S_s^I = \text{median}\left(\frac{R_{1,s}}{\breve{R}_1}, \frac{R_{2,s}}{\breve{R}_2}, \ldots, \frac{R_{N,s}}{\breve{R}_N}\right) \quad \text{(EQN. 2)}$$

where $R_{n,s}$ was the response ratio of peptide normalizer n in the sample and $\breve{R}_n$ was a scaling constant for the normalizer that ensured values of $\{R_{n,s}/\breve{R}_n\}$ among all normalizers to be same on average. Similar to $\{\breve{A}_n\}$, the scaling constants $\{\breve{R}_n\}$ were determined as the median values (over all clinical samples) of $\{R_{n,s}\}$ in the same study of 120 samples.

J. Migration to new lot of SIS peptides

Six aliquots of the HPS sample (30 µl per aliquot) were processed and pooled together after digestion. The pooled sample was split into two identical aliquots. Two lots of SIS peptide mixtures (old and new) were each spiked into one of the two aliquots of HPS. The two aliquots of SIS peptide/HPS mixture were then each further split into three equal aliquots and lyophilized. The SIS peptide/HPS mixtures were reconstituted, desalted, lyophilized, and stored. The SIS peptide/HPS samples were then solubilized and analyzed by MRM-MS. A correction factor was calculated for each peptide as $F_p = \hat{R}_{p,old}/\hat{R}_{p,new}$, where $\hat{R}_{p,old}(\hat{R}_{p,new})$ was the median response ratio of peptide p as evaluated using the old (new) lot of SIS peptides. In Study II, the abundance ratio $R'_{p,s}$ of peptide p in sample s as measured using the new lot was multiplied by the correction factor $F_p$, that is $R_{p,s} = R'_{p,s} * F_p$. This correction was applied to both the target and the normalizing peptides. Afterwards, the evaluation of protein abundance using InteQuan and using SISQuan were both based on the corrected abundance ratios $\{R_{p,s}\}$.

N. Differences Between Study I and a Previous Study

All clinical samples in Study I have been previously processed and analyzed by a contract research organization (CRO; Caprion, Montreal). Similar protocols were used in immunoaffinity depletion, protein digestion and desalting (Li, X J et al, *Sci. Tranl. Med.* 2013, 5:207ra142). Major differences between the two studies included: 1) Laboratory: Study I was carried out in-house but the discovery study was done by the CRO. 2) Depletion: The depletion column was ordered directly from vendor in Study I but packed by the CRO with a different lot of IgY14-Supermix resin beads in the discovery study. 3) Quantification: SIS peptides were used for quantification in Study I but not in the discovery study. 4) MS platform: Peptides were analyzed by an Agilent 6490 Triple Quadrupole LC/MS System in Study I but by an AB SCIEX QTrap® 5500 LC/MS system in the discovery study. 5) Monitored transitions: 302 transitions of 38 proteins were monitored in Study I. In comparison, 1550 transitions of 344 proteins were monitored in the discovery study.

O. Statistical Data Analysis

Data analysis was performed using the R statistical environment. Code for PVCA was adapted from: [http://www.niehs.nih.gov/research/resources/software/biostatist-ics/pvca/], setting the threshold to capture at least 90% of variance and a minimum of two principal components. The p value for comparing different quantification methods was based on the most-applicable, non-parametric paired sign test, assuming that measurements were independent and from a continuous population. The p value was evaluated using the function "SIGN.test" in the "BSDA" library. Functions "glm" and "predict" were used to train and test logistic regression models. Function "lm.fit" in the "stats" library was used to fit the linear relationship between the SISQuan abundances and the sample loading volumes.

Example 2

Demonstration of Complementary Control of Variation by SISQuan and EPN

In Study I, 60 clinical samples and 12 aliquots of the HPS sample were analyzed in three experimental batches using one depletion column (FIG. 1C and Table 2). Clinical information of the patients is listed in Table 3. MRM-MS data was successfully collected on 55 clinical samples and 10 HPS samples while seven samples were lost during processing (Table 2). The normalization factors of the six normalizing proteins had a median coefficient of variation (CV) of 20.4% as evaluated from individual samples in the study.

TABLE 3

Clinical information of patients in Study I

| Subject | Disease Status | Cancer Stage | Histopathology of Cancer | Gender | Age | Nodule Size (mm) | Smoking Status | Pack-Year |
|---|---|---|---|---|---|---|---|---|
| S1 | Benign | | | Male | 69 | 33 | Past | 98 |
| S2 | Cancer | I | ADENOCARCINOMA w/MIXED | Male | 71 | 6 | Past | 25 |
| S3 | Cancer | I | SQUAMOUS | Male | 53 | 45 | Past | 114 |
| S4 | Benign | | | Male | 56 | 26 | Past | 10 |
| S5 | Benign | | | Female | 63 | 35 | Never | 0 |
| S6 | Cancer | I | ADENOCARCINOMA | Female | 64 | 39 | Past | 7.5 |
| S7 | Benign | | | Male | 67 | 47.5 | Current | 55 |
| S8 | Cancer | II | SQUAMOUS | Male | 72 | 43 | Past | 48 |
| S9 | Benign | | | Male | 58 | 25 | Current | 40 |
| S10 | Cancer | I | ADENOCARCINOMA | Male | 57 | 30 | Past | 40 |
| S11 | Cancer | I | ADENOCARCINOMA | Male | 61 | 36 | Past | 20 |
| S12 | Benign | | | Male | 55 | 22 | Past | 15 |
| S13 | Benign | | | Female | 52 | 43 | Never | 0 |
| S14 | Benign | | | Female | 46 | 40 | Current | 30 |
| S15 | Benign | | | Male | 52 | 38 | Past | 9 |
| S16 | Cancer | II | MIXED | Male | 48 | 40 | Current | 35 |
| S17 | Benign | | | Male | 64 | 32 | Past | 12 |
| S18 | Cancer | II | SQUAMOUS | Male | 62 | 24 | Current | 92 |
| S19 | Cancer | I | SQUAMOUS | Male | 73 | 32 | Past | 130 |
| S20 | Benign | | | Male | 74 | 22 | Never | 0 |
| S21 | Cancer | II | ADENOCARCINOMA | Female | 67 | 40 | Past | 40 |
| S22 | Benign | | | Female | 66 | 40 | Never | 0 |
| S23 | Cancer | I | ADENOCARCINOMA | Male | 60 | 12 | Past | 17.5 |
| S24 | Benign | | | Male | 62 | 40 | Past | NA |
| S25 | Benign | | | Female | 76 | 40 | Never | 0 |
| S26 | Cancer | II | ADENOCARCINOMA | Female | 75 | 44 | Past | 58 |
| S27 | Benign | | | Female | 62 | 23 | Past | NA |
| S28 | Cancer | I | ADENOCARCINOMA | Female | 58 | 22 | Current | 19 |
| S29 | Benign | | | Male | 43 | 56 | Current | 30 |
| S30 | Cancer | II | SQUAMOUS | Male | 51 | 58 | Past | 95 |
| S31 | Benign | | | Male | 77 | 26 | NA | 45.6 |
| S32 | Cancer | I | ADENOCARCINOMA | Male | 75 | 9 | Past | 91.5 |
| S33 | Cancer | II | ADENOCARCINOMA | Male | 79 | 50 | Past | 12.5 |
| S34 | Benign | | | Male | 78 | 48 | Past | NA |
| S35 | Cancer | II | NA | Female | 56 | 24 | Past | 36 |
| S36 | Benign | | | Female | 59 | 24 | Past | 47.5 |
| S37 | Benign | | | Female | 64 | 26 | Never | 0 |

TABLE 3-continued

Clinical information of patients in Study I

| Subject | Disease Status | Cancer Stage | Histopathology of Cancer | Gender | Age | Nodule Size (mm) | Smoking Status | Pack-Year |
|---|---|---|---|---|---|---|---|---|
| S38 | Cancer | I | ADENOCARCINOMA | Female | 64 | 33 | Never | 0 |
| S39 | Benign | | | Female | 53 | 54 | Past | 30 |
| S40 | Cancer | II | ADENOCARCINOMA | Female | 72 | 32 | Current | 50 |
| S41 | Benign | | | Female | 61 | 35 | Past | 25 |
| S42 | Cancer | II | ADENOCARCINOMA w/MIXED | Female | 60 | 25 | Current | 90 |
| S43 | Benign | | | Female | 38 | 22 | Never | 0 |
| S44 | Cancer | II | ADENOCARCINOMA | Female | 75 | 45 | Current | 12.5 |
| S45 | Benign | | | Male | 65 | 24 | Past | 30 |
| S46 | Cancer | I | ADENOCARCINOMA | Male | 64 | 50 | Past | NA |
| S47 | Cancer | II | SQUAMOUS | Female | 47 | 55 | Never | 0 |
| S48 | Benign | | | Female | 52 | 24 | Past | 15 |
| S49 | Cancer | IIA | SQUAMOUS | Male | 82 | 34 | Past | 30 |
| S50 | Benign | | | Male | 84 | 32 | Past | 30 |
| S51 | Cancer | II | SQUAMOUS | Female | 63 | 47 | Past | 15 |
| S52 | Benign | | | Male | 44 | 45 | Past | 30 |
| S53 | Benign | | | Male | 41 | 31 | Past | 20 |
| S54 | Cancer | II | ADENOCARCINOMA | Male | 51 | 35 | Past | 30 |
| S55 | Cancer | II | SQUAMOUS | Female | 67 | 52 | Current | NA |
| S56 | Benign | | | Female | 65 | 42 | Never | 0 |
| S57 | Benign | | | Female | 54 | 5 | Past | 20 |
| S58 | Cancer | II | ADENOCARCINOMA w/MIXED | Female | 67 | 44 | Past | 30 |
| S59 | Benign | | | Female | 60 | 41 | Current | 40 |
| S60 | Cancer | II | ADENOCARCINOMA | Female | 61 | 27 | Past | 40 |

Figure 3:
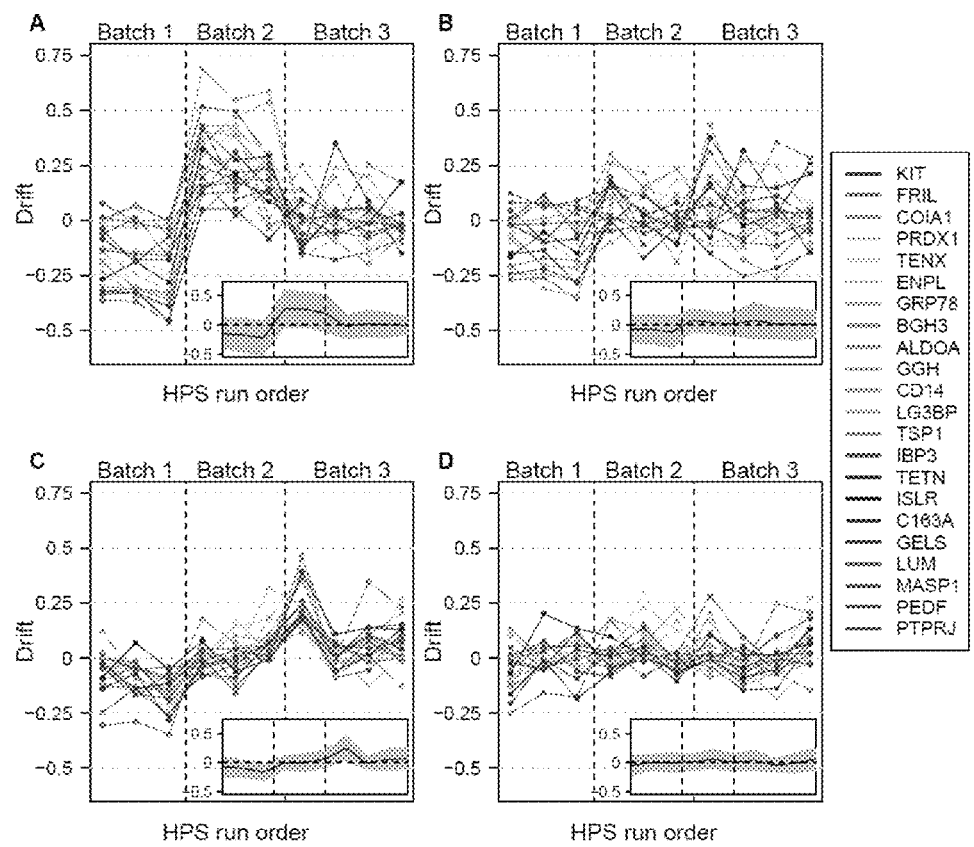
FIG. 3 is a set of graphs showing intensity drift of 16 target proteins and the six normalizing proteins as measured on 10 HPS samples in Study I described in the Examples. Results are shown in different panels for (A) raw MS data, (B) EPN, (C) SISQuan, and (D) InteQuan. The insert in panels (A)-(D) shows the mean (solid line) and 95% confidence internal (shaded band) of the protein drifts.

To understand how SISQuan and EPN controlled technical variability, intensity drift was defined as the relative deviation of protein intensity in individual samples from the corresponding median intensity in all samples, and was evaluated based on data of the 10 HPS samples (FIG. 3), using the four quantification methods. Since the 10 HPS samples were identical, the deviation of protein drifts from zero represented the analytical variability in the experiment. The mean of protein drifts, plotted as a solid line in the inserts of FIG. 3, measured the strength of variation that affected all proteins similarly (i.e., the strength of systematic variation). The 95% confidence interval (CI) of protein drifts, plotted as a shaded band in the inserts of FIG. 3, measured the strength of variation that affected different proteins differently (i.e., the strength of protein-specific variation). In comparison with the protein drifts for the raw MS data (FIG. 3A), the protein drifts for EPN had a lower absolute mean but a comparable 95% CI (FIG. 3B) while the protein drifts for SISQuan had a lower 95% CI but a comparable absolute mean (FIG. 3C). Thus, EPN effectively controlled systematic variation and SISQuan effectively controlled protein-specific variation, illustrating the complementary nature of the two methods. The protein drifts for InteQuan had a lower absolute mean and a lower 95% CI (FIG. 3D), illustrating that InteQuan suppressed both systematic and protein-specific variation.

A. Intensity Drift

The intensity drift of peptide p in sample s was defined as $$D_{p,s} = (I_{p,s} + \check{I}_p)/\check{I}_p \quad \text{(EQN. 3)}$$

where $I_{p,s}$ was the abundance of the peptide in the sample and $\check{I}_p$ was the corresponding median value in all technical replica. The intensity drift $D_{p,s}$ evaluated how far the abundance of the peptide in the sample deviated from the overall median abundance of the peptide. The median value of $D_{p,s}$ was zero by definition for all peptides.

Example 3

Improvement on Precision of Protein Measurement

To assess the precision of InteQuan and SISQuan, CVs of the target proteins were evaluated from the 10 HPS samples (Table 4). InteQuan had better precision than SISQuan on all proteins except for ISLR. The median CV of all proteins was 9.3% using InteQuan versus 13.3% using SISQuan. InteQuan was statistically more precise than SISQuan (P=5.2× $10^{-4}$) and lowered protein CV by a median value of 4.9%. Using InteQuan, the highest CV was 16.8% (FRIL, 12 ng/ml). CVs of the remaining 15 target proteins were all below 15%, including 10 proteins with a CV below 10% and two proteins with a CV at or below 5%.

TABLE 4

Coefficient of variation (CV) of protein abundance as evaluated using InteQuan and using SISQuan

| | Study I CV (%) | | Study II CV (%) | | Study III CV (%) | |
|---|---|---|---|---|---|---|
| Protein | InteQuan | SISQuan | InteQuan | SISQuan | InteQuan | SISQuan |
| KIT | 8.8 | 9.6 | 4.3 | 10.5 | 7.8 | 35.0 |
| FRIL | 16.8 | 25.2 | 5.3 | 11.8 | 7.3 | 33.6 |
| COIA1 | 12.6 | 17.8 | 9.0 | 9.7 | 10.4 | 38.5 |

TABLE 4-continued

Coefficient of variation (CV) of protein abundance as evaluated using InteQuan and using SISQuan

| Protein | | | | | | |
|---|---|---|---|---|---|---|
| PRDX1 | 10.7 | 15.4 | 4.9 | 11.8 | 9.6 | 32.2 |
| TENX | 11.1 | 13.6 | 8.8 | 12.7 | 10.7 | 26.6 |
| ENPL | 13.1 | 18.9 | 11.2 | 8.6 | 11.3 | 34.9 |
| GRP78 | 6.8 | 11.4 | 19.3 | 24.2 | 11.5 | 33.7 |
| BGH3 | 5.0 | 12.3 | 5.7 | 9.9 | 12.4 | 42.3 |
| ALDOA | 6.6 | 13.6 | 9.1 | 17.5 | 15.1 | 35.4 |
| GGH | 6.9 | 7.1 | 9.0 | 13.7 | 13.9 | 38.9 |
| CD14 | 4.1 | 8.0 | 4.6 | 12.0 | 4.6 | 35.3 |
| LG3BP | 8.8 | 13.0 | 5.9 | 10.0 | 5.6 | 31.1 |
| TSP1 | 11.6 | 18.3 | 12.9 | 17.0 | 21.5 | 45.7 |
| IBP3 | 5.7 | 11.6 | 6.3 | 13.5 | 13.5 | 41.5 |
| TETN | 9.9 | 17.8 | 9.9 | 12.4 | 25.5 | 52.3 |
| ISLR | 10.0 | 9.1 | 4.7 | 10.0 | 4.2 | 31.3 |
| Median CV (%) | 9.3 | 13.3 | 7.6 | 11.9 | 11.0 | 35.1 |
| Median of CV reduction[a] (%) | 4.9 | | 4.8 | | 25.9 | |
| Total proteins with lower CV | 15 | 1 | 15 | 1 | 16 | 0 |
| P value (paired sign test) | $5.2 \times 10^{-4}$ | | $5.2 \times 10^{-5}$ | | $3.1 \times 10^{-4}$ | |
| Comments | CV of 10 HPS aliquots | | Median CV of 15 clinical samples | | Median CV of 6 samples | |

| | Study III | | Combined HPS dataset | | | |
|---|---|---|---|---|---|---|
| | Generalized CV (%) | | CV (%) | | Generalized CV (%) | |
| Protein | InteQuan | SISQuan | InteQuan | SISQuan | InteQuan | SISQuan |
| KIT | 7.7 | 6.5 | 10.5 | 31.7 | 10.6 | 12.8 |
| FRIL | 7.3 | 12.0 | 15.9 | 25.4 | 16.7 | 18.8 |
| COIA1 | 10.2 | 14.1 | 16.1 | 31.1 | 16.6 | 17.5 |
| PRDX1 | 9.4 | 14.6 | 31.9 | 15.8 | 31.8 | 15.5 |
| TENX | 10.8 | 11.1 | 10.7 | 32.3 | 10.6 | 15.2 |
| ENPL | 11.3 | 13.6 | 11.7 | 32.9 | 11.8 | 12.6 |
| GRP78 | 11.2 | 12.9 | 13.9 | 28.5 | 13.6 | 18.4 |
| BGH3 | 12.4 | 13.8 | 9.8 | 33.7 | 9.6 | 14.9 |
| ALDOA | 14.9 | 19.9 | 11.0 | 35.4 | 11.2 | 14.9 |
| GGH | 13.7 | 16.5 | 11.0 | 31.7 | 10.5 | 16.6 |
| CD14 | 4.7 | 6.8 | 7.9 | 30.5 | 7.8 | 11.9 |
| LG3BP | 5.6 | 7.5 | 8.6 | 30.5 | 8.5 | 13.9 |
| TSP1 | 20.9 | 21.9 | 20.3 | 41.1 | 22.9 | 25.3 |
| IBP3 | 14.0 | 15.5 | 19.8 | 26.7 | 20.5 | 21.6 |
| TETN | 26.9 | 29.7 | 33.1 | 47.6 | 33.3 | 37.7 |
| ISLR | 4.2 | 5.0 | 12.2 | 33.8 | 12.1 | 9.6 |
| Median CV (%) | 11.0 | 13.7 | 11.9 | 31.7 | 11.9 | 15.3 |
| Median of CV reduction[a] (%) | 2.0 | | 21.0 | | 3.0 | |
| Total proteins with lower CV | 15 | 1 | 15 | 1 | 14 | 2 |
| P value (paired sign test) | $5.2 \times 10^{-4}$ | | $5.2 \times 10^{-4}$ | | $4.2 \times 10^{-3}$ | |
| Comments | Median CV of 6 samples | | CV of 29 HPS aliquots | | | |

[a] CV reduction was defined as CV using SISQuan minus CV using InteQuan.

Example 4

Improvement on Panel Performance in Disease Diagnosis

Figure 4:
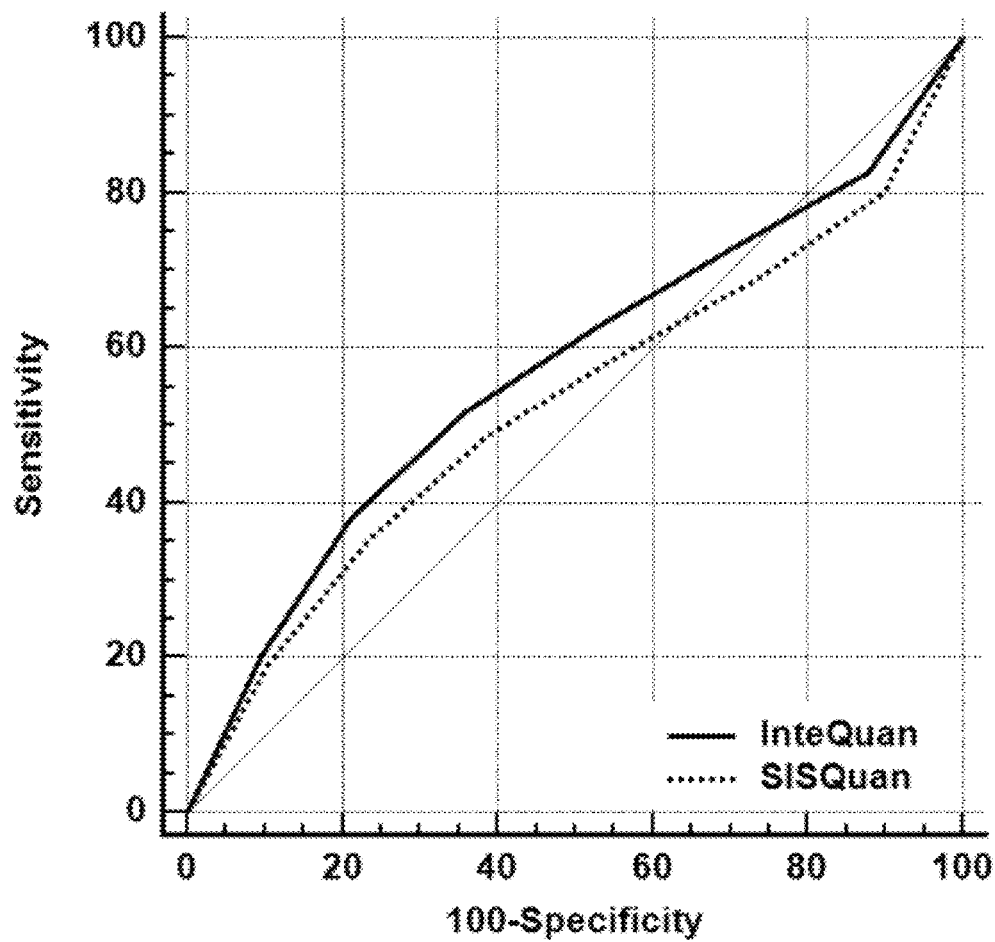
FIG. 4 is a graph showing receiver operating characteristic curves of the panel of all 16 target proteins, evaluated with Monte Carlo cross validation (MCCV) on clinical samples in Study I described in the Examples. Proteins are quantified using InteQuan (solid line) or SISQuan (dotted line).

To illustrate the benefit of using InteQuan in clinical applications, a protein panel was constructed of all 16 target proteins and tested on the clinical samples in Study I using Monte Carlo cross validation (MCCV). Since the sample size was very small, the panel was not optimized for intended use, owing to concerns on both high false positive rate and high false negative rate. Using either InteQuan or SISQuan, the performance of the panel was summarized by the two receiver operating characteristic (ROC) curves in FIG. 4. The corresponding AUC was 0.573 (95% CI 0.569-0.576) using InteQuan or 0.528 (95% CI 0.524-0.532) using SISQuan, respectively. The improvement by InteQuan was 0.045 (95% CI 0.042-0.048, P<0.0001). Thus, the panel had a significantly better performance using InteQuan than using SISQuan. More importantly, the ROC curve using InteQuan was consistently better than the ROC curve using SISQuan everywhere: See FIG. 4. This comparative analysis demonstrated that InteQuan improved the performance of the 16-protein panel in disease diagnosis, illustrating its value for biomarker research, despite the fact that the panel was not optimized for clinical application. A protein panel comprising a subset of the 16 target proteins was recently optimized and validated using the InteQuan quantification method (Vachani et al., Validation of a Multi-Protein Plasma Classifier to Identify Benign Lung Nodules, J. of Thoracic. Onc. (doi: 10.1097/JTO.0000000000000447)).

A. Monte Carlo Cross Validation

Monte Carlo cross validation (MCCV) was performed as follows: First, all clinical samples in Study I were randomly assigned to a training group (including 24 benign and 24 cancer samples) or a test group (including 4 benign and 3 cancer samples). Second, two logistic regression models were developed to fit the disease status of the training samples, using either the InteQuan abundances or the SISQuan abundances of all 16 proteins in Table 4 as predictors. The first two steps were repeated if any one of the two models failed to converge. Third, the models were used to calculate scores of the test samples, evaluating their likelihood of being a cancer sample, based on protein InteQuan or SISQuan abundances, respectively. Fourth, the test samples were ranked by their scores from the InteQuan model or the SISQuan model, respectively. Fifth, the first four steps were repeated 10,000 times with different sample permutations. The ranking and the corresponding disease status of the test samples in all permutations were assembled under either InteQuan or SISQuan, respectively. Finally, comparison of ROC curves was carried out to compare the MCCV performance of the 16-protein panel using InteQuan with the corresponding performance using SISQuan. Due to small sample size, covariates in both the training samples and the test samples were unavoidable and difficult to adjust, which made it not meaningful to direct compare scores of the test samples between different permutations. Thus, the ranking instead of the score was combined for the ROC analysis, which effectively standardized the scores between different permutations. The ROC comparison analysis was performed by MedCalc (Ostend, Belgium), selecting "DeLong et al." and "Binomial exact Confidence Interval for the AUC" as options.

Example 5

Better Control of Analytical Variability

To determine whether InteQuan can better control analytical variability during use of multiple depletion columns on clinical samples, 18 clinical samples in triplicate along with 12 aliquots of the HPS sample were analyzed in three experimental batches using three depletion columns in Study II (FIG. 1C and Table 2). The three aliquots of the clinical samples were processed either using different depletion columns or using the same column but at different positions in the depletion sequence, monitoring analytical variability due to column or position difference. Out of the 66 samples, an HPS sample and three clinical samples were lost during processing (Table 2). A new lot of SIS peptide mixture was used in this study. The correction factors between the new and the old lots of SIS peptide mixture were determined from a migration experiment and are listed in Table 1. This dataset to compare different quantification methods.

The median CVs of the target proteins were evaluated from the 15 clinical samples having three replicate measurements (Table 4). InteQuan demonstrated better precision than SISQuan on all proteins except for ENPL. The median CV of all proteins was 7.6% using InteQuan versus 11.9% using SISQuan. InteQuan was statistically more precise than SISQuan ($P=5.2\times10^{-4}$) and lowered protein CV by a median value of 4.8%. Using InteQuan, the highest CV was 19.3% (GRP78, 100 ng/ml). CVs of the remaining 15 target proteins were all below 15%, including 13 proteins with a CV below 10% and four proteins with a CV below 5%.

Figure 5:
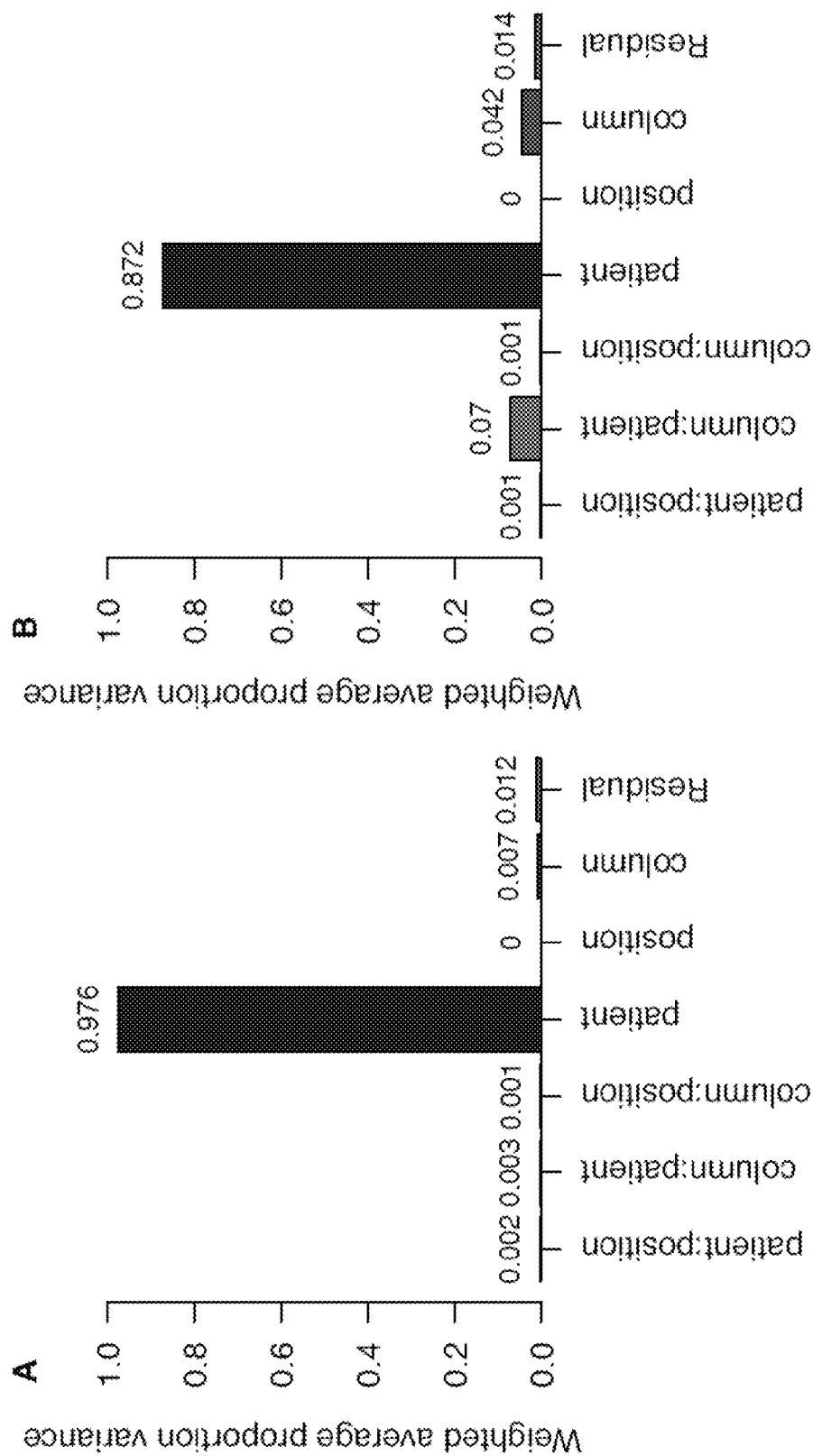
FIG. 5 is a pair of charts showing principal variance component analysis (PVCA) of protein abundance in 15 clinical samples having three replicate measurements as described in the Examples. Protein abundance is shown in using (A) InteQuan and (B) SISQuan.

To assess whether InteQuan can better control analytical variability without compromising its ability to reveal biological difference among the clinical samples, principal variance component analysis (PVCA) was carried out to identify the major sources of variation in the experiment, including biological variation among individual patients (denoted as "patient"), analytical variation among depletion columns (denoted as "column"), and analytical variation among positions within a depletion sequence (denoted as "position") (FIG. 5). For InteQuan, "patient" alone contributed 97.6% to the total variability while other sources jointly contributed a negligible fraction of 2.4%. For SISQuan, "patient" alone contributed 87.2% to the total variability while other sources jointly contributed 12.8%. Thus, InteQuan enhanced the ability of measuring biological difference among the clinical samples, in agreement with the previous observation that InteQuan improved the performance of the 16-protein panel in Study I. In other words, InteQuan improved the resolution of protein measurement in clinical samples.

Example 6

High Tolerance Against Variation in Total Protein Concentration

Figure 6:
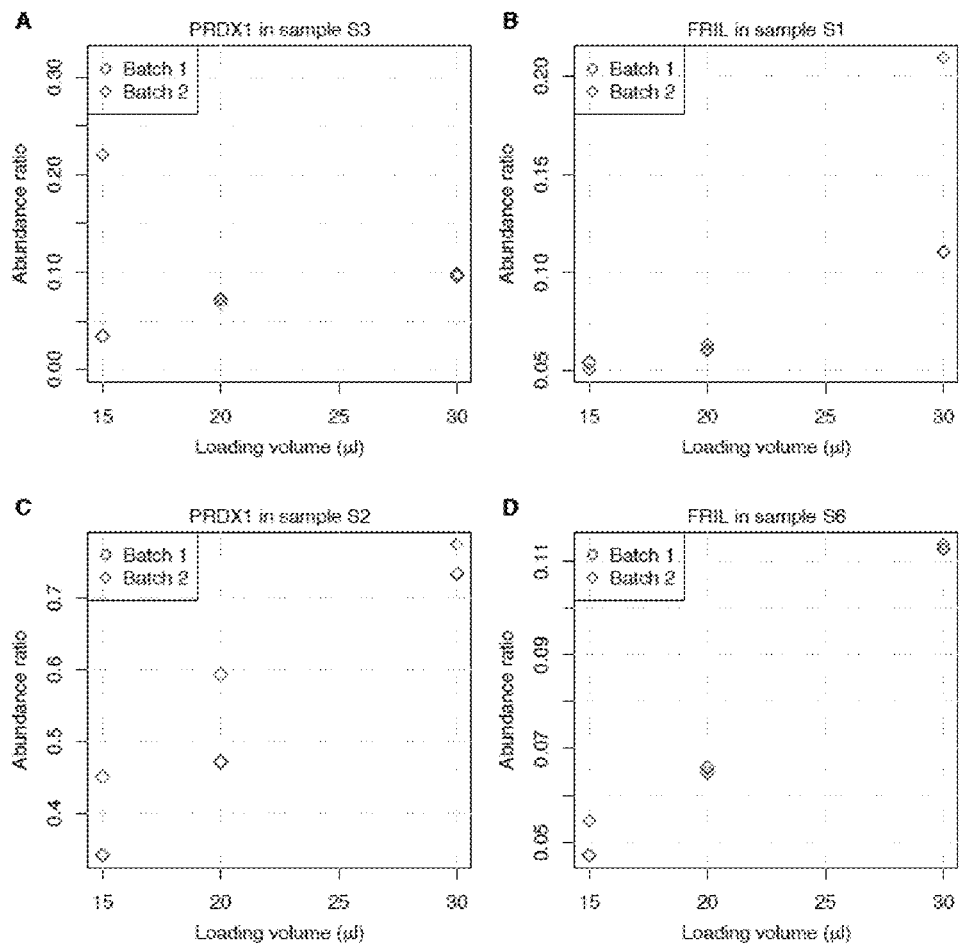
FIG. 6 is a set of graphs showing examples of SISQuan abundance versus loading volume in Study III. The top row shows two outlier measurements while the bottom row shows the corresponding linear behavior of the same proteins. Panel (A) shows PRDX1 in sample S3. The outlier measurement (Batch 2 with the loading volume of 15 μl) was removed from analysis. Panel (B) shows FRIL in sample S1. The outlier measurement (Batch 2 with the loading volume of 30 μl) was removed from analysis. Panel (C) shows PRDX1 in sample S2. Panel (D) shows FRIL in sample S6.

To demonstrate InteQuan's ability to handle the variation in the total protein concentration, six samples were diluted into three concentrations (equivalent to the loading of 15, 20, or 30 μl of the original plasma samples: see Example 1, C.) and analyzed in duplicate using two depletion columns along with eight aliquots of the HPS sample in Study III (FIG. 1C and Table 2). No data was collected on one of the 44 samples owing to sample exhaustion. Manual review of experimental data identified two erratic measurements (FIG. 6A, B) that were eliminated from further analysis.

The median CVs of the target proteins were evaluated from the six samples using all valid measurements (Table 4). The median CV of all proteins was 11.0% using InteQuan and 35.1% using SISQuan. As a reference, the CV evaluated from the equivalent loading volumes (duplicates of 15, 20, and 30 µl) was 31.5%. While the median CV using SISQuan was higher than the CV of the loading volume, the median CV using InteQuan was much lower. Using InteQuan, all proteins had a median CV less than 20% except for TETN (25.5%) and TSP1 (21.5%), despite a two-fold difference in the total protein concentration.

Example 7

Usage of Generalized CV for Precision Evaluation in Study III

The high CVs of the target proteins using SISQuan in Study III reflected the large difference in the total protein concentration (FIG. 6) rather than the precision of SISQuan. To compare the precision of InteQuan and SISQuan, a generalized method for CV calculation was developed. This method included two steps: First, the abundance of proteins in a sample was modeled either as linear functions of the loading volume (SISQuan) or as constants independent of the loading volume (InteQuan). Second, error propagation theory was applied to calculate the generalized CV as the standard deviation of differences between the modeled and the experimental abundances after logarithmic transformation. The modeled and the experimental abundances of all proteins in all samples collapsed nicely onto the respective diagonal line in FIGS. 7A and B, indicating that the method worked very well for both InteQuan and SISQuan. For SISQuan, it also demonstrated that proteins were measured within the respective linear dynamic range of the assays at all three concentrations. The generalized CVs and the standard CVs of InteQuan abundance were almost identical for all proteins in all samples (FIG. 7C). On the contrary, the generalized CVs of SISQuan abundance were uniformly lower than the corresponding standard CVs (FIG. 7D).

The median generalized CVs of the target proteins were evaluated from the six samples using all valid measurements (Table 4). InteQuan demonstrated better precision than SISQuan on all proteins except for KIT. The median generalized CV of all proteins was 11.0% using InteQuan versus 13.7% using SISQuan. InteQuan was statistically more precise than SISQuan (P=5.2×10$^{-4}$) and lowered protein generalized CV by a median value of 2.0%.

The generalized CV can be applied to analyze data from dilution experiments within the linear dynamic range and to provide an assessment on precision over the whole concentration range. Ideally, generalized CV should be evaluated on data covering three or more concentrations to avoid over-fitting.

A. Calculation of Generalized CV
The method consisted of two steps:
In the first step, protein InteQuan abundances in a sample were modeled as constants independent of the loading volume. Thus, the expected InteQuan abundances were assigned to the corresponding average values, that is $$\tilde{R}_{p,s}^I = \frac{1}{N_{p,s}} \sum_{i=1}^{N_{p,s}} \tilde{R}_{p,s,i}. \quad \text{(EQN. 4)}$$

Here $\tilde{R}_{p,s,i}$ was the InteQuan abundance of protein p in sample s at the loading volume $v_i$=15, 20, or 30 and $N_{p,s}$ was the number of repeat measurements of the protein on the sample regardless of the loading volumes, that is $N_{p,s}$=5 or 6 in Study III and $N_{p,s}$=29 for the combined HPS dataset.

On the contrary, protein SISQuan abundances in a sample were modeled as linear functions of the loading volume. More specifically, the expected SISQuan abundances were fitted as linear functions of the loading volume such that $$R_{p,s,i}^S = a_{p,s} * v_i + b_p. \quad \text{(EQN. 5)}$$

Here $a_{p,s}$ was proportional to the concentration of the protein in the sample and $b_p$ was common to all samples. Parameters $\{a_{p,s}\}$ and $b_p$ were evaluated from repeat measurements of the protein in all samples using maximum likelihood estimation. Ideally one should have at least three loading volumes to avoid over-fitting.

In the second step, error propagation theory was applied to evaluate the generalized CV. According to the theory, the CV of a quantity equals to the standard deviation of the same quantity after logarithmic transformation, that is $$CV(x) = \frac{\sigma(x)}{x} = \sigma(\ln(x))$$

where $\sigma(x)$ represents the standard deviation of x and ln(x) is the natural logarithmic function. Thus, the generalized CV of protein abundance was evaluated from differences between the expected and the experimental values after logarithmic transformation. More specifically, the generalized CV of InteQuan abundance was evaluated as:

$$CV_{p,s}^I = \sqrt{\frac{\sum_{i=1}^{N_{p,s}} \left[\ln(\tilde{R}_{p,s,i}) - \ln(\tilde{R}_{p,s}^I)\right]^2}{N_{p,s} - 1}}. \quad \text{(EQN. 6)}$$

And the generalized CV of SISQuan abundance was evaluated as:

$$CV_{p,s}^S = \sqrt{\frac{\sum_{i=1}^{N_{p,s}} \left[\ln(R_{p,s,i}) - \ln(R_{p,s,i}^S)\right]^2}{N_{p,s} - 1 - 1/K}}. \quad \text{(EQN. 7)}$$

Here K was the number of different samples used in the study and was needed to account for the fitting of $b_p$. Thus, K=6 in Study III and K=1 for the combined HPS dataset.

Example 8

Robustness of the Depletion-MRM-MS Platform

The three assessment studies lasted over six months, were carried out by different operators, encountered major instrument repairs, required implementation of a protocol change in sample loading volume, and used different reagent lots (Table 5).

TABLE 5

Summary of main experimental differences among the three assessment studies and major instrument services

| Procedure | Description | Study I | Study III | Study II |
|---|---|---|---|---|
| Depletion | Date | 18-21 Nov 2012 | 21-23 Feb 2013 | 15-17 Apr 2013 |
| | Operator | JM | JM | JM |
| | Column lot | 20093648 | 20093648 & SLBD7383 | 3315179 |
| | HPLC machine | HPLC-LC00001 | HPLC-LC00001 | HPLC-LC-00001: Batch 1 & 2 HPLC-LC-00002: Batch 3 |
| | HPLC service[a] | 18 Nov 2012 | 20 & 22 Feb 2013 | HPLC-LC00001: 26, 28 & 29 Mar; 15 & 17 Apr 2013 HPLC-LC00002: 17 Apr 2013 |
| Digestion | Date | 26-27 Nov 2012 | 28 Feb-01 Mar 2013 | 23-24 Apr 2013 |
| | Operator | DAS | JM | DAS/JM |
| Solid-phase extraction | Date | 3-4 Dec 2012 | 03-04 Mar 2013 | 25-26 Apr 2013 |
| | Operator | DAS | JM | DAS/JM |
| MS analysis | Date | 11 Dec 2012-9 Jan 2013 | 6-10 Mar 2013 | 29 Apr-5 May 2013 |
| | Operator | JT | DAS | DAS |
| | SIS lot | Lot 1 | Lot 1 | Lot 2 |
| | RP column lot | Not Recorded | S/N USCGC02709 | S/N USCGC02348 |
| | RP HPLC service in Year 2013 | HPLC Flush (17 Jan), analytical column change (14 Feb 21 & 25 Mar), B side check valve replaced (15 Feb), A side pump head replaced (19 Feb), B side pump head replaced (4 Mar), and PM service on LC unit (11 Mar). | | |
| | MS service | Hexa bore capillary change (18 Dec 2012, 6 Feb 2013, 4 Mar 2013) and Ion funnels cleaned & PM on MS (11 Mar 2013). | | |
| | Data curation | JT | DAS | DAS |

[a]Changed depletion column, purge valve frit, 2 inline filters, and needle seat.

To assess the robustness of the depletion-MRM-MS platform, the CVs and the generalized CVs of the target proteins were computed from the 29 HPS samples across all three studies (FIG. 7E-H and Table 4). Using InteQuan, 13 of the 16 target proteins had a CV less than 20%, 10 had a CV less than 15%, and three had a CV less than 10%. Only three proteins had a CV greater than 20%, including TSP1 with a CV of 20.3%, PRDX1 with a CV of 31.9%, and TETN with a CV of 33.1%.

We investigated possible causes for the high CVs of PRDX1 and TETN. On PRDX1, we noticed that, despite a lower loading volume per sample in Study II that was only two thirds of the loading volume in the other two studies, its SISQuan abundance was almost the same in all three studies. As a result, its InteQuan abundance was about 77% higher in Study II than in the other two studies, which led to the large CV value, The CV of its EPN abundance was only 16.7% Thus, the large CV of its InteQuan abundance was likely due to issues on isotopic labeling rather than protein normalization. Possible causes for the inflated PRDX1 abundance in Study II include: (i) the correction factor for PRDX1 in Table 1 was incorrectly determined and/or (ii) the SIS peptide of QITVNDLPVGR (SEQ ID NO: 36) of PRDX1. was partially cyclized [31]in Study II. On TETN, we noticed that the generalized CV of its SISQuan abundance was even higher at 37.7%. It turns out that TETN partially binds to the IgY14-Supermix resin column [25]. Possible causes for the large CV of TETN include: (i) the binding affinity varied between different depletion columns and/or (ii) the binding affinity was sensitive to the loading volume. In both cases InieQuan, as a quantification method itself, was not the cause for the high CV values.

Based on generalized CV, InteQuan had better precision than SISQuan on all proteins except for PRDX1 and ISLR. The median generalized CV of all proteins was 11.9% using InteQuan versus 15.3% using SISQuan. The generalized CV likely overestimated the precision of SISQuan since linear functions were used to fit SISQuan abundances at only two different protein concentrations, instead of the desirable three or more concentrations to avoid over-fitting. Nevertheless, InteQuan was statistically more precise than SISQuan ($P=4.2 \times 10^{-3}$) and lowered protein generalized CV by a median value of 3.0%. Based on standard CV, the superiority of InteQuan to SISQuan was even more significant ($P=5.2 \times 10^{-4}$).

Example 9

Evaluation of Alternative Normalizing Panels

To assess whether a subset of the six normalizing proteins can form a normalization panel that is better than the full panel, all combinations of the six normalizing proteins were used to quantify the target proteins using InteQuan on the combined HPS dataset (FIG. 8A). The "best" panel, selected on the basis that the corresponding median CV of all proteins was the lowest, consisted of PEDF, MASP1, GELS and C163A. The "best" panel led to better precision than the full panel on 11 out of the 16 target proteins. The median CV of all proteins was 11.2% using the "best" panel versus 11.9% using the full panel. The "best" panel was marginally more precise than the full panel (P=0.21) and lowered protein CV by a median value of 0.2%.

To assess whether normalization panels that are tailored to individual target proteins are better than the full panel, an "optimal" panel was selected for each of the 16 target proteins on the basis that the corresponding CV was the lowest (FIG. 8B). To avoid over-fitting, the "optimal" panels were selected from the same dataset in which the scaling constants of InteQuan were determined and tested on the combined HPS dataset. The "optimal" panels led to better precision than the full panel on only 6 out of the 16 target proteins on the combined HPS dataset. The median CV of all proteins was 13.4% using the "optimal" panels versus 11.9% using the full panel. The "optimal" panels were marginally less precise than the full panel (P=0.45) and increased protein CV by a median value of 0.5%. The full panel had a better overall performance than "optimal" panels on the combined HPS dataset.

Example 10

EPN as an Alternative to InteQuan

To compare the precision of all four quantification methods (raw MS data, EPN, SISQuan, and InteQuan), CVs of protein abundance were evaluated from data of the 10 HPS samples in Study I (Table 6). Among the four methods, InteQuan was statistically more precise than SISQuan (P=$5.2 \times 10^{-4}$), SISQuan was only marginally better than EPN (P=0.80), and EPN was significantly better than the raw data (P=$3.1 \times 10^{-5}$). Thus, the four quantification methods were ranked by their precision in descending order as InteQuan, SISQuan, EPN, and the raw MS data.

TABLE 6

Coefficient of variation (CV) of protein abundance as evaluated on the 10 HPS samples in Study I

| Protein | CV (%) | | | | CV reduction (%) | | |
| --- | --- | --- | --- | --- | --- | --- | --- |
| (HUMAN) | InteQuan | SISQuan | EPN | Raw | SISQuan − InteQuan | EPN − SISQuan | Raw − EPN |
| KIT | 8.8 | 9.6 | 15.0 | 24.1 | 0.8 | 5.4 | 9.2 |
| FRIL | 16.8 | 25.2 | 21.9 | 28.0 | 8.4 | −3.3 | 6.1 |
| COIA1 | 12.6 | 17.8 | 20.3 | 27.2 | 5.2 | 2.5 | 7.0 |
| PRDX1 | 10.7 | 15.4 | 12.1 | 19.7 | 4.7 | −3.3 | 7.6 |
| TENX | 11.1 | 13.6 | 9.6 | 20.2 | 2.5 | −4.0 | 10.6 |
| ENPL | 13.1 | 18.9 | 6.9 | 19.1 | 5.8 | −12.0 | 12.2 |
| GRP78 | 6.8 | 11.4 | 16.7 | 22.5 | 4.5 | 5.3 | 5.8 |
| BGH3 | 5.0 | 12.3 | 16.7 | 23.3 | 7.3 | 4.4 | 6.5 |
| ALDOA | 6.6 | 13.6 | 17.7 | 28.6 | 7.0 | 4.1 | 11.0 |
| GGH | 6.9 | 7.1 | 6.8 | 17.2 | 0.2 | −0.3 | 10.3 |
| CD14 | 4.1 | 8.0 | 21.1 | 31.8 | 3.8 | 13.1 | 10.7 |
| LG3BP | 8.8 | 13.0 | 8.8 | 19.4 | 4.2 | −4.2 | 10.6 |
| TSP1 | 11.6 | 18.3 | 19.6 | 22.5 | 6.7 | 1.3 | 2.8 |
| IBP3 | 5.7 | 11.6 | 5.7 | 12.4 | 5.9 | −5.9 | 6.6 |
| TETN | 9.9 | 17.8 | 19.6 | 21.7 | 7.9 | 1.8 | 2.1 |
| ISLR | 10.0 | 9.1 | 13.5 | 20.5 | −0.9 | 4.4 | 7.0 |
| Median | 9.3 | 13.3 | 15.9 | 22.1 | 4.9 | 1.6 | 7.3 |
| P value (paired sign test) | | | | | $5.2 \times 10^{-04}$ | 0.80 | $3.1 \times 10^{-05}$ |

The above results indicate that the label-free EPN could be an attractive alternative to InteQuan, especially when it was too costly to obtain SIS peptides for hundreds to thousands of proteins of interest in early-stage biomarker discovery studies. Using EPN, the median CV of all proteins was 15.9%. Three proteins had a CV just above 20%, including FRIL (12 ng/ml, 21.9%), CD14 (420 ng/ml, 21.1%), and COIA1 (35 ng/ml, 20.3%). CVs of the remaining 13 target proteins were all below 20%, including eight proteins with a CV at or below 15% and five proteins with a CV below 10%.

To further assess EPN, Pearson correlation coefficients of protein abundance as evaluated using different quantification methods were calculated on data of the 55 clinical samples in Study I (Table 7). The median Pearson correlation coefficient between InteQuan and EPN was 0.843. The lowest coefficient between them was 0.621 (CD14, $P=4.3\times 10^{-7}$). So the correlation between InteQuan and EPN was significant for all the target proteins.

TABLE 7

Pearson correlation coefficient of protein abundance as evaluated on the 55 clinical samples in Study I

| Protein (HUMAN) | InteQuan vs. EPN | InteQuan vs. SISQuan | InteQuan vs. Raw | EPN vs. SISQuan | EPN vs. Raw | SISQuan vs. Raw |
|---|---|---|---|---|---|---|
| KIT | 0.789 | 0.669 | 0.502 | 0.630 | 0.625 | 0.883 |
| FRIL | 0.963 | 0.919 | 0.862 | 0.933 | 0.898 | 0.971 |
| COIA1 | 0.801 | 0.735 | 0.630 | 0.712 | 0.784 | 0.888 |
| PRDX1 | 0.965 | 0.979 | 0.958 | 0.977 | 0.986 | 0.990 |
| TENX | 0.818 | 0.811 | 0.663 | 0.641 | 0.742 | 0.805 |
| ENPL | 0.936 | 0.883 | 0.838 | 0.781 | 0.831 | 0.893 |
| GRP78 | 0.850 | 0.802 | 0.630 | 0.741 | 0.774 | 0.841 |
| BGH3 | 0.740 | 0.679 | 0.589 | 0.685 | 0.760 | 0.882 |
| ALDOA | 0.954 | 0.958 | 0.943 | 0.902 | 0.927 | 0.977 |
| GGH | 0.837 | 0.804 | 0.749 | 0.621 | 0.844 | 0.792 |
| CD14 | 0.621 | 0.498 | 0.234 | 0.704 | 0.727 | 0.782 |
| LG3BP | 0.900 | 0.910 | 0.826 | 0.807 | 0.865 | 0.913 |
| TSP1 | 0.972 | 0.951 | 0.954 | 0.928 | 0.945 | 0.992 |
| IBP3 | 0.918 | 0.816 | 0.749 | 0.756 | 0.784 | 0.872 |
| TETN | 0.775 | 0.779 | 0.702 | 0.680 | 0.745 | 0.905 |
| ISLR | 0.737 | 0.637 | 0.518 | 0.634 | 0.678 | 0.890 |
| Median | 0.843 | 0.808 | 0.725 | 0.726 | 0.784 | 0.889 |

All the 55 clinical samples in Study I had matching data from a previous label-free study. Major differences between the two studies were described in Example 1, N. Pearson correlation coefficients of protein abundance were computed on data from the 55 clinical samples, using InteQuan on data from Study I and using EPN on data from the discovery study (Table 8). The median Pearson correlation coefficient between the two studies was 0.821. All proteins had a correlation coefficient above 0.5 except for TETN (0.418, $P=1.5\times 10^{-3}$). Despite major differences between the two studies, the correlation between EPN and InteQuan was significant for all the target proteins. Correlations between all feasible quantification methods on the two datasets are also listed in Table 8. Based on this evidence, it was justified to use EPN as an economical alternative to InteQuan in early-stage biomarker discovery studies.

TABLE 8

Pearson correlation coefficient of protein abundance between Study I and a discovery study[a]

| Protein (HUMAN) | InteQuan vs. EPN | InteQuan vs. Raw | EPN vs. EPN | EPN vs. Raw | SISQuan vs. EPN | SISQuan vs. Raw | Raw vs. EPN | Raw vs. Raw |
|---|---|---|---|---|---|---|---|---|
| KIT | 0.711 | 0.536 | 0.560 | 0.404 | 0.270 | 0.434 | 0.196 | 0.290 |
| FRIL | 0.953 | 0.829 | 0.850 | 0.781 | 0.815 | 0.857 | 0.721 | 0.791 |
| COIA1 | 0.770 | 0.610 | 0.715 | 0.605 | 0.679 | 0.735 | 0.626 | 0.646 |
| PRDX1 | 0.978 | 0.971 | 0.946 | 0.943 | 0.950 | 0.975 | 0.937 | 0.956 |
| TENX | 0.831 | 0.690 | 0.800 | 0.711 | 0.607 | 0.683 | 0.551 | 0.615 |
| ENPL | 0.648 | 0.652 | 0.629 | 0.638 | 0.499 | 0.647 | 0.432 | 0.560 |
| GRP78 | 0.649 | 0.618 | 0.620 | 0.656 | 0.444 | 0.624 | 0.367 | 0.597 |
| BGH3 | 0.521 | 0.364 | 0.216 | 0.202 | 0.284 | 0.523 | 0.204 | 0.363 |

TABLE 8-continued

Pearson correlation coefficient of protein abundance between Study I and a discovery study[a]

| Protein (HUMAN) | InteQuan vs. EPN | InteQuan vs. Raw | EPN vs. EPN | EPN vs. Raw | SISQuan vs. EPN | SISQuan vs. Raw | Raw vs. EPN | Raw vs. Raw |
|---|---|---|---|---|---|---|---|---|
| ALDOA | 0.900 | 0.882 | 0.868 | 0.847 | 0.865 | 0.899 | 0.826 | 0.870 |
| GGH | 0.835 | 0.622 | 0.830 | 0.666 | 0.656 | 0.717 | 0.745 | 0.755 |
| CD14 | 0.841 | 0.395 | 0.588 | 0.412 | 0.543 | 0.642 | 0.330 | 0.411 |
| LG3BP | 0.921 | 0.836 | 0.833 | 0.772 | 0.904 | 0.935 | 0.854 | 0.911 |
| TSP1 | 0.909 | 0.802 | 0.876 | 0.750 | 0.918 | 0.902 | 0.918 | 0.884 |
| IBP3 | 0.811 | 0.664 | 0.750 | 0.598 | 0.515 | 0.609 | 0.457 | 0.486 |
| TETN | 0.418 | 0.416 | 0.277 | 0.289 | 0.353 | 0.551 | 0.443 | 0.581 |
| ISLR | 0.783 | 0.651 | 0.700 | 0.637 | 0.554 | 0.712 | 0.500 | 0.624 |
| Median | 0.821 | 0.652 | 0.733 | 0.647 | 0.581 | 0.698 | 0.526 | 0.620 |

[a]Evaluated on the 55 common clinical samples between the two studies and labeled as method on data of Study I versus method on data of the discovery study.

The amino acid sequences for all proteins of interest described herein are described in Table 9.

TABLE 9

Amino Acid Sequences for Proteins of Interest

| Protein Name | Amino Acid Sequences | Seq. ID. |
|---|---|---|
| BGH3_HUMAN | MALFVRLLALALALALGPAATLAGPAKSPYQLVLQHSRLRGRQHGPNVCAVQKVIGTNRKYFTNCKQWYQRKICGKSTVISYECC PGYEKVPGEKGCPAALPLSNLYETLGVVGSTTTQLYTDRTEKLRPEMEGPGSFTIFAPSNEAWASLPAEVLDSLVSNVNIELLNA LRYHMVGRRVLTDELKHGMTLTSMYQNSNIQIHHYPNGIVTVNCARLLKADHHATNGVVHLIDKVISTITNNIQQIIEIEDTFET LRAAVAASGLNTMLEGNGQYTLLAPTNEAFEKIPSETLNRILGDPEALRDLLNNHILKSAMCAEAIVAGLSVETLEGTTLEVGCS GDMLTINGKAIISNKDILATNGVIHYIDELLIPDSAKTLFELAAESDVSTAIDLFRQAGLGNHLSGSERLTLLAPLNSVFKDGTP PIDAHTRNLLRNHIIKDQLASKYLYHGQTLETLGGKKLRVFVYRNSLCIENSCIAAHDKRGRYGTLFTMDRVLTPPMGTVMDVLK GDNRFSMLVAAIQSAGLTETLNREGVYTVFAPTNEAFRALPPRERSRLLGDAKELANILKYHIGDEILVSGGIGALVRLKSLQGD KLEVSLKNNVVSVNKEPVAEPDIMATNGVVHVITNVLQPPANRPQERGDELADSALEIFKQASAFSRASQRSVRLAPVYQKLLER MKH | 1 |
| GGH_HUMAN | MASPGCLLCVLGLLLCGAASLELSRPHGDTAKKPIIGILMQKCRNKVMKNYGRYYIAASYVKYLESAGARVVPVRLDLTEKDYEI LFKSINGILFPGGSVDLRRSDYAKVAKIFYNLSIQSFDDGDYFPVWGTCLGFEELSLLISGECLLTATDTVDVAMPLNFTGGQLH SRMFQNFPTELLLSLAVEPLTANFHKWSLSVKNFTMNEKLKKFFNVLTTNTDGKIEFISTMEGYKYPVYGVQWHPEKAPYEWKNL DGISHAPNAVKTAFYLAEFFVNEARKNNHHFKSESEEEKALIYQFSPIYTGNISSFQQCYIFD | 2 |
| LG3BP_HUMAN | MTPPRLFWVWLLVAGTQGVNDGDMRLADGGATNQGRVEIFYRGQWGTVCDNLWDLTDASVVCRALGFENATQALGRAAFGQGSGP IMLDEVQCTGTEASLADCKSLGWLKSNCRHERDAGVVCTNETRSTHTLDLSRELSEALGQIFDSQRGCDLSISVNVQGEDALGFC GHTVILTANLEAQALWKEPGSNVTMSVDAECVPMVRDLLRYFYSRRIDITLSSVKCFHKLASAYGARQLQGYCASLFAILLPQDP SFQMPLDLYAYAVATGDALLEKLCLQFLAWNFEALTQAEEAWPSVPTDLLQLLLPRSDLAVPSELALLKAVDTWSWGERASHEEVE GLVEKIRFPMMLPEELFELQFNLSLYWSHEALFQKKTLQALEFHTVPFQLLARYKGLNLTEDTYKPRIYTSPTWSAFVTDSSWSA RKSQLVYQSRRGPLVKYSSDYFQAPSDYRYYPYQSFQTPQHPSFLFQDKRVSWSLVYLPTIQSCWNYGFSCSSDELPVLGLTKSG GSDRTIAYENKALMLCEGLFVADVTDFEGWKAAIPSALDTNSSKSTSSFPCPAGHFNGFRTVIRPFYLTNSSGVD | 3 |
| PRDX1_HUMAN | MSSGNAKIGHPAPNFKATAVMPDGQFKDISLSDYKGKYVVFFFYPLDFTFVCPTEIIAFSDRAEEFKKLNCQVIGASVDSHFCHL AWVNTPKKQGGLGPMNIPLVSDPKRTIAQDYGVLKADEGISFRGLFIIDDKGILRQITVNDLPVGRSVDETLRLVQAFQFTDKHG EVCPAGWKPGSDTIKPDVQKSKEYFSKQK | 4 |
| TSP1_HUMAN | MGLAWGLGVLFLMHVCGTNRIPESGGDNSVFDIFELTGAARKGSGRRLVKGPDPSSPAFRIEDANLIPPVPDDKFQDLVDAVRAE KGFLLLASLRQMKKTRGTLLALERKDHSGQVFSVVSNGKAGTLDLSLTVQGKQHVVSVEEALLATGQWKSITLFVQEDRAQLYID CEKMENAELDVPIQSVFTRDLASIARLRIAKGGVNDNFQGVLQNVRFVFGTTPEDILRNKGCSSSTSVLLTLDNNVVNGSSPAIR TNYIGHKTKDLQAICGISCDELSSMVLELRGLRTIVTTLQDSIRKVTEENKELANELRRPPLCYHNGVQYRNNEEWTVDSCTECH CQNSVTICKKVSCPIMPCSNATVPDGECCPRCWPSDSADDGWSPWSEWTSCSTSCGNGIQQRGRSCDSLNNRCEGSSVQTRTCHI QECDKRFKQDGGWSHWSPWSSCSVTCGDGVITRIRLCNSPSPQMNGKPCEGEARETKACKKDACPINGGWGPWSPWDICSVTCGG GVQKRSRLCNNPTPQFGGKDCVGDVTENQICNKQDCPIDGCLSNPCFAGVKCTSYPDGSWKCGACPPGYSGNGIQCTDVDECKEV PDACFNHNGEHRCENTDPGYNCLPCPPRFTGSQPFGQGVEHATANKQVCKPRNPCTDGTHDCNKNAKCNYLGHYSDPMYRCECKP GYAGNGIICGEDTDLDGWPNENLVCVANATYHCKKDNCPNLPNSGQEDYDKDGIGDACDDDDDNDKIPDDRDNCPFHYNPAQYDY DRDDVGDRCDNCPYNHNPDQADTDNNGEGDACAADIDGDGILNERDNCQYVYNVDQRDTDMDGVGDQCDNCPLEHNPDQLDSDSD RIGDTCDNNQDIDEDGHQNNLDNCPYVPNANQADHDKDGKGDACDHDDDNDGIPDDKDNCRLVPNPDQKDSDGDGRGDACKDDFD HDSVPDIDDICPENVDISETDFRRFQMIPLDPGKGTSQNDPNWVRHQGKELVQTVNCDPGLAVGYDEFNAVDFSGTFFINTERDD DYAGFVFGYQSSSRFYVVMWKQVTQSYWDTNPTRAQGYSGLSVKVVNSTTGPGEHLRNALWHTGNTPGQVRTLWHDPRHIGWKDF TAYRWRLSHRPKTGFIRVVMYEGKKIMADSGPIYDKTYAGGRLGLFVFSQEMVFFSDLKYECRDP | 5 |
| CD44_HUMAN | MDKFWWHAAWGLCLVPLSLAQIDLNITCRFAGVFHVEKNGRYSISRTEAADLCKAFNSTLPTMAQMEKALSIGFETCRYGFIEGH VVIPRIHPNSICAANNTGVYILTSNTSQYDTYCFNASAPPEEDCTSVTDLPNAFDGPITITIVNRDGTRYVQKGEYRTNPEDIYP SNPTDDDVSSGSSSERSSTSGGYIFYTFSTVHPIPDEDSPWITDSTDRIPATTLMSTSATATETATKRQETWDWFSWLFLPSESK NHLHTTTQMAGTSSNTISAGWEPNEENEDERDRHLSFSGSGIDDDEDFISSTISTTPRAFDHTKQNQDWTQWNPSHSNPEVLLQT TTRMTDVDRNGTTAYEGNWNPEAHPPLIHHEHHEEEETPHSTSTIQATPSSTTEETATQKEQWFGNRWHEGYRQTPKEDSHSTTG TAAASAHTSHPMQGRTTPSPEDSSWTDFFNPISHPMGRGHQAGRRMDMDSSHSITLQPTANPNTGLVEDLDRTGPLSMTTQQSNS QSFSTSHEGLEEDKDHPTTSTLTSSNRDVTGGRRDPNHSEGSTTLLEGYTSHYPHTKESRTFIPVTSAKTGSFGVTAVTVGDSN | 6 |

TABLE 9-continued

Amino Acid Sequences for Proteins of Interest

| Protein Name | Amino Acid Sequences | Seq. ID. |
|---|---|---|
| | SNVNRSLSGDQDTFHPSGGSHTTHGSESDGHSGSQEGGANTTSGPIRTPQIPEWLIILASLLALALILAVCIAVNSRRRCGQKK KLVINSGNGAVEDRKPSGLNGEASKSQEMVHLVNKESSETPDQFMTADETRNLQNVDMKIGV | |
| ENPL_HUMAN | MRALWVLGLCCVLLTFGSVRADDEVDVDGTVEEDLGKSREGSRTDDEVVQREEEATQLDGLNASQIRELREKSEKFAFQAEVNRM MKLIINSLYKNKEIFLRELISNASDALDKIRLISLTDENALSGNEELTVKIKCDKEKNLLHVTDTGVGMTREELVKNLGTIAKSG TSEFLNKMTEAQEDGQSTSELIGQFGVGFYSAFLVADKVIVTSKHNNDTQHIWESDSNEFSVIADPRGNTLGRGTTITLVLKEEA SDYLELDTIKNLVKKYSQFINFPIYVWSSKTETVEEPMEEEEAAKEEKEESDDEAAVEEEEEEKKPKTKKVEKTVWDWELMNDIK PIWQRPSKEVEEDEYKAFYKSFSKESDDPMAYIHFTAEGEVTFKSILFVPTSAPRGLFDEYGSKKSDYIKLYVRRVFITDDFHDM MPKYLNFVKGVVDSDDLPLNVSRETLQQHKLLKVIRKKLVRKTLDMIKKIADDKYNDTFWKEFGTNIKLGVIEDHSNRTRLAKLL RFQSSHHPTDITSLDQYVERMKEKQDKIYFMAGSSRKEAESSPFVERLLKKGYEVIYLTEPVDEYCIQALPEFDGKRFQNVAKEG VKFDESEKTKESREAVEKEFEPLLNWMKDKALKDKIEKAVVSQRLTESPCALVASQYGWSGNMERIMKAQAYQTGKDISTNYYAS QKKTFEINPRHPLIRDMLRRIKEDEDDKTVLDLAVVLFETATLRSGYLLPDTKAYGDRIERMLRLSLNIDPDAKVEEEPEEEPEE TAEDTTEDTEQDEDEEMDVGTDEEEETAKESTAEKDEL | 7 |
| TENX_HUMAN | MMPAQYALTSSLVLLVLLSTARAGPFSSRSNVTLPAPRPPPQPGGHTVGAGVGSPSSQLYEHTVEGGEKQVVFTHRINLPPSTGC GCPPGTEPPVLASEVQALRVRLEILEELVKGLKEQCTGGCCPASAQAGTQTDVRTLCSLHGVFDLSRCTCSCEPGWGGPTCSDP TDAEIPPSSPPSASGSCPDDCNDQGRCVRGRCVCFPGYTGPSCGWPSCPGDCQGRGRCVQGVCVCRAGFSGPDCSQRSCPRGCSQ RGRCEGGRCVCDPGYTGDDCGMRSCPRGCSQRGRCENGRCVCNPGYTGEDCGVRSCPRGCSQRGRCKDGRCVCDPGYTGEDCGTR SCPWDCGEGGRCVDGRCVCWPGYTGEDCSTRTCPRDCRGRGRCEDGECICDTGYSGDDCGVRSCPGDCNQRGRCEDGRCVCWPGY TGTDCGSRACPRDCRGRGRCENGVCVCNAGYSGEDCGVRSCPGDCRGRGRCESGRCMCWPGYTGRDCGTRACPGDCRGRGRCVDG RCVCNPGFTGEDCGSRRCPGDCRGHGLCEDGVCVCDAGYSGEDCSTRSCPGGCRGRGQCLDGRCVCEDGYSGEDCGVRQCPNDCS QHGVCQDGVCICWEGYVSEDCSIRTCPSNCHGRGRCEEGRCLCDPGYTGPTCATRMCPADCRGRGRCVQGVCLCHVGYGGEDCGQ EEPPASACPGGCGPRELCRAGQCVCVEGFRGPDCAIQTCPGDCRGRGECHDGSCVCKDGYAGEDCGEARVPSSASAYDQRGLAPG QEYQVTVRALRGTSWGLPASKTITTMIDGPQDLRVVAVTPTTLELGWLRPQAEVDRFVVSYVSAGNQRVRLEVPPEADGTLLTDL MPGVEYVVTVTAERGRAVSYPASVRANTEEREEESPPRPSLSQPPRRPWGNLTAELSRFRGTVQDLERHLRAHGYPLRANQTYTS VARHIHEYLQRQVLGSSADGALLVSLDGLRGQFERVVLRWRPQPPAEGPGGELTVPGTTRTVSLPDLRPGTTYHVEVHGVRAGQT SKSYAFITTTGPSTTQGAQAPLLQQRPQELGELRVLGRDETGRLRVVWTAQPDTFAYFQLRMRVPEGPGAHEEVLPGDVRQALVP PPPPGTPYELSLHGVPPGGKPSDPIIYQGIMDKDEEKPGKSSGPPRLGELTVTDRTSDSLLLRWTVPEGEFDSFVIQYKDRDGQP QVVPVEGPQRSAVITSLDPGRKYKFVLYGFVGKKRHGPLVAEAKILPQSDPSPGTPPHLGNLWVTDPTPDSLHLSWTVPEGQFDT FMVQYRDRDGRPQVVPVEGPERSFVVSSLDPDHKYRFTLFGIANKKRYGPLTADGTTAPERKEEPPRPEFLEQPLLGELTVTGVT PDSLRLSWTVAQGPFDSFMVQYKDAQGQPQAVPVAGDENEVTVPGLDPDRKYKMNLYGLRGRQRVGPESVVAKTAPQEDVDETPS PTELGTEAPESPEEPLLGELTVTGSSPDSLSLFWTVPQGSFDSFTVQYKDRDGRPRAVRVGGKESEVTVGGLEPGHKYKMHLYGL HEGQRVGPVSAVGVTAPQQEETPPATESPLEPRLGELTVTDPTPNSVGLSWTVPEGQFDSFTVQYKDKDGQPQVVPVAADQREVT VYNLEPERKYKMNMYGLHDGQRMGPLSVVIVTAPATEASKPPLEPRLGELTVTDITPDSVGLSWTVPEGEFDSFVVQYKDRDGQP QVVPVAADQREVTIPDLEPSRKYKFLLFGIQDGKRRSPVSVEAKTVARGDASPGAPPRLGELWVTDPTPDSLRLSWTVPEGQFDS FVVQFKDKDGPQVVPVEGHERSVTVTPLDAGRKYRFLLYGLLGKKRHGPLTADGTTEARSAMDDTGTKRPPKPRLGEELQVTTVT QNSVGLSWTVPEGQFDSFVVQYKDRDGQPQVVPVEGSLREVSVPGLDPAHRYKLLLYGLHHGKRVGPISAVAITAGREETETETT APTPPAPEPHLGELTVEEATSHTLHLSWMVTGEGEFDSFEIQYTDRDGQLQMVRIGGDRNDITLSGLESDHRYLVTLTYGFSDGKHV GPVHVEALTVPEEEKPSEPPTATPEPPIKPRLGELTVTDATPDSLSLSWTVPEGQFDHFLVQYRNGDGQPKAVRVPGHEEGVTIS GLEPDHKYKMNLYGFHGGQRMGPVSVVGVTEPSMEAPEPAEEPLLGELTVTGSSPDSLSLSWTVPQGRFDSFTVQYKDRDGRPQV VRVGGEESEVTVGGLEPGRKYKMHLYGLHEGRRVGPSAVGVTAPEEENPSDAPLAKLRLGQMTVRDITSDSLSLSWTVPEGQFDH FLVQFKNGDGQPKAVRVPGHEDGVTISGLEPDHKYKMNLYGFHGGQRVGPVSAVGLTASTEPPTPEPPIKPRLEELTVTDATPDS LSLSWTVPEGQFDHFLVQYKNGDGQPKATRVPGHEDVTISGLEPDNKYKMNLYGFHGGQRVGPSAIGVTEEETPSPTEPSMEA PEPPEEPLLGELTVTGSSPDSLSLSWTVPQGRFDSFTVQYKDRDGRPQVVRVGGEESEVTVGGLEPGRKYKMHLYGLHEGRRVGP VSTVGVTAPQEDVDETPSPTEPGTEAPGPPEEPLLGELTVTGSSPDSLSLSWTVPQGRFDSFTVQYKDRDGRPQAVRVGGQESKV TVRGLEPGRKYKMHLYGLHEGRRLGPVSAVGVTEDEAETTQAVPTMTPEPPIKPRLGELTMTDATPDSLSLSWTVPEGQFDHFLV QYRNGDGQPKAVRVPGHEDGVTISGLEPDHKYKMNLYGFHGGQRVGPISVIGVTEEETPSPTELSTEAPEPPEEPLLGELTVTGS SPDSLSLSWTIPQGHFDSFTVQYKDRDGRPQVMRVRGEESEVTVGGLEPGRKYKMHLYGLHEGRRVGPVSTVGVTVPTTTPEPPN KPRLGELTVTDATPDSLSLSWMVPEGQFDHFLVQYRNGDGQPKVVRVPGHEDGVTISGLEPDHKYKMNLYGFHGGQRVGPISVIG VTEEETPAPTEPSTEAPEPPEEPLLGELTVTGSSPDSLSLSWTIPQGRFDSFTVQYKDRDGRPQVVRVRGEESEVTVGGLEPGCK YKMHLYGLHEGQRVGPVSAVGVTAPKDEAETTQAVPTMTPEPPIKPRLGELTVTDATPDSLSLSWMVPEGQFDHFLVQYRNGDGQ PKAVRVPGHEDGVTISGLEPDHKYKMNLYGFHGGQRVGPVSAIGVTEEETPSPTEPSTEAPEAPEEPLLGELTVTGSSPDSLSLS WTVPQGRFDSFTVQYKDRDGQPQVVRVRGEESEVTVGGLEPGRKYKMHLYGLHEGQRVGPVSTVGITAPLPTPLPVEPRLGELAV AAVTSDSVGLSWTVAQGPFDSFLVQYRDAQGQPQAVPVSGDLRAVAVSGLDPARKYKFLLFGLQNGKRHGPVPVEARTAPDTKPS PRLGELTVTDATPDSVGLSWTVPEGEFDSFVVQYKDKDGRLQVVPVAANQREVTVQGLEPSRKYRFLLYGLSGRKRLGPISADST TAPLEKELPPHLGELTVAEETSSSLRLSWTVAQGPFDSFVVQYRDTDGQPRAVPVAADQRTVTVEDLEPGKKYKFLLYGLLGGKR LGPVSALGMTAPEEDTPAPELAPEAPEPPEEPRLGVLTVTDTTPDSMRLSWSVAQGPFDSFVVQYEDTNGQPQALLVDGDQSKIL ISGLEPSTPYRFLLYGLHEGKRLGPLSAEGTTGLAPAGQTSEGSRPRLSQLSVTDVAHPSLTLSWTLNWEAPPGAFDSFLLRFGVPSPS TLEPHPRPLLQRELMVPGTRHSAVLRDLRSGTLYSLTLYGLRGPHKADSIQGTARTLSPVLESPRDLQFSEIRETSAKVNWMPPP SRADSFKVSYQLADGGEPQSVQVDGQARTQKLQGLIPGARYEVTVVSVRGFEESEPLTGFLTTVPDGPTQLRALNLTEGFAVLHW KPPQNPVDTYDVQVTAPGAPPLQAETPGSAVDYPLHDLVLHTNYTATVRGLRGPNLTSPASITFTTGLEAPRDLEAKEVTPRTAL LTWTEPPVVRPAGYLLSFHTPGGQNQEILLPGGITSHQLLGLPPTSTPSYNARLQAMWGQSLLPPVSTSFTTGLRIPFPRDCGEEMQ NGAGASRTSTIFLNGNRERPLNVFCDMETDGGGWLVFQRRMDGQTDFWRDWEDYAHGFGNISGEFWLGNEALHSLTQAGDYSMRV DLRAGDEAVFAQYDSFHVDSAAEYYRLHLEGYHGTAGDSMSYHSGSVFSARDRDPNSLLISCAVSYRGAWWYRNCHYANLNGLYG STVDHQGVSWYHWKGFEFSVPFTEMKLRPRNFRSPAGGG | 8 |
| AIFM1_HUMAN | MFRCGGLAAGALKQKLVPLVRTVCVRSPRQRNRLPGNLFQRWHVPLELQMTRQMASSGASGGKIDNSVLVLIVGLSTVGAGAYAY KTMKEDEKRYNERISGLGLTPEQKQKKAALSASEGEEVPQDKAPSHVPPLLIGGGTAAFAAARSIRARDPGARVLIVSEDPELPY MRPPLSKELWFSDDPNVTKTLRFKQWNGKERSIYFQPPSFYVSAQDLPHIENGGVAVLTGKKVVQLDVRDNMVKLNDGSQITYEK CLIATGGTPRSLSALDRAGAEVKSRTTLFRKIGDFRSLEKISREVKSITIIGGGFLGSELACALGRKARALGTEVIQLFPEKGNM GKILPEYLSNWTMEKVRREGVKVMPNAIVQSVGVSSGKLLIKLKDGRKVETDHIVAAVGLEPNVELAKTGGLEIDSDFGGFRVNA ELQARSNIWVAGDAACFYDIKLGRRRVEHHDAVVSGRLAGENMTGAAKPYWHQSMFWSDLGPDVGYEAIGLVDSSLPTVGVFAK ATAQDNPKSATEQSGTGIRSESETESEASEITIPPSTPAVPQAPVQGEDYGKGVIFYLRDKVVVGIVLWNIFNRMPIARKIIKDG EQHEDLNEVAKLFNIHED | 9 |

TABLE 9-continued

Amino Acid Sequences for Proteins of Interest

| Protein Name | Amino Acid Sequences | Seq. ID. |
|---|---|---|
| IBP3_HUMAN | MQRARPTLWAAALTLLVLLRGPPVARAGASSAGLGPVVRCEPCDARALAQCAPPPAVCAELVREPGCGCCLTCALSEGQPCGIYT ERCGSGLRCQPSPDEARPLQALLDGRGLCVNASAVSRLRAYLLPPAPPAPGNASESEEDRSAGSVESPSVSSTHRVSDPKFHPLHS KIIIIKKGHAKDSQRYKVDYESQSTDTQNFSSESKRETEYGPCRREMEDTLNHLKFLNVLSPRGVHIPNCDKKGFYKKKQCRPSK GRKRGFCWCVDKYGQPLPGYTTKGKEDVHCYSMQSK | 10 |
| GELS_HUMAN | MAPHRPAPALLCALSLALCALSLPVRAATASRGASQAGAPQGRVPEARPNSMVVEHPEFLKAGKEPGLQIWRVEKFDLVPVPTNL YGDFFTGDAYVILKTVQLRNGNLQYDLHWLGNECSQDESGAAAIFTVQLDDYLNGRAVQHREVQGFESATFLGYFKSGLKYKKG GVASGFKHVVPNEVVVQRLFQVKGRRVVRATEVPVSWESFNNGDCFILDLGNNIHQWCGSNSNRYERLKATQVSKGIRDNERSGR ARVHVSEEGTEPEAMLQVLGPKPALPAGTEDTAKEDAANRKLAKLYKVSNGAGTMSVSLVADENPFAQGALKSEDCFILDHGKDG KIFVWKGKQANTEERKAALKTASDFITKMDYPKQTQVSVLPEGGETPLFKQFFKNWRDPDQTDGLGLSYLSSHIANVERVPFDAA TLHTSTAMAAQHGMDDDGTGQKQIWRIEGSNKVPVDPATYGQFYGGDSYIILYNYRHGGRQGQIIYNWQGAQSTQDEVAASAILT AQLDEELGGTPVQSRVVQGKEPAHLMSLFGGKPMIIYKGGTSREGGQTAPASTRLFQVRANSAGATRAVEVLPKAGALNSNDAFV LKTPSAAYLWVGTGASEAEKTGAQELLRVLRAQPVQVAEGSEPDGFWEALGGKAAYRTSPRLKDKKMDAHPPRLFACSNKIGRFV IEEVPGELMQEDLATDDVMLLDTWDQVFVWVGKDSQEEEKTEALSAKRYIETDPANRDRRTPITVVKQGFEPPSFVGWFLGWDD DYWSVDPLDRAMAELAAGCGCGCCCGCTGCAGGCGCTGCTGGATGGCCGCGGCCTGTGCGTGAACGCGAGCGCGGTGAGCCGCCT GCGCGCGTATCTGCTGCCGGCCGCCGCCGGCGCCGGGCGAACCGCCGGCGCCGGGCAACGCGGCGAAAGCGAAGATCGCAGC GCGGGCAGCGTGGAAAGRCCGAGCGTGAGCAGCACCCATCGCGTGAGCGATCCGAAATTTCATCCGCTGCATAGCAAAATTATTA TTATTAAAAAAGGCCATGCGAAAGATAGCCAGCGCTATAAAGTGGATTATGAAAGCCAGAGCACCGATACCCAGAACTTTAGCAG CGAAAGCAAACGCGAAACCGAATATGGCCCGTGCCGCCGCGAAATGGAAGATACCCTGAACCATCTGAAATTTCTGAACGTGCTG AGCCCGCGCGGCGTGCATATTCCGAACTGCGATAAAAAGGCTTTTTATAAAAAAAAACAGTGCCGCCCGAGCAAAGGCCGCAAAC GCGGCTTTTGCTGGTGCGTGGATAAATATGGCCAGCCGCTGCCGGGCTATACCACCAAAGGCAAAGAAGATGTGCATTGCTATAG CATGCAGAGCAAA | 11 |
| MASP1_HUMAN | MRWLLLYYALCFSLSKASAHTVELNNMFGQIQSPGYPDSYPSDSEVTWNITVPDGFRIKLYFMHFNLESSYLCEYDYVKVETEDQ VLATFCGRETTDEQTPGQEVVLSPGSFMSITFRSDFSNEERFTGFDAHYMAVDVDECKEREDEELSCDHYCHNYIGGYYCSCRF GYILHTDNRTCRVECSDNLFTQRTGVITSPDFPNPYPKSSECLYTIELEEGFMVNLQFEDIFDIEDHPEVPCPYDYIKIKVGPKV LGPFCGEKAPEPISTQSHSVLILFHSDNSGENRGWRLSYRAAGNECPELQPPVHGKIEPSQAKYFFKDQVLVSCDTGYKVLKDNV EMDTFQIECLKDGTWSNKIPTCKIVDCRAPGELEHGLITFSTRNNLTTYKSEIKYSCQEPYYKMLNNNTGIYTCSAQGVWMNKVL GRSLPTCLPVCGLPKFSRKLMARIFNGRPAQKGTTPWIAMLSHLNGQPFCGGSLLGSSWIVTAAHCLHQSLDPEDPTLRDSDLLS PSDFKIILGKHWRLRSDENEQHLGVKHTTLHPQYDPNTFENDVALVELLESPVLNAFVMPICLPEGPQQEGAMVIVSGWGKQFLQ RFPETLMEIEIPIVDHSTCQKAYAPLKKKVTRDMICAGEKEGGKDACAGDSGGPMVTLNRERGQWYLVGTVSWGDDCGKKDRYGV YSYIHHNKDWIQRVTGVRN | 12 |
| COIA1_HUMAN | MAPYPCGCHILLLLFCCLAAARANLLNLNWLWFNNEDTSHAATTIPEPQGPLPVQPTADTTTHVTPRNGSTEPATAPGSPEPPSE LLEDGQDTPTSAESPDAPEENIAGVGAEILNVAKGIRSFVQLWNDTVPTESLARAETLVLETPVGPLALAGPSSTPQENGTTLWP SRGIPSSPGAHTTEAGTLPAPTSPPSLGRPWAPLTGPSVPPPSSGRASLSSLLGGAPPWGSLQDPDSQGLSPAAAAPSQQLQRP DVRLRTPLLHPLVMGSLGKHAAPSAFSSGLPGALSQVAVTTLTRDSGAWVSHVANSVGPGLANNSALLGADPEAPAGRCLPLPPS LPVCGHLGISRFWLPNHLHHESGEQVRAGARAWGGLLQTHCHPFLAWFFCLLLVPPCGSVPPPAPPPCCQFCEALQDACWSRLGG GRLPVACASLPTQEDGYCVLIGPAAERISEEVGLLQLLGDPPPQQVTQTDDPDVGLAYVFGPDANSGQVARYHFPSLFFRDFSLL FHIRPATEGPGVLFAITDSAQAMVLLGVKLSGVQDGHQDISLLYTEPGAGQTHTAASFRLPAFVGQWTHLALSVAGGFVALYVDC EEFQRMPLARSSRGLELEPGAGLFVAQAGGADPDKFQGVIAELKVRRDPQVSPMHCLDEEGDDSDGASGDSGSGLGDARELLREE TGAALKPRLPAPPVTTPPLAGGSSTEDSRSEEVEEQTTVASLGAQTLPGSDSVSTWDGSVRTPGGRVKEGGLKGQKGEPGVPGP PGRAGPPGSPCLPGPPGLPCPVSPLGPAGPALQTVPGPQGPPGPPGRDGTPGRDGEPGDPGEDGKPGDTGPQGFPGTGDVGPKG DKGDPGVGERGPPGPQGPPPGPGPSFRHDKLTFIDMEGSGFGGDLEALRGPRGFPGPPGPPGVPGLPGEPGRFGVNSSDVPGAG LPGVPGREGPPGPLPGPPGPPGREGPPGRTGQKGSLGEAGAPPGHKSKGAPGPAGARGESGLAGARGESGLAGAPGAPGPPGPPGPPGPGP GLPAGFDDMEGSGGPFWSTARSADGPQGPPGLPGLKGDPGVPGLPGAKGEVGADGVPGPGLPGREGIAGPQGPKGDRGSRGEKG DPGKDGVGQPGLPGPPGPPGPVVYSEQDGSVLSVPGPEGRPGFAGFPGPAGPKGNLGSKGERGSPGPKGEKGEPGSIFSPDGGA LGPAQKGAKGEPGFRGPPGPYGRPGYKEIGFPGRPGRPGMNGLKGEKGEPGDASLGFGMRGMPGPPGPPGPPGPPGPGTPVYDSNV FAESSRPGPPGLPGNQGPPGPKGAKGEVGPPGPPGPPFPDFLQLEAEMKGEKGDRGDAQGKGEPGEEGGGGFFGSSLPGPPGPPG PPGRGYPGIPGPKGESIRGQPGPPGPGQGPPGIGYEGRGQPPGPPGPPGPSFPGPHRQTISVPGPPGPPGPPGPPGTMGASSGV RLWATRQAMLGQVHEVPEGWLIFVAEQEELYVRVQNGFRKVQLEARTPLPRGTDNEVAALQPPVVQLHDSNPYPRREHPHPTARP WRADDILASPPRLPEPQPYPGAPHHSSYVHLRPARPTSPPAHSRDFQPVLHLVALNSPLSGGMRGIRGADFQCFQQARAVGLAG TFRAFLSSRLQDLYSIVRRADRAAVPIVNLKDELLFPSWEALFSGSEGPLKPGARIFSFDGKDVLRHPTWPQKSVWHGSDPNGRR LTESYCETWRTEAPSATGQASSLLGGRLLGQSAASCHHAYIVLCIENSFMTASK | 13 |
| GRP78_HUMAN | MKLSLVAAMLLLLSAARAEEEDKKEDVGTVVGIDLGTTYSCVGVFKNGRVEIIANDQGNRITPSYVAFTPEGERLIGDAAKNQLT SNPENTVFDAKRLIGRTWNDPSVQQDIKFLPFKVVEKKTKPYIQVDIGGGQTKTFAPEEISAMVLTKMKETAEAYLGKKVTHAVV TVPAYFNDAQRQATKDAGTIAGLNVMRIINEPTAAAIAYGLDKREGEKNILVFDLGGGTFDVSLLTIDNGVFEVVATNGDTHLGG EDFDQRVMEHFIKLYKKKTGKDVRKDNRAVQKLRREVEKAKRALSSQHQARIEIESFYEGEDFSETLTRAKFEELNMDLFRSTMK PVQKVLEDSDLKKSDIDEIVLVGGSTRIPKIQQLVKEFFNGKEPSRGINPDEAVAYGAAVQAGVLSGDQDTGDLVLLDVCPLTLG IETVGGVMTKLIPRNTVVPTKKSQIFSTASDNQPTVTIKVYEGERPLTKDNHLLGTFDLTGIPPAPRGVPQIEVTFEIDVNGILR VTAEDKGTGNKNKITITNDQNRLTPEEIERMVNDAEKFAEEDKKLKERIDTRNELESYAYSLKNQIGDKEKLGGKLSSEDKETME KAVEEKIEWLESHQDADIEDFKAKKKELEEIVQPIISKLYGSAGPPPTGEEDTAEKDEL | 14 |
| KIT_HUMAN | MRGARGAWDFLCVLLLLLRVQTGSSQPSVSPGEPSPPSIHPGKSDLIVRVGDEIRLLCTDPGFVKWTFEILDETNENKQNEWITE KAEATNTGKYTCTNKHGLSNSIYVFVRDPAKLFLVDRSLYGKEDNDTLVRCPLTDPEVTNYSLKGCQGKPLPKDLRFIPDPKAGI MIKSVKRAYHRLCLHCSVDQEGKSVLSEKFILKVRPAFKAVPVVSVSKASYLLREGEEFTVTCTIKDVSSSVYSTWKRENSQTKL QEKYNSWHHGDFNYERQATLTISSARVNDSGVFMCYANNTFGSANVTTLTEVVDKGFINIFPMINTTVFVNDGENVDLIVEYEAF PKPEHQQWIYMNRTFTDKWEDYPKSENESNIRYVSEHLTRLKGTEGGTVTFLVSNSDVNAAIAFNVYVNTKPEILTYDRLVNGM LQCVAAGFPEPTIDWYFCPGTEQRCSASVLPVDVQTLNSSGPPFGKLVVQSSIDSSAFKHNGTVECKAYNDVGKTSAYFNFAFKG NNKEQIHPHTLFTPLLIGFVIVAGMMCIIVMLTYKYLQKPMYEVQWKVVEEINGNNYVYIDPTQLPYDHKWEFPRNRLSFGKTL GAGAFGKVVEATAYGLIKSDAAMTVAVKMLKPSAHLTEREALMSELKVLSYLGNHMNIVNLLGACTIGGPTLVITEYCCYGDLLN FLRRKRDSFICSKQEDHAEAALYKNLLHSKESSCSDSTNEYMDMKPGVSYVVPTKADKRRSVRIGSYIERDVTPAIMEDDELALD LEDLLLSFSYQVAKGMAFLASKNCIHRDLAARNILLTHGRITKICDFGLARDIKNDSNYVVKGNARLPVKWMAPESIFNCVYTFES | 15 |

TABLE 9-continued

Amino Acid Sequences for Proteins of Interest

| Protein Name | Amino Acid Sequences | Seq. ID. |
|---|---|---|
| | DVWSYGIFLWELFSLGSSPYPGMPVDSKFYKMIKEGFRMLSPEHAPAEMYDIMKTCWDADPLKRPTFKQIVQLIEKQISESTNHI YSNLANCSPNRQKPVVDHSVRINSVGSTASSSQPLLVHDDV | |
| LRP1_HUMAN | MLTPPLLLLLPLLSALVAAAIDAPKTCSPKQFACRDQITCISKGWRCDGERDCPDGSDEAPEICPQSKAQRCQPNEHNCLGTELC VPMSRLCNGVQDCMDGSDEGPHCRELQGNCSRLGCQHHCVPTLDGPTCYCNSSFQLQADGKTCKDFDECSVYGTCSQLCTNTDGS FICGCVEGYLLQPDNRSCKAKNEPVDRPPVLLIANSQNILATYLSGAQVSTITPTSTRQTTAMDFSYANETVCWVHVGDSAAQTQ LKCARMPGLKGFVDEHTINISLSLHHVEQMAIDWLTGNFYFVDDIDDRIFVCNRNGDTCVTLLDLELYNPKGIALDPAMGKVFFT DYGQIPKVERCDMDGQNRTKLVDSKIVFPHGITLDLVSRLVYWADAYLDYIEVVDYEGKGRQTIIQGILIEHLYGLTVFENYLYA TNSDNANAQQKTSVIRVNRFNSTEYQVVTRVDKGGALHIYHQRRQPRVRSHACENDQYGKPGGCSDICLLANSHKARTCRCRSGF SLGSDGKSCKKPEHELFLVYGKGRPGIIRGMDMGAKVPDEHMIPIENLMNPRALDFHAETGFIYFADTTSYLIGRQKIDGTERET ILKDGIHNVEGVAVDWMGDNLYWTDDGPKKTISVARLEKAAQTRKTLIEGKMTHPRAIVVDPLNGWMYWTDWEEDPKDSRRGRLE RAWMDGSHRDIFVTSKTVLWPNGLSLDIPAGRLYWVDAFYDRIETILLNGTDRKIVYEGPELNHAFGLCHHGNYLFWTEYRSGSV YRLERGVGGAPPTVTLLRSERPPIFEIRMYDAQQQVGTNKCRVNNGGCSSLCLATPGSRQCACAEDQVLDADGVTCLANPSYVP PPQCQPGEFACANSRCIQERWKCDGDNDCLDNSDEAPALCHQHTCPSDRFKCENNRCIPNRWLCDGDNDCGNSEDESNATCSART CPPNQFSCASGRCIPISWTCDLDDDCGDRSDESASCAYPTCFPLTQFTCNNGRCININWRCDNDNDCGDNSDEAGCSHSCSSTQF KCNSGRCIPEHWTCDGDNDCGDYSDETHANCTNQATRPPGGCHTDEFQCRLDGLCIPLRWRCDGDTDCMDSSDEKSCEGVTHVCD PSVKFGCKDSARCISKAWVCDGDNDCEDNSDEENCESLACRPPSHPCANNTSVCLPPDKLCDGNDDCGDSDEGELCDQCSLNNG GCSHNCSVAPGEGIVCSCPLGMELGPDNHTCQIQSYCAKHLKCSQKCDQNKFSVKCSCYEGWVLEPDGESCRSLDPFKPFIIFSN RHEIRRIDLHKGDYSVLVPGLRNTIALDFHLSQSALYWTDVVEDKIYRGKLLDNGALTSFEVVIQYGLATPEGLAVDWIAGNIYW VESNLDQIEVAKLDGTLRTTLLAGDIEHPRAIALDPRDGILFWTDWDASLPRIEAASMSGAGRRTVHRETGSGGWPNGLTVDYLE KRILWIDARSDAIYSARYDGSGHMEVLRGHEFLSHPFAVTLYGGEVYWTDWRTNTLAKANKWTGHNVTVVQRTNTQPFDLQVYHP SRQPMAPNPCEANGGQGPCSHLCLINYNRTVSCACPHLMKLHKDNTTCYEFKKFLLYARQMEIRGVDLDAPYYNYIISFTVPDID NVTVLDYDAREQRVYWSDVRTQAIKRAFINGTGVETVVSADLPNAHGLAVDWVSRNLFWTSYDTNKKQINVARLDGSFKNAVVQG LEQPHGLVVHPLRGKLYWTDGDNISMANMDGSNRTLLFSG QKGPVGLAIDFPESKLYWISSGNHTINRCNLDGSGLEVIDAMRSQLGKATALAIMGDKLWWADQVSEKMGTCSKADGSGSVVLRN STTLVMHMKVYDESIQLDHKGTNPCSVNNGDCSQLCLPTSETTRSCMCTAGYSLRSGQQACEGVGSFLLYSVHEGIRGIPLDPND KSDALVPVSGTSLAVGIDFHAENDTIYWVDMGLSTISRAKRDQTWREDVVTNGIGRVEGIAVDWIAGNIYWTDQGFDVIEVARLN GSFRYVVISQGLDKPRAITVHPEKGYLFWTEWGQYPRIERSRLDGTERVVLVNVSISWPNGISVDYQDGKLYWCDARTDKIERID LETGENREVVLSSNNMDMFSVSVFEDFIYWSDRTHANGSIKRGSKDNATDSVPLRTGIGVQLKDIKVFNRDRQKGTNVCAVANGG CQQLCLYRGRGQRACACAHGMLAEDGASCREYAGYLLYSERTILKSIHLSDERNLNAPVQPFEDPEHMKNVIALAFDYRAGTSPG TPNRIFFSDIHFGNIQQINDDGSRRITIVENVGSVEGLAYHRGWDTLYWTSYTTSTITRHTVDQTRPGAFERETVITMSGDDHPR AFVLDECQNLMFWTNWNEQHPSIMRAALSGANVLTLIEKDIRTPNGLAIDHRAEKLYFSDATLDKIERCEYDGSHRYVILKSEPV HPFGLAVYGEHIFWTDWVRRAVQRANKHVGSNMKLLRVDIPQQPMGIIAVANDTNSCELSPCRINNGGCQDLCLLTHQGHVNCSC RGGRILQDDLTCRAV NSSCRAQDEFECANGECINFSLTCDGVPHCKDKSDEKPSYCNSRRCKKTFRQCSNGRCVSNMLWCNGADDCGDGSDEIPCNKTAC GVGEFRCRDGTCIGNSSRCNQFVDCEDASDEMNCSATDCSSYFRLGVKGVLFQPCERTSLCYAPSWVCDGANDCGDYSDERDCPG VKRPRCPLNYFACPSGRCIPMSWTCDKEDDCEHGEDETHCNKFCSEAQFECQNHRCISKQWLCDGSDDCGDGSDEAAHCEGKTCG PSSFSCPGTHVCVPERWLCDGDKDCADGADESIAAGCLYNSTCDDREFMCQNRQCIPKHFVCDHDRDCADGSDESPECEYPTCGP SEFRCANGRCLSSRQWECDGENDCHDQSDEAPKNPHCTSQEHKCNASSQFLCSSGRCVAEALLCNGQDDCGDSSDERGCHINECL SRKLSGCSQDCEDLKIGFKCRCRPGFRLKDDGRTCADVDECSTTFPCSQRCINTHGSYKCLCVEGYAPRGGDPHSCKAVTDEEPF LIFANRYYLRKLNLDGSNYTLLKQGLNNAVALDFDYREQMIYWTDVTQGSMIRRMHLNGSNVQVLHRTGLSNPDGLAVDWVGGN LYWCDKGRDTIEVSKLNGAYRTVLVSSGLREPRALVVDVQNGYLYWTDWGDHSLIGRIGMDGSSRSVIVDTKITWPNGLTLDYVT ERIYWADAREDYIEFASLDGSNRHVVLSQDIPHIFALTLFEDYVYWTDWETKSINRAHKTTGTNKTLLISTLHRPMDLHVFHALR QPDVPNHPCKVNNGGCSNLCLLSPGGGHKCACPTNFYLGSDGRTCVSNCTASQFVCKNDKCIPFWWKCDTEDDCGDHSDEPPDCP EFKCRPGQFQCSTGICTNPAFICDGDNDCQDNSDEANCDIHVCLPSQFRCKCTNTNRCIPGIFRCNGQDNCGDGEDERDCPEVTCAP NQFQCSITKRCIPRVWVCDRDNDCVDGSDEPANCTQMTCGVDEFRCKDSGRCIPARWKCDGEDDCGDGSDEPKEECDERTCEPYQ FRCKNNRCVPGRWQCDYDNDCGDNSDEESCTPRPCSESEEFSCANGRCIAGRWKCDGDHDCADGSDEKDCTPRCDMDQFQCKSGHC IPLRWRCDADADCMDGSDEEACGTGVRTCPLDEFQCNNTLCKPLAWKCDGEDDCGDNSDENPEECARFVCPPNRPFRCKNDRVCL WIGRQCDGTDNCGDTDEEDCEPPTAHTTHCKDKKEFLCRNQRCLSDSFVCDHDDCKDGSDEKGCGDSTSCPLNEFTCSNGRCISSS ARCVRTEKAAYCACRSGFHTVPGQPGCQDINECLRFGTCSQLCNNTKGGHLCSCARNFMKTHNTCKAEGSEYQVLYIADDNEIRS LFPGHPHSAYEQAFQGDESVRIDAMDVHVKAGRVYWTNWHGTISYRSLPPAAPPTTSNRHRRQIDRGVTHLNISGLKMPRGIAI DWVAGNVYWTDSGRDVIEVAQMKGENRKTLISGMIDEPHAIVVDPLRGTMYWSDWGNHPKIETAAMDGTLRETLVQDNIQWPTGL AVDYHNERLYWADAKLSVIGSIRLNGTDPIVAADSKRGLSHPFSIDVFEDYIYGVTYINNRVFKIHKFGHSPLVNLTGGLSHASD VVLYHQHKQPEVTNPCDRKKCEWLCLLSPSGPVCTCPNGKRLDNGTCVPVPSPTPPPDAPRPGTCNLQCFNGGSCFLNARRQPKC RCQPRYTGDKCELDQCWEHCRNGGTCAASPSGMPTCRCPT GFTGPKCTQQVCAGYCANNSTCTVNQGNQPQCRCLPGFLGDRCQYRQCSGYCENFGTCQMAADGSRQCRCTAYFEGSRCEVNKCS RCLEGACVVNKQSGDVTCNCTDGRVAPSCLTCVGHCSNGGSCTMNSKMMPECQCPPHMTGPRCEEHVFSQQQPGHIASILIPLLL LLLLVLVAGVVFWYKRRVQGAKGFQHQRMTNGAMNVEIGNPTYKMYEGGEPDDVGGLLDADFALDPDKPTNFTNPVYATLYMGGH GSRHSLASTDEKRELLGRGPEDEIGDPLA | 16 |
| PEDF_HUMAN | MQALVLLLCIGALLGHSSCQNPASPPEEGSPDPDSTGALVEEEDPFFKVPVNKLAAAVSNFGYDLYRVRSSTSPTTNVLLSPLSV ATALSALSLGAEQRTESIIHRALYYDLISSPDIHGTYKELLDTVTAPQKNLKSASRIVFEKKLRIKSSFVAPLEKSYGTRPRVLT GNPRLDLQEINNWVQAQMKGKLARSTKEIPDEISILLLGVAHFKGQWVTKFDSRKTSLEDFYLDEERTVRVPMMSDPKAVLRYGL DSDLSCKIAQLPLTGSMSIIFFLPLKVTQNLTLIEESLTSEFIHDIDRELKTVQAVLTVPKLKLSYEGEVTKSLQEMKLQSLFDS PDFSKITGKPIKLTQVEHRAGFEWNEDGAGTTPSPGLQPAHLTFPLDYHLNQPFIFVLRDTDTGALLFIGKILDPRGP | 17 |
| LUM_HUMAN | MSLSAFTLFLALIGGTSGQYYDYDFPLSIYGQSSPNCAPECNCPESYPSAMYCDELKLKSVPMVPPGIKYLYLRNNQIDHIDEKA FENVTDLQWLILDHNLLENSKIKGRVFSKLKQLKKLHINHNNLTESVGPLPKSLEDLQLTHNKITKLGSFEGLVNLTFIHLQHNR LKEDAVSAAFKGLKSLEYLDLSFNQIARLPSGLPVSLLTLYLDNNKISNIPDEYFKRFNALQYLRLSHNELADSGIPGNSFNVSS LVELDLSYNKLKNIPTVNENLENYYLEVNQLEKFDIKSFCKILGPLSYSKIKHLRLDGNRISETSLPPDMYECLRVANEVTLN | 18 |
| C163A_HUMAN | MSKLRMVLLEDSGSADFRRHFVNLSPFTITVVLLLSACFVTSSLGGTDKELRLVDGENKCSGRVEVKVQEEWGTVCNNGWSMEAV SVICNQLGCPTAIKAPGWANSSAGSGRIWMDHVSCRGNESALWDCKHDGWGKHSNCTHQQDAGVTCSDGSNLEMRLTRGGNMCSG RIEIKFQGRWGTVCDDNFNIDHASVICRQLECGSAVSFSGSSNFGEGSGPIWFDDLICNGNESALWNCKHQGWGKHNCDHAEDAG VICSKGADLSLRLVDGVTECSGRLEVRFQGEWGTICDDGWDSYDAAVACKQLGCPTAVTAIGRVNASKGFGHIWLDSVSCQGHEP | 19 |

TABLE 9-continued

Amino Acid Sequences for Proteins of Interest

| Protein Name | Amino Acid Sequences | Seq. ID. |
|---|---|---|
| | AIWQCKHHEWGKHYCNHNEDAGVTCSDGSDLELRLRGGGSRCAGTVEVEIQRLLGKVCDRGWGLKEADVVCRQLGCGSALKTSYQ VYSKIQATNTWLFLSSCNGNETSLWDCKNWQWGGLTCDHYEEAKITCSAHREPRLVGGDIPCSGRVEVKHGDTWGSICDSDFSLE AASVLCRELQCGTVVSILGGAHFGEGNGQIWAEEFQCEGHESHLSLCPVAPRPEGTCSHSRDVGVVCSRYTEIRLVNGKTPCEGR VELKTLGAWGSLCNSHWDIEDAHVLCQQLKCGVALSTPGGARFGKGNGQIWRHMFHCTGTEQHMGDCPVTALGASLCPSEQVASV ICSGNQSQTLSSCNSSSLGPTRPTIPEESAVACIESGQLRLVNGGGRCAGRVEIYHEGSWGTICDDSWDLSDAHVVCRQLGCGEA INATGSAHFGEGTGPIWLDEMKCNGKESRIWQCHSHGWGQQNCRHKEDAGVICSEFMSLRLTSEASREACAGRLEVFYNGAWGTV GKSSMSETTVGVVCRQLGCADKGKINPASLDKAMSIPMWVDNVQCPKGPDTLWQCPSSPWEKRLASPSEETWITCDNKIRLQEGP TSCSGRVEIWHGGSWGTVCDDSWDLDDAQVVCQQLGCGPALKAFKEAEFGQGTGPIWLNEVKCKGNESSLWDCPARRWGHSECGH KEDAAVNCTDISVQKTPQKATTGRSSRQSSFIAVGILGVVLLAIFVALFFLTKKRRQRQRLAVSSRGENLVHQIQYREMNSCLNA DDLDLMNSSENSHESADFSAAELISVSKFLPISGMEKEAILSHTEKENGNL | |
| PTPRJ_HUMAN | MKPAAREARLPPRSPGLRWALPLLLLLRLGQILCAGGTPSPIPDPSVATVATGENGITQISSTAESFHKQNGTGTPQVETNTSE DGESSGANDSLRTPEQGSNGTDGASQKTPSSTGPSPVFDIKAVSISPTNVILTWKSNDTAASEYKYVVKHKMENEKTITVVHQPW CNITGLRPATSYVFSITPGIGNETWGDPRVIKVITEPIPVSDLRVALTGVRKAALSWSNGNGTASCRVLLESIGSHEELTQDSRL QVNISGLKPGVQYNINPYLLQSNKTKGDPLGTEGGLDASNTERSRAGSPTAPVHDESLVGPVDPSSGQQSRDTEVLLVGLEPGTR YNATVYSQAANGTEGQPQAIEFRTNAIQVFDVTAVNISATSLTLIWKVSDNESSSNYTYKIHVAGETDSSNLNVSEPRAVIPGLR SSTFYNITVCPVLGDIEGTPGFLQVHTPPVPVSDFRVTVVSSTTEIGLAWSSHDAESFQMHITQEGAGNSRVEITTNQSIIIGGLF PGTKYCFEIVPKGPNGTEGASRTVCNRTVPSAVFDIHVVYVTTTEMWLDWKSPDGASEYVYHLVIESKHGSNHTSTYDKAITLQG LIPGTLYNITISPEVDHVWGDPNSTAQYTRPSNVSNIDVSTNTTAATLSWQNFDDASPTYSYCLLIEKAGNSSNATQVVTDIGIT DATVTELIPGSSYTVEIFAQVGDGIKSLEPGRKSFCTDPSMASFDCEVVPKEPALVLKWTCPPGANAGFELEVSSGAWNNATHL ESCSSENGTEYRTEVTYLNFSTSYNISITTVSCGKMAAPTRNTCTTGITDPPPPDGSPNITSVSHNSVKVKFSGFEASHGPIKAY AVILTTGEAGHPSADVLKYTYEDFKKGASDTYVTYLIRTEEKGRSQSLSEVLKYEIDVGNESTTLGYYNGKLEPLGSYRACVAGF TNITFHPQNKGLIDGAESYVSFSRYSDAVSLPQDPGVICGAVFGCIFGALVIVTGGGFIFWRKKRKDAKNNEVSFSQIKPKKSKL IRVENFEAYFKKQQADSNCGFAEEYEDLKLVGISQPKYAAELAENRGKNRYNNVLPYDISRVKLSVQTHSTDDYINANYMPGYHS KKDFIATQGGPLPNTLKDFWRMVWEKNVYAIIMLTKCVEQGRTKCEEYWPSKQAQDYGDITVAMTSEIVLPENTIRDFTVKNIQTS ESHPLRQFHFTSWPDHGVPDTTDLLINFRYLVRDYMKQSPPESPILVHCSAGVGRTGFTIAIDRLIYQIENENTVDVYGIVYDLR MHRPLMVQTEDQYVFLNQCVLDIVRSQKDSKVDLIYQNTTAMTIYENLAPVTTFGKTNGYIA | 20 |
| ALDOA_HUMAN | MPYQYPALTPEQKKELSDIAHRIVAPGKGILAADESTGSIAKRLQSIGTENTEENRRFYRQLLLTADDRVNPCIGGVILFHETLY QKADDGRPFPQVIKSKGGVVGIKVDKGVVPLAGTNGETTTQGLDGLSERCAQYKKDGADFAKWRCVLKIGEHTPSALAIMENANV LARYASICQQNGIVPIVEPEILPDGDHDLKRCQYVTEKVLAAVYKALSDHHIYLEGTLLKPNMVTPGHACTQKFSHEEIAMATVT ALRRTVPPAVTGITFLSGGQSEEEASINLNAINKCPLLKPWALTFSYGRALQASALKAWGGKKENLKAAQEEYVKRALANSLACQ GKYTPSGQAGAAASESLFVSNHAY | 21 |
| FRIL_HUMAN | MSSQIRQNYSTDVEAAVNSLVNLYLQASYTYLSLGFYFDRDDVALEGVSHFFRELAEEKREGYERLLKMQNQRGGRALFQDIKKP AEDEWGKTPDAMKAAMALEKKLNQALLDLHALGSARTDPHLCDFLETHFLDEEVKLIKKMGDHLTNLHRLGGPEAGLGEYLFERL TLKHD | 22 |
| TETN_HUMAN | MELWGAYLLLCLFSLLTQVTTEPPTQKPKKIVNAKKDVVNTKMFEELKSRLDTLAQEVALLKEQQALQTVCLKGTKVHMKCFLAF TQTKTFHEASEDCISRGGTLGTPQTGSENDALYEYLRQSVGNEAEIWLGLNDMAAEGTWVDMTGARIAYKNWETEITAPQPDGGKT ENCAVLSGAANGKWFDKRCRDQLPYICQFGIV | 23 |
| ISLR_HUMAN | MQELHLLWWALLLLGLAQACPEPCDCGEKYGFQIADCAYRDLESVPPGFPANVTTLSLSANRLPGLPEGAFREVPLLQSLWLAHNE IRTVAAGALASLSHLKSLDLSHNLISDFAWSDHNLSALQLLKMDSNELTFIPRDAFRSLRALRSLQLNHNRLHTLAEGTFTPLT ALSHLQINENPFDCTCGIVWLKTWALTTAVSIPEQDNIACTSPHVLKGTPLSRLPPLPCSAPSVQLSYQPSQDGAELRPGFVLAL HCDVDGQPAPQLHWHIQIPSGIVEITSPNVGTDGRALPGTPVASSQPRFQAFANGSLLIPDFGKLEEGTYSCLATNELGSAESSV DVALATPGEGGEDTLGRRFHGKAVEGKGCYTVDNEVQPSGPEDNVVIIYLSRAGNPEAAVAEGVPGQLPPGLLLLGQSLLLFFFL TSF | 24 |

The invention claimed is:

1. A method for determining the expression level of target proteins in a subject, comprising:
   generating a plurality of respective peptide transitions from a plurality of proteins obtained from a biological sample from the subject, wherein the plurality of proteins comprises both target and normalizing proteins;
   measuring a mass spectroscopy (MS) signal intensity from the respective plurality of peptide transitions and a plurality of corresponding stable isotope-labeled internal standard (SIS) peptide transitions;
   for each of the plurality of proteins, calculating a response ratio between the MS signal intensity of the peptide transition and the corresponding SIS peptide transition;
   calculating a sample-dependent normalization factor from the response ratios for the normalizing proteins; wherein the normalizing proteins are selected based on their ability to reduce intensity drift (D) of each of the plurality of respective peptide transitions, wherein intensity drift determines the deviation in abundance of each peptide transition from the overall median abundance of each peptide transition and
   normalizing the response ratio for each target protein by the sample-dependent normalization factor, wherein the normalized response ratios provide a determination of the expression level of the target proteins.

2. The method of claim 1, wherein the determination of the expression level of the target proteins provides a diagnosis of lung disease for the subject.

3. The method of claim 1, wherein the normalizing proteins are selected based on their ability to reduce the median technical coefficient of variation (CV) of the plurality of proteins.

4. The method of claim 1, wherein the plurality of proteins comprise at least two normalizing proteins selected from the group consisting of PEDF_HUMAN (Pigment epithelium-derived factor), MASP1_HUMAN (Mannan-binding lectin serine protease 1), GELS_HUMAN (Gelsolin), LUM_HUMAN (Lumican), C163A_HUMAN (Scavenger receptor cysteine-rich type 1 protein M130), and PTPRJ_HUMAN (Receptor-type tyrosine-protein phosphatase eta).

5. The method of claim 4, wherein the plurality of proteins comprise six normalizing proteins including PEDF_HUMAN, MASP1_HUMAN, GELS_HUMAN, LUM_HUMAN, C163A_HUMAN, and PTPRJ_HUMAN.

6. The method of claim 5, wherein the plurality of respective peptide transitions comprise LQSLFDSPDFSK (SEQ ID NO: 25) (692.34, 593.30), TGVITSPDFPNPYPK (SEQ ID NO: 26) (816.92, 258.10), TASDFITK (SEQ ID NO: 27) (441.73, 710.40), SLEDLQLTHNK (SEQ ID NO: 28) (433.23, 499.30), INPASLDK (SEQ ID NO: 29) (429.24, 630.30), and VITEPIPVSDLR (SEQ ID NO: 30) (669.89, 896.50).

7. The method of claim 1, wherein the target proteins comprise at least five of KIT_HUMAN (Mast/stem cell growth factor receptor), FRIL_HUMAN (Ferritin light chain), COIA1_HUMAN (Collagen alpha-1(XVIII) chain), PRDX1_HUMAN (Peroxiredoxin-1), TENX_HUMAN (Tenascin-X), ENPL_HUMAN (Endoplasmin), GRP78_HUMAN (78 kDa glucose-regulated protein), BGH3_HUMAN (Transforming growth factor-beta-induced protein ig-h3), ALDOA_HUMAN (Fructose-bisphosphate aldolase A), GGH_HUMAN (Gamma-glutamyl hydrolase), CD14_HUMAN (Monocyte differentiation antigen CD14), LG3BP_HUMAN (Galectin-3-binding protein), TSP1_HUMAN (Thrombospondin-1), IBP3_HUMAN (Insulin-like growth factor-binding protein 3), TETN_HUMAN (Tetranectin), and ISLR_HUMAN (Immunoglobulin superfamily containing leucine-rich repeat protein).

8. The method of claim 7, wherein the target proteins comprise ALDOA_HUMAN, FRIL_HUMAN, COIA1_HUMAN, LG3BP_HUMAN, and TSP1_HUMAN.

9. The method of claim 7, wherein the target proteins comprise ALDOA_HUMAN, FRIL_HUMAN, KIT_HUMAN, GGH_HUMAN, and TSP1_HUMAN.

10. The method of claim 7, wherein the target proteins comprise KIT_HUMAN, FRIL_HUMAN, COIA1_HUMAN, PRDX_HUMAN, TENX_HUMAN, ENPL_HUMAN, TENX_HUMAN, ENPL_HUMAN, GRP78_HUMAN, BGH3_HUMAN, ALDOA_HUMAN, GGH_HUMAN, CD14_HUMAN, LG3BP_HUMAN, IBP3_HUMAN, TETN_HUMAN, and ISLR_HUMAN.

11. The method of claim 1, wherein the biological sample is selected from the group consisting of tissue, blood, plasma, serum, whole blood, urine, saliva, genital secretion, cerebrospinal fluid, sweat and excreta.

12. The method of claim 1, wherein the plurality of proteins are obtained by immunoaffinity depletion.

13. The method of claim 12, wherein the measuring step is performed by selected reaction monitoring mass spectrometry (SRM-MS).

14. The method of claim 1, wherein the plurality of respective peptide transitions are generated by enzymatically digesting the plurality of proteins.

15. The method of claim 1, wherein the response ratio (R) is defined as:

$$R_{p,s} = A_{p,s}/\hat{A}_{p,s}$$

where $A_{p,s}$ is the peak area of the signal intensity of peptide transition p in the biological sample s, and $\hat{A}_{p,s}$ is the peak area of the signal intensity the corresponding SIS peptide transition.

16. The method of claim 15, wherein the normalized response ratio ($\tilde{R}$) is defined as:

$$\tilde{R}_{p,s} = R_{p,s}/S_s^I,$$

where p is peptide transition, s is the biological sample, $R_{p,s}$ is the response ratio of peptide p in biological sample s, and $S_s^I$ is the sample-dependent normalization factor.

17. The method of claim 1, wherein the sample-dependent normalization factor (S) is defined as:

$$S_s^I = \text{median}\left(\frac{R_{1,s}}{\tilde{R}_1}, \frac{R_{2,s}}{\tilde{R}_2}, \ldots, \frac{R_{N,s}}{\tilde{R}_N}\right)$$

where $S_s^I$ is the sample-dependent normalization factor calculated from the response ratios (R) of the N peptide transitions from normalizing proteins in the biological sample s, where $R_{n,s}$ is response ratio of peptide transitions from normalizing proteins n in the sample and $\check{R}_n$ is a scaling constant for the peptide normalizer that ensures values of $\{R_{n,s}/\check{R}_n\}$ among all peptide transitions from normalizing proteins to be same on average.

18. The method of claim 1, wherein intensity drift (D) is defined by:

$$D_{p,s} = (I_{p,s} - \check{I}_p)/\check{I}_p$$

where p is peptide transition, s is the biological sample, $I_{p,s}$ is the abundance of peptide transition p in the sample s, and $\check{I}_p$ is the corresponding median value in all technical replica.

19. The method of claim 1, wherein the plurality of respective peptide transitions and the plurality of corresponding stable isotope-labeled internal standard (SIS) peptide transitions are mixed together within a sample prior to the measuring step.

20. The method of claim 19, wherein the determination of the expression level of the target proteins is independent of the volume of the sample.

21. The method of claim 1, wherein the subject has a lung condition.

22. The method of claim 21, wherein the lung condition is cancer or a non-cancerous lung condition.

* * * * *

SEQUENCE LISTING

<160> NUMBER OF SEQ ID NOS: 48

<210> SEQ ID NO 1
<211> LENGTH: 683
<212> TYPE: PRT
<213> ORGANISM: Homo sapiens

<400> SEQUENCE: 1

Met Ala Leu Phe Val Arg Leu Leu Ala Leu Ala Leu Ala Leu
1               5                   10                  15

Gly Pro Ala Ala Thr Leu Ala Gly Pro Ala Lys Ser Pro Tyr Gln Leu
                20                  25                  30

Val Leu Gln His Ser Arg Leu Arg Gly Arg Gln His Gly Pro Asn Val
            35                  40                  45

Cys Ala Val Gln Lys Val Ile Gly Thr Asn Arg Lys Tyr Phe Thr Asn

```
                  50                  55                  60
Cys Lys Gln Trp Tyr Gln Arg Lys Ile Cys Gly Lys Ser Thr Val Ile
 65                  70                  75                  80

Ser Tyr Glu Cys Cys Pro Gly Tyr Glu Lys Val Pro Gly Glu Lys Gly
                 85                  90                  95

Cys Pro Ala Ala Leu Pro Leu Ser Asn Leu Tyr Glu Thr Leu Gly Val
                100                 105                 110

Val Gly Ser Thr Thr Thr Gln Leu Tyr Thr Asp Arg Thr Glu Lys Leu
                115                 120                 125

Arg Pro Glu Met Glu Gly Pro Gly Ser Phe Thr Ile Phe Ala Pro Ser
                130                 135                 140

Asn Glu Ala Trp Ala Ser Leu Pro Ala Glu Val Leu Asp Ser Leu Val
145                 150                 155                 160

Ser Asn Val Asn Ile Glu Leu Leu Asn Ala Leu Arg Tyr His Met Val
                165                 170                 175

Gly Arg Arg Val Leu Thr Asp Glu Leu Lys His Gly Met Thr Leu Thr
                180                 185                 190

Ser Met Tyr Gln Asn Ser Asn Ile Gln Ile His His Tyr Pro Asn Gly
                195                 200                 205

Ile Val Thr Val Asn Cys Ala Arg Leu Leu Lys Ala Asp His His Ala
                210                 215                 220

Thr Asn Gly Val Val His Leu Ile Asp Lys Val Ile Ser Thr Ile Thr
225                 230                 235                 240

Asn Asn Ile Gln Gln Ile Ile Glu Ile Glu Asp Thr Phe Glu Thr Leu
                245                 250                 255

Arg Ala Ala Val Ala Ala Ser Gly Leu Asn Thr Met Leu Glu Gly Asn
                260                 265                 270

Gly Gln Tyr Thr Leu Leu Ala Pro Thr Asn Glu Ala Phe Glu Lys Ile
                275                 280                 285

Pro Ser Glu Thr Leu Asn Arg Ile Leu Gly Asp Pro Glu Ala Leu Arg
                290                 295                 300

Asp Leu Leu Asn Asn His Ile Leu Lys Ser Ala Met Cys Ala Glu Ala
305                 310                 315                 320

Ile Val Ala Gly Leu Ser Val Glu Thr Leu Glu Gly Thr Thr Leu Glu
                325                 330                 335

Val Gly Cys Ser Gly Asp Met Leu Thr Ile Asn Gly Lys Ala Ile Ile
                340                 345                 350

Ser Asn Lys Asp Ile Leu Ala Thr Asn Gly Val Ile His Tyr Ile Asp
                355                 360                 365

Glu Leu Leu Ile Pro Asp Ser Ala Lys Thr Leu Phe Glu Leu Ala Ala
                370                 375                 380

Glu Ser Asp Val Ser Thr Ala Ile Asp Leu Phe Arg Gln Ala Gly Leu
385                 390                 395                 400

Gly Asn His Leu Ser Gly Ser Glu Arg Leu Thr Leu Leu Ala Pro Leu
                405                 410                 415

Asn Ser Val Phe Lys Asp Gly Thr Pro Pro Ile Asp Ala His Thr Arg
                420                 425                 430

Asn Leu Leu Arg Asn His Ile Ile Lys Asp Gln Leu Ala Ser Lys Tyr
                435                 440                 445

Leu Tyr His Gly Gln Thr Leu Glu Thr Leu Gly Gly Lys Lys Leu Arg
                450                 455                 460

Val Phe Val Tyr Arg Asn Ser Leu Cys Ile Glu Asn Ser Cys Ile Ala
465                 470                 475                 480
```

```
Ala His Asp Lys Arg Gly Arg Tyr Gly Thr Leu Phe Thr Met Asp Arg
            485                 490                 495

Val Leu Thr Pro Pro Met Gly Thr Val Met Asp Val Leu Lys Gly Asp
            500                 505                 510

Asn Arg Phe Ser Met Leu Val Ala Ala Ile Gln Ser Ala Gly Leu Thr
            515                 520                 525

Glu Thr Leu Asn Arg Glu Gly Val Tyr Thr Val Phe Ala Pro Thr Asn
    530                 535                 540

Glu Ala Phe Arg Ala Leu Pro Pro Arg Glu Arg Ser Arg Leu Leu Gly
545                 550                 555                 560

Asp Ala Lys Glu Leu Ala Asn Ile Leu Lys Tyr His Ile Gly Asp Glu
                565                 570                 575

Ile Leu Val Ser Gly Ile Gly Ala Leu Val Arg Leu Lys Ser Leu
                580                 585                 590

Gln Gly Asp Lys Leu Glu Val Ser Leu Lys Asn Asn Val Val Ser Val
                595                 600                 605

Asn Lys Glu Pro Val Ala Glu Pro Asp Ile Met Ala Thr Asn Gly Val
            610                 615                 620

Val His Val Ile Thr Asn Val Leu Gln Pro Pro Ala Asn Arg Pro Gln
625                 630                 635                 640

Glu Arg Gly Asp Glu Leu Ala Asp Ser Ala Leu Glu Ile Phe Lys Gln
                645                 650                 655

Ala Ser Ala Phe Ser Arg Ala Ser Gln Arg Ser Val Arg Leu Ala Pro
                660                 665                 670

Val Tyr Gln Lys Leu Leu Glu Arg Met Lys His
            675                 680

<210> SEQ ID NO 2
<211> LENGTH: 318
<212> TYPE: PRT
<213> ORGANISM: Homo sapiens

<400> SEQUENCE: 2

Met Ala Ser Pro Gly Cys Leu Leu Cys Val Leu Gly Leu Leu Leu Cys
1               5                   10                  15

Gly Ala Ala Ser Leu Glu Leu Ser Arg Pro His Gly Asp Thr Ala Lys
            20                  25                  30

Lys Pro Ile Ile Gly Ile Leu Met Gln Lys Cys Arg Asn Lys Val Met
        35                  40                  45

Lys Asn Tyr Gly Arg Tyr Tyr Ile Ala Ala Ser Tyr Val Lys Tyr Leu
50                  55                  60

Glu Ser Ala Gly Ala Arg Val Val Pro Val Arg Leu Asp Leu Thr Glu
65                  70                  75                  80

Lys Asp Tyr Glu Ile Leu Phe Lys Ser Ile Asn Gly Ile Leu Phe Pro
                85                  90                  95

Gly Gly Ser Val Asp Leu Arg Arg Ser Asp Tyr Ala Lys Val Ala Lys
            100                 105                 110

Ile Phe Tyr Asn Leu Ser Ile Gln Ser Phe Asp Asp Gly Asp Tyr Phe
        115                 120                 125

Pro Val Trp Gly Thr Cys Leu Gly Phe Glu Glu Leu Ser Leu Leu Ile
    130                 135                 140

Ser Gly Glu Cys Leu Leu Thr Ala Thr Asp Thr Val Asp Val Ala Met
145                 150                 155                 160

Pro Leu Asn Phe Thr Gly Gly Gln Leu His Ser Arg Met Phe Gln Asn
```

-continued

```
                165                 170                 175
Phe Pro Thr Glu Leu Leu Ser Leu Ala Val Glu Pro Leu Thr Ala
            180                 185                 190

Asn Phe His Lys Trp Ser Leu Ser Val Lys Asn Phe Thr Met Asn Glu
            195                 200                 205

Lys Leu Lys Lys Phe Phe Asn Val Leu Thr Thr Asn Thr Asp Gly Lys
210                 215                 220

Ile Glu Phe Ile Ser Thr Met Glu Gly Tyr Lys Tyr Pro Val Tyr Gly
225                 230                 235                 240

Val Gln Trp His Pro Glu Lys Ala Pro Tyr Glu Trp Lys Asn Leu Asp
            245                 250                 255

Gly Ile Ser His Ala Pro Asn Ala Val Lys Thr Ala Phe Tyr Leu Ala
            260                 265                 270

Glu Phe Phe Val Asn Glu Ala Arg Lys Asn Asn His His Phe Lys Ser
            275                 280                 285

Glu Ser Glu Glu Glu Lys Ala Leu Ile Tyr Gln Phe Ser Pro Ile Tyr
            290                 295                 300

Thr Gly Asn Ile Ser Ser Phe Gln Gln Cys Tyr Ile Phe Asp
305                 310                 315

<210> SEQ ID NO 3
<211> LENGTH: 585
<212> TYPE: PRT
<213> ORGANISM: Homo sapiens

<400> SEQUENCE: 3

Met Thr Pro Pro Arg Leu Phe Trp Val Trp Leu Leu Val Ala Gly Thr
1               5                   10                  15

Gln Gly Val Asn Asp Gly Asp Met Arg Leu Ala Asp Gly Gly Ala Thr
            20                  25                  30

Asn Gln Gly Arg Val Glu Ile Phe Tyr Arg Gly Gln Trp Gly Thr Val
        35                  40                  45

Cys Asp Asn Leu Trp Asp Leu Thr Asp Ala Ser Val Val Cys Arg Ala
50                  55                  60

Leu Gly Phe Glu Asn Ala Thr Gln Ala Leu Gly Arg Ala Ala Phe Gly
65                  70                  75                  80

Gln Gly Ser Gly Pro Ile Met Leu Asp Glu Val Gln Cys Thr Gly Thr
            85                  90                  95

Glu Ala Ser Leu Ala Asp Cys Lys Ser Leu Gly Trp Leu Lys Ser Asn
            100                 105                 110

Cys Arg His Glu Arg Asp Ala Gly Val Val Cys Thr Asn Glu Thr Arg
        115                 120                 125

Ser Thr His Thr Leu Asp Leu Ser Arg Glu Leu Ser Glu Ala Leu Gly
    130                 135                 140

Gln Ile Phe Asp Ser Gln Arg Gly Cys Asp Leu Ser Ile Ser Val Asn
145                 150                 155                 160

Val Gln Gly Glu Asp Ala Leu Gly Phe Cys Gly His Thr Val Ile Leu
            165                 170                 175

Thr Ala Asn Leu Glu Ala Gln Ala Leu Trp Lys Glu Pro Gly Ser Asn
            180                 185                 190

Val Thr Met Ser Val Asp Ala Glu Cys Val Pro Met Val Arg Asp Leu
        195                 200                 205

Leu Arg Tyr Phe Tyr Ser Arg Arg Ile Asp Ile Thr Leu Ser Ser Val
    210                 215                 220
```

```
Lys Cys Phe His Lys Leu Ala Ser Ala Tyr Gly Ala Arg Gln Leu Gln
225                 230                 235                 240

Gly Tyr Cys Ala Ser Leu Phe Ala Ile Leu Leu Pro Gln Asp Pro Ser
            245                 250                 255

Phe Gln Met Pro Leu Asp Leu Tyr Ala Tyr Ala Val Ala Thr Gly Asp
        260                 265                 270

Ala Leu Leu Glu Lys Leu Cys Leu Gln Phe Leu Ala Trp Asn Phe Glu
    275                 280                 285

Ala Leu Thr Gln Ala Glu Ala Trp Pro Ser Val Pro Thr Asp Leu Leu
290                 295                 300

Gln Leu Leu Pro Arg Ser Asp Leu Ala Val Pro Ser Glu Leu Ala
305                 310                 315                 320

Leu Leu Lys Ala Val Asp Thr Trp Ser Trp Gly Glu Arg Ala Ser His
            325                 330                 335

Glu Glu Val Glu Gly Leu Val Glu Lys Ile Arg Phe Pro Met Met Leu
        340                 345                 350

Pro Glu Glu Leu Phe Glu Leu Gln Phe Asn Leu Ser Leu Tyr Trp Ser
    355                 360                 365

His Glu Ala Leu Phe Gln Lys Lys Thr Leu Gln Ala Leu Glu Phe His
370                 375                 380

Thr Val Pro Phe Gln Leu Leu Ala Arg Tyr Lys Gly Leu Asn Leu Thr
385                 390                 395                 400

Glu Asp Thr Tyr Lys Pro Arg Ile Tyr Thr Ser Pro Thr Trp Ser Ala
            405                 410                 415

Phe Val Thr Asp Ser Ser Trp Ser Ala Arg Lys Ser Gln Leu Val Tyr
        420                 425                 430

Gln Ser Arg Arg Gly Pro Leu Val Lys Tyr Ser Ser Asp Tyr Phe Gln
    435                 440                 445

Ala Pro Ser Asp Tyr Arg Tyr Tyr Pro Tyr Gln Ser Phe Gln Thr Pro
450                 455                 460

Gln His Pro Ser Phe Leu Phe Gln Asp Lys Arg Val Ser Trp Ser Leu
465                 470                 475                 480

Val Tyr Leu Pro Thr Ile Gln Ser Cys Trp Asn Tyr Gly Phe Ser Cys
            485                 490                 495

Ser Ser Asp Glu Leu Pro Val Leu Gly Leu Thr Lys Ser Gly Gly Ser
        500                 505                 510

Asp Arg Thr Ile Ala Tyr Glu Asn Lys Ala Leu Met Leu Cys Glu Gly
    515                 520                 525

Leu Phe Val Ala Asp Val Thr Asp Phe Glu Gly Trp Lys Ala Ala Ile
530                 535                 540

Pro Ser Ala Leu Asp Thr Asn Ser Ser Lys Ser Thr Ser Ser Phe Pro
545                 550                 555                 560

Cys Pro Ala Gly His Phe Asn Gly Phe Arg Thr Val Ile Arg Pro Phe
            565                 570                 575

Tyr Leu Thr Asn Ser Ser Gly Val Asp
        580                 585

<210> SEQ ID NO 4
<211> LENGTH: 199
<212> TYPE: PRT
<213> ORGANISM: Homo sapiens

<400> SEQUENCE: 4

Met Ser Ser Gly Asn Ala Lys Ile Gly His Pro Ala Pro Asn Phe Lys
1               5                   10                  15
```

-continued

```
Ala Thr Ala Val Met Pro Asp Gly Gln Phe Lys Asp Ile Ser Leu Ser
             20                  25                  30

Asp Tyr Lys Gly Lys Tyr Val Val Phe Phe Tyr Pro Leu Asp Phe
         35                  40                  45

Thr Phe Val Cys Pro Thr Glu Ile Ile Ala Phe Ser Asp Arg Ala Glu
 50                  55                  60

Glu Phe Lys Lys Leu Asn Cys Gln Val Ile Gly Ala Ser Val Asp Ser
 65                  70                  75                  80

His Phe Cys His Leu Ala Trp Val Asn Thr Pro Lys Lys Gln Gly Gly
                 85                  90                  95

Leu Gly Pro Met Asn Ile Pro Leu Val Ser Asp Pro Lys Arg Thr Ile
             100                 105                 110

Ala Gln Asp Tyr Gly Val Leu Lys Ala Asp Glu Gly Ile Ser Phe Arg
         115                 120                 125

Gly Leu Phe Ile Ile Asp Asp Lys Gly Ile Leu Arg Gln Ile Thr Val
130                 135                 140

Asn Asp Leu Pro Val Gly Arg Ser Val Asp Glu Thr Leu Arg Leu Val
145                 150                 155                 160

Gln Ala Phe Gln Phe Thr Asp Lys His Gly Glu Val Cys Pro Ala Gly
                 165                 170                 175

Trp Lys Pro Gly Ser Asp Thr Ile Lys Pro Asp Val Gln Lys Ser Lys
             180                 185                 190

Glu Tyr Phe Ser Lys Gln Lys
         195

<210> SEQ ID NO 5
<211> LENGTH: 1170
<212> TYPE: PRT
<213> ORGANISM: Homo sapiens

<400> SEQUENCE: 5

Met Gly Leu Ala Trp Gly Leu Gly Val Leu Phe Leu Met His Val Cys
 1               5                  10                  15

Gly Thr Asn Arg Ile Pro Glu Ser Gly Gly Asp Asn Ser Val Phe Asp
             20                  25                  30

Ile Phe Glu Leu Thr Gly Ala Ala Arg Lys Gly Ser Gly Arg Arg Leu
         35                  40                  45

Val Lys Gly Pro Asp Pro Ser Ser Pro Ala Phe Arg Ile Glu Asp Ala
 50                  55                  60

Asn Leu Ile Pro Pro Val Pro Asp Asp Lys Phe Gln Asp Leu Val Asp
 65                  70                  75                  80

Ala Val Arg Ala Glu Lys Gly Phe Leu Leu Leu Ala Ser Leu Arg Gln
                 85                  90                  95

Met Lys Lys Thr Arg Gly Thr Leu Leu Ala Leu Glu Arg Lys Asp His
             100                 105                 110

Ser Gly Gln Val Phe Ser Val Val Ser Asn Gly Lys Ala Gly Thr Leu
         115                 120                 125

Asp Leu Ser Leu Thr Val Gln Gly Lys Gln His Val Val Ser Val Glu
130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                 165                 170                 175

Ala Glu Leu Asp Val Pro Ile Gln Ser Val Phe Thr Arg Asp Leu Ala
```

-continued

```
            180                 185                 190
Ser Ile Ala Arg Leu Arg Ile Ala Lys Gly Gly Val Asn Asp Asn Phe
        195                 200                 205

Gln Gly Val Leu Gln Asn Val Arg Phe Val Phe Gly Thr Thr Pro Glu
        210                 215                 220

Asp Ile Leu Arg Asn Lys Gly Cys Ser Ser Ser Thr Ser Val Leu Leu
225                 230                 235                 240

Thr Leu Asp Asn Val Val Asn Gly Ser Ser Pro Ala Ile Arg Thr
                    245                 250                 255

Asn Tyr Ile Gly His Lys Thr Lys Asp Leu Gln Ala Ile Cys Gly Ile
                260                 265                 270

Ser Cys Asp Glu Leu Ser Ser Met Val Leu Glu Leu Arg Gly Leu Arg
            275                 280                 285

Thr Ile Val Thr Thr Leu Gln Asp Ser Ile Arg Lys Val Thr Glu Glu
            290                 295                 300

Asn Lys Glu Leu Ala Asn Glu Leu Arg Arg Pro Pro Leu Cys Tyr His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
                340                 345                 350

Cys Pro Ile Met Pro Cys Ser Asn Ala Thr Val Pro Asp Gly Glu Cys
            355                 360                 365

Cys Pro Arg Cys Trp Pro Ser Asp Ser Ala Asp Asp Gly Trp Ser Pro
            370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
            420                 425                 430

Lys Gln Asp Gly Gly Trp Ser His Trp Ser Pro Trp Ser Ser Cys Ser
        435                 440                 445

Val Thr Cys Gly Asp Gly Val Ile Thr Arg Ile Arg Leu Cys Asn Ser
        450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
            500                 505                 510

Gln Lys Arg Ser Arg Leu Cys Asn Asn Pro Thr Pro Gln Phe Gly Gly
        515                 520                 525

Lys Asp Cys Val Gly Asp Val Thr Glu Asn Gln Ile Cys Asn Lys Gln
530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Thr Asp Val Asp Glu Cys
            580                 585                 590

Lys Glu Val Pro Asp Ala Cys Phe Asn His Asn Gly Glu His Arg Cys
        595                 600                 605
```

```
Glu Asn Thr Asp Pro Gly Tyr Asn Cys Leu Pro Cys Pro Arg Phe
    610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
            660                 665                 670

Met Tyr Arg Cys Glu Cys Lys Pro Gly Tyr Ala Gly Asn Gly Ile Ile
        675                 680                 685

Cys Gly Glu Asp Thr Asp Leu Asp Gly Trp Pro Asn Glu Asn Leu Val
    690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asn Asp Lys Ile Pro Asp Asp Arg Asp
            740                 745                 750

Asn Cys Pro Phe His Tyr Asn Pro Ala Gln Tyr Asp Tyr Asp Arg Asp
        755                 760                 765

Asp Val Gly Asp Arg Cys Asp Asn Cys Pro Tyr Asn His Asn Pro Asp
    770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp Gln
            820                 825                 830

Cys Asp Asn Cys Pro Leu Glu His Asn Pro Asp Gln Leu Asp Ser Asp
        835                 840                 845

Ser Asp Arg Ile Gly Asp Thr Cys Asp Asn Asn Gln Asp Ile Asp Glu
    850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Lys Asp Asn Cys Arg Leu
            900                 905                 910

Val Pro Asn Pro Asp Gln Lys Asp Ser Asp Gly Asp Gly Arg Gly Asp
    915                 920                 925

Ala Cys Lys Asp Asp Phe Asp His Asp Ser Val Pro Asp Ile Asp Asp
930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
                965                 970                 975

Trp Val Val Arg His Gln Gly Lys Glu Leu Val Gln Thr Val Asn Cys
            980                 985                 990

Asp Pro Gly Leu Ala Val Gly Tyr Asp Glu Phe Asn Ala Val Asp Phe
        995                 1000                1005

Ser Gly Thr Phe Phe Ile Asn Thr Glu Arg Asp Asp Asp Tyr Ala
    1010                1015                1020
```

```
Gly Phe Val Phe Gly Tyr Gln Ser Ser Arg Phe Tyr Val Val
    1025                1030                1035

Met Trp Lys Gln Val Thr Gln Ser Tyr Trp Asp Thr Asn Pro Thr
1040                1045                1050

Arg Ala Gln Gly Tyr Ser Gly Leu Ser Val Lys Val Val Asn Ser
    1055                1060                1065

Thr Thr Gly Pro Gly Glu His Leu Arg Asn Ala Leu Trp His Thr
1070                1075                1080

Gly Asn Thr Pro Gly Gln Val Arg Thr Leu Trp His Asp Pro Arg
    1085                1090                1095

His Ile Gly Trp Lys Asp Phe Thr Ala Tyr Arg Trp Arg Leu Ser
    1100                1105                1110

His Arg Pro Lys Thr Gly Phe Ile Arg Val Val Met Tyr Glu Gly
    1115                1120                1125

Lys Lys Ile Met Ala Asp Ser Gly Pro Ile Tyr Asp Lys Thr Tyr
    1130                1135                1140

Ala Gly Gly Arg Leu Gly Leu Phe Val Phe Ser Gln Glu Met Val
    1145                1150                1155

Phe Phe Ser Asp Leu Lys Tyr Glu Cys Arg Asp Pro
    1160                1165                1170

<210> SEQ ID NO 6
<211> LENGTH: 742
<212> TYPE: PRT
<213> ORGANISM: Homo sapiens

<400> SEQUENCE: 6

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
                20                  25                  30

Val Phe His Val Glu Lys Asn Gly Arg Tyr Ser Ile Ser Arg Thr Glu
            35                  40                  45

Ala Ala Asp Leu Cys Lys Ala Phe Asn Ser Thr Leu Pro Thr Met Ala
        50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
    210                 215                 220
```

```
Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
            245                 250                 255

His Leu His Thr Thr Thr Gln Met Ala Gly Thr Ser Ser Asn Thr Ile
        260                 265                 270

Ser Ala Gly Trp Glu Pro Asn Glu Glu Asn Glu Asp Glu Arg Asp Arg
    275                 280                 285

His Leu Ser Phe Ser Gly Ser Gly Ile Asp Asp Asp Glu Asp Phe Ile
    290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
            325                 330                 335

Leu Leu Gln Thr Thr Thr Arg Met Thr Asp Val Asp Arg Asn Gly Thr
        340                 345                 350

Thr Ala Tyr Glu Gly Asn Trp Asn Pro Glu Ala His Pro Pro Leu Ile
    355                 360                 365

His His Glu His His Glu Glu Glu Thr Pro His Ser Thr Ser Thr
370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
            405                 410                 415

Lys Glu Asp Ser His Ser Thr Thr Gly Thr Ala Ala Ser Ala His
        420                 425                 430

Thr Ser His Pro Met Gln Gly Arg Thr Thr Pro Ser Pro Glu Asp Ser
    435                 440                 445

Ser Trp Thr Asp Phe Phe Asn Pro Ile Ser His Pro Met Gly Arg Gly
    450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
            485                 490                 495

Arg Thr Gly Pro Leu Ser Met Thr Thr Gln Gln Ser Asn Ser Gln Ser
        500                 505                 510

Phe Ser Thr Ser His Glu Gly Leu Glu Glu Asp Lys Asp His Pro Thr
    515                 520                 525

Thr Ser Thr Leu Thr Ser Ser Asn Arg Asn Asp Val Thr Gly Gly Arg
    530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
            565                 570                 575

Thr Ser Ala Lys Thr Gly Ser Phe Gly Val Thr Ala Val Thr Val Gly
        580                 585                 590

Asp Ser Asn Ser Asn Val Asn Arg Ser Leu Ser Gly Asp Gln Asp Thr
    595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640
```

```
Pro Ile Arg Thr Pro Gln Ile Pro Glu Trp Leu Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Leu Val Ile Asn Ser Gly Asn
        675                 680                 685

Gly Ala Val Glu Asp Arg Lys Pro Ser Gly Leu Asn Gly Glu Ala Ser
690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740

<210> SEQ ID NO 7
<211> LENGTH: 803
<212> TYPE: PRT
<213> ORGANISM: Homo sapiens

<400> SEQUENCE: 7

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
            260                 265                 270
```

```
Gln Phe Ile Asn Phe Pro Ile Tyr Val Trp Ser Ser Lys Thr Glu Thr
        275                 280                 285

Val Glu Glu Pro Met Glu Glu Glu Ala Ala Lys Glu Glu Lys Glu
290                 295                 300

Glu Ser Asp Asp Glu Ala Ala Val Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
                340                 345                 350

Asp Glu Tyr Lys Ala Phe Tyr Lys Ser Phe Ser Lys Glu Ser Asp Asp
                355                 360                 365

Pro Met Ala Tyr Ile His Phe Thr Ala Glu Gly Glu Val Thr Phe Lys
        370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
        420                 425                 430

Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
        450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
        500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
        530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
        580                 585                 590

Lys Glu Gly Val Lys Phe Asp Glu Ser Glu Lys Thr Lys Glu Ser Arg
        595                 600                 605

Glu Ala Val Glu Lys Glu Phe Glu Pro Leu Leu Asn Trp Met Lys Asp
        610                 615                 620

Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
                660                 665                 670

Ile Ser Thr Asn Tyr Tyr Ala Ser Gln Lys Lys Thr Phe Glu Ile Asn
                675                 680                 685
```

```
Pro Arg His Pro Leu Ile Arg Asp Met Leu Arg Arg Ile Lys Glu Asp
    690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
            740                 745                 750

Ala Lys Val Glu Glu Pro Glu Glu Pro Glu Glu Thr Ala Glu
        755                 760                 765

Asp Thr Thr Glu Asp Thr Glu Gln Asp Glu Asp Glu Glu Met Asp Val
        770                 775                 780

Gly Thr Asp Glu Glu Glu Glu Thr Ala Lys Glu Ser Thr Ala Glu Lys
785                 790                 795                 800

Asp Glu Leu

<210> SEQ ID NO 8
<211> LENGTH: 4289
<212> TYPE: PRT
<213> ORGANISM: Homo sapiens

<400> SEQUENCE: 8

Met Met Pro Ala Gln Tyr Ala Leu Thr Ser Ser Leu Val Leu Leu Val
1               5                   10                  15

Leu Leu Ser Thr Ala Arg Ala Gly Pro Phe Ser Ser Arg Ser Asn Val
                20                  25                  30

Thr Leu Pro Ala Pro Arg Pro Pro Gln Pro Gly His Thr Val
            35                  40                  45

Gly Ala Gly Val Gly Ser Pro Ser Ser Gln Leu Tyr Glu His Thr Val
50                  55                  60

Glu Gly Gly Glu Lys Gln Val Val Phe Thr His Arg Ile Asn Leu Pro
65                  70                  75                  80

Pro Ser Thr Gly Cys Gly Cys Pro Pro Gly Thr Glu Pro Pro Val Leu
                85                  90                  95

Ala Ser Glu Val Gln Ala Leu Arg Val Arg Leu Glu Ile Leu Glu Glu
            100                 105                 110

Leu Val Lys Gly Leu Lys Glu Gln Cys Thr Gly Gly Cys Cys Pro Ala
                115                 120                 125

Ser Ala Gln Ala Gly Thr Gly Gln Thr Asp Val Arg Thr Leu Cys Ser
        130                 135                 140

Leu His Gly Val Phe Asp Leu Ser Arg Cys Thr Cys Ser Cys Glu Pro
145                 150                 155                 160

Gly Trp Gly Gly Pro Thr Cys Ser Asp Pro Thr Asp Ala Glu Ile Pro
                165                 170                 175

Pro Ser Ser Pro Pro Ser Ala Ser Gly Ser Cys Pro Asp Asp Cys Asn
            180                 185                 190

Asp Gln Gly Arg Cys Val Arg Gly Arg Cys Val Cys Phe Pro Gly Tyr
        195                 200                 205

Thr Gly Pro Ser Cys Gly Trp Pro Ser Cys Pro Gly Asp Cys Gln Gly
    210                 215                 220

Arg Gly Arg Cys Val Gln Gly Val Cys Val Cys Arg Ala Gly Phe Ser
225                 230                 235                 240

Gly Pro Asp Cys Ser Gln Arg Ser Cys Pro Arg Gly Cys Ser Gln Arg
                245                 250                 255
```

-continued

Gly Arg Cys Glu Gly Arg Cys Val Cys Asp Pro Gly Tyr Thr Gly
               260                 265                 270

Asp Asp Cys Gly Met Arg Ser Cys Pro Arg Gly Cys Ser Gln Arg Gly
            275                 280                 285

Arg Cys Glu Asn Gly Arg Cys Val Cys Asn Pro Gly Tyr Thr Gly Glu
        290                 295                 300

Asp Cys Gly Val Arg Ser Cys Pro Arg Gly Cys Ser Gln Arg Gly Arg
305                 310                 315                 320

Cys Lys Asp Gly Arg Cys Val Cys Asp Pro Gly Tyr Thr Gly Glu Asp
                325                 330                 335

Cys Gly Thr Arg Ser Cys Pro Trp Asp Cys Gly Glu Gly Arg Cys
            340                 345                 350

Val Asp Gly Arg Cys Val Cys Trp Pro Gly Tyr Thr Gly Glu Asp Cys
        355                 360                 365

Ser Thr Arg Thr Cys Pro Arg Asp Cys Arg Gly Arg Gly Arg Cys Glu
    370                 375                 380

Asp Gly Glu Cys Ile Cys Asp Thr Gly Tyr Ser Gly Asp Asp Cys Gly
385                 390                 395                 400

Val Arg Ser Cys Pro Gly Asp Cys Asn Gln Arg Gly Arg Cys Glu Asp
                405                 410                 415

Gly Arg Cys Val Cys Trp Pro Gly Tyr Thr Gly Thr Asp Cys Gly Ser
            420                 425                 430

Arg Ala Cys Pro Arg Asp Cys Arg Gly Arg Gly Arg Cys Glu Asn Gly
        435                 440                 445

Val Cys Val Cys Asn Ala Gly Tyr Ser Gly Glu Asp Cys Gly Val Arg
    450                 455                 460

Ser Cys Pro Gly Asp Cys Arg Gly Arg Gly Arg Cys Glu Ser Gly Arg
465                 470                 475                 480

Cys Met Cys Trp Pro Gly Tyr Thr Gly Arg Asp Cys Gly Thr Arg Ala
                485                 490                 495

Cys Pro Gly Asp Cys Arg Gly Arg Gly Arg Cys Val Asp Gly Arg Cys
            500                 505                 510

Val Cys Asn Pro Gly Phe Thr Gly Glu Asp Cys Gly Ser Arg Arg Cys
        515                 520                 525

Pro Gly Asp Cys Arg Gly His Gly Leu Cys Glu Asp Gly Val Cys Val
    530                 535                 540

Cys Asp Ala Gly Tyr Ser Gly Glu Asp Cys Ser Thr Arg Ser Cys Pro
545                 550                 555                 560

Gly Gly Cys Arg Gly Arg Gly Gln Cys Leu Asp Gly Arg Cys Val Cys
                565                 570                 575

Glu Asp Gly Tyr Ser Gly Glu Asp Cys Gly Val Arg Gln Cys Pro Asn
            580                 585                 590

Asp Cys Ser Gln His Gly Val Cys Gln Asp Gly Val Cys Ile Cys Trp
        595                 600                 605

Glu Gly Tyr Val Ser Glu Asp Cys Ser Ile Arg Thr Cys Pro Ser Asn
    610                 615                 620

Cys His Gly Arg Gly Arg Cys Glu Glu Gly Arg Cys Leu Cys Asp Pro
625                 630                 635                 640

Gly Tyr Thr Gly Pro Thr Cys Ala Thr Arg Met Cys Pro Ala Asp Cys
                645                 650                 655

Arg Gly Arg Gly Arg Cys Val Gln Gly Val Cys Leu Cys His Val Gly
            660                 665                 670

Tyr Gly Gly Glu Asp Cys Gly Gln Glu Glu Pro Pro Ala Ser Ala Cys

-continued

```
            675                 680                 685
Pro Gly Gly Cys Gly Pro Arg Glu Leu Cys Arg Ala Gly Gln Cys Val
        690                 695                 700
Cys Val Glu Gly Phe Arg Gly Pro Asp Cys Ala Ile Gln Thr Cys Pro
705                 710                 715                 720
Gly Asp Cys Arg Gly Arg Gly Glu Cys His Asp Gly Ser Cys Val Cys
                725                 730                 735
Lys Asp Gly Tyr Ala Gly Glu Asp Cys Gly Glu Ala Arg Val Pro Ser
                740                 745                 750
Ser Ala Ser Ala Tyr Asp Gln Arg Gly Leu Ala Pro Gly Gln Glu Tyr
        755                 760                 765
Gln Val Thr Val Arg Ala Leu Arg Gly Thr Ser Trp Gly Leu Pro Ala
770                 775                 780
Ser Lys Thr Ile Thr Thr Met Ile Asp Gly Pro Gln Asp Leu Arg Val
785                 790                 795                 800
Val Ala Val Thr Pro Thr Thr Leu Glu Leu Gly Trp Leu Arg Pro Gln
                805                 810                 815
Ala Glu Val Asp Arg Phe Val Val Ser Tyr Val Ser Ala Gly Asn Gln
                820                 825                 830
Arg Val Arg Leu Glu Val Pro Pro Glu Ala Asp Gly Thr Leu Leu Thr
        835                 840                 845
Asp Leu Met Pro Gly Val Glu Tyr Val Val Thr Val Thr Ala Glu Arg
850                 855                 860
Gly Arg Ala Val Ser Tyr Pro Ala Ser Val Arg Ala Asn Thr Glu Glu
865                 870                 875                 880
Arg Glu Glu Glu Ser Pro Arg Pro Ser Leu Ser Gln Pro Pro Arg
                885                 890                 895
Arg Pro Trp Gly Asn Leu Thr Ala Glu Leu Ser Arg Phe Arg Gly Thr
                900                 905                 910
Val Gln Asp Leu Glu Arg His Leu Arg Ala His Gly Tyr Pro Leu Arg
        915                 920                 925
Ala Asn Gln Thr Tyr Thr Ser Val Ala Arg His Ile His Glu Tyr Leu
        930                 935                 940
Gln Arg Gln Val Leu Gly Ser Ser Ala Asp Gly Ala Leu Leu Val Ser
945                 950                 955                 960
Leu Asp Gly Leu Arg Gly Gln Phe Glu Arg Val Val Leu Arg Trp Arg
                965                 970                 975
Pro Gln Pro Pro Ala Glu Gly Pro Gly Gly Glu Leu Thr Val Pro Gly
                980                 985                 990
Thr Thr Arg Thr Val Ser Leu Pro Asp Leu Arg Pro Gly Thr Thr Tyr
        995                 1000                1005
His Val Glu Val His Gly Val Arg Ala Gly Gln Thr Ser Lys Ser
        1010                1015                1020
Tyr Ala Phe Ile Thr Thr Thr Gly Pro Ser Thr Thr Gln Gly Ala
        1025                1030                1035
Gln Ala Pro Leu Leu Gln Gln Arg Pro Gln Glu Leu Gly Glu Leu
        1040                1045                1050
Arg Val Leu Gly Arg Asp Glu Thr Gly Arg Leu Arg Val Val Trp
        1055                1060                1065
Thr Ala Gln Pro Asp Thr Phe Ala Tyr Phe Gln Leu Arg Met Arg
        1070                1075                1080
Val Pro Glu Gly Pro Gly Ala His Glu Glu Val Leu Pro Gly Asp
        1085                1090                1095
```

-continued

```
Val Arg Gln Ala Leu Val Pro Pro Pro Pro Gly Thr Pro Tyr
    1100              1105              1110

Glu Leu Ser Leu His Gly Val Pro Pro Gly Gly Lys Pro Ser Asp
    1115              1120              1125

Pro Ile Ile Tyr Gln Gly Ile Met Asp Lys Asp Glu Glu Lys Pro
    1130              1135              1140

Gly Lys Ser Ser Gly Pro Pro Arg Leu Gly Glu Leu Thr Val Thr
    1145              1150              1155

Asp Arg Thr Ser Asp Ser Leu Leu Leu Arg Trp Thr Val Pro Glu
    1160              1165              1170

Gly Glu Phe Asp Ser Phe Val Ile Gln Tyr Lys Asp Arg Asp Gly
    1175              1180              1185

Gln Pro Gln Val Val Pro Val Glu Gly Pro Gln Arg Ser Ala Val
    1190              1195              1200

Ile Thr Ser Leu Asp Pro Gly Arg Lys Tyr Lys Phe Val Leu Tyr
    1205              1210              1215

Gly Phe Val Gly Lys Lys Arg His Gly Pro Leu Val Ala Glu Ala
    1220              1225              1230

Lys Ile Leu Pro Gln Ser Asp Pro Ser Pro Gly Thr Pro Pro His
    1235              1240              1245

Leu Gly Asn Leu Trp Val Thr Asp Pro Thr Pro Asp Ser Leu His
    1250              1255              1260

Leu Ser Trp Thr Val Pro Glu Gly Gln Phe Asp Thr Phe Met Val
    1265              1270              1275

Gln Tyr Arg Asp Arg Asp Gly Arg Pro Gln Val Val Pro Val Glu
    1280              1285              1290

Gly Pro Glu Arg Ser Phe Val Val Ser Ser Leu Asp Pro Asp His
    1295              1300              1305

Lys Tyr Arg Phe Thr Leu Phe Gly Ile Ala Asn Lys Lys Arg Tyr
    1310              1315              1320

Gly Pro Leu Thr Ala Asp Gly Thr Thr Ala Pro Glu Arg Lys Glu
    1325              1330              1335

Glu Pro Pro Arg Pro Glu Phe Leu Glu Gln Pro Leu Leu Gly Glu
    1340              1345              1350

Leu Thr Val Thr Gly Val Thr Pro Asp Ser Leu Arg Leu Ser Trp
    1355              1360              1365

Thr Val Ala Gln Gly Pro Phe Asp Ser Phe Met Val Gln Tyr Lys
    1370              1375              1380

Asp Ala Gln Gly Gln Pro Gln Ala Val Pro Val Ala Gly Asp Glu
    1385              1390              1395

Asn Glu Val Thr Val Pro Gly Leu Asp Pro Asp Arg Lys Tyr Lys
    1400              1405              1410

Met Asn Leu Tyr Gly Leu Arg Gly Arg Gln Arg Val Gly Pro Glu
    1415              1420              1425

Ser Val Val Ala Lys Thr Ala Pro Gln Glu Asp Val Asp Glu Thr
    1430              1435              1440

Pro Ser Pro Thr Glu Leu Gly Thr Glu Ala Pro Glu Ser Pro Glu
    1445              1450              1455

Glu Pro Leu Leu Gly Glu Leu Thr Val Thr Gly Ser Ser Pro Asp
    1460              1465              1470

Ser Leu Ser Leu Phe Trp Thr Val Pro Gln Gly Ser Phe Asp Ser
    1475              1480              1485
```

```
Phe Thr Val Gln Tyr Lys Asp Arg Asp Gly Arg Pro Arg Ala Val
1490                1495                1500

Arg Val Gly Gly Lys Glu Ser Glu Val Thr Val Gly Gly Leu Glu
1505                1510                1515

Pro Gly His Lys Tyr Lys Met His Leu Tyr Gly Leu His Glu Gly
1520                1525                1530

Gln Arg Val Gly Pro Val Ser Ala Val Gly Val Thr Ala Pro Gln
1535                1540                1545

Gln Glu Glu Thr Pro Pro Ala Thr Glu Ser Pro Leu Glu Pro Arg
1550                1555                1560

Leu Gly Glu Leu Thr Val Thr Asp Val Thr Pro Asn Ser Val Gly
1565                1570                1575

Leu Ser Trp Thr Val Pro Glu Gly Gln Phe Asp Ser Phe Ile Val
1580                1585                1590

Gln Tyr Lys Asp Lys Asp Gly Gln Pro Gln Val Val Pro Val Ala
1595                1600                1605

Ala Asp Gln Arg Glu Val Thr Val Tyr Asn Leu Glu Pro Glu Arg
1610                1615                1620

Lys Tyr Lys Met Asn Met Tyr Gly Leu His Asp Gly Gln Arg Met
1625                1630                1635

Gly Pro Leu Ser Val Val Ile Val Thr Ala Pro Ala Thr Glu Ala
1640                1645                1650

Ser Lys Pro Pro Leu Glu Pro Arg Leu Gly Glu Leu Thr Val Thr
1655                1660                1665

Asp Ile Thr Pro Asp Ser Val Gly Leu Ser Trp Thr Val Pro Glu
1670                1675                1680

Gly Glu Phe Asp Ser Phe Val Val Gln Tyr Lys Asp Arg Asp Gly
1685                1690                1695

Gln Pro Gln Val Val Pro Val Ala Ala Asp Gln Arg Glu Val Thr
1700                1705                1710

Ile Pro Asp Leu Glu Pro Ser Arg Lys Tyr Lys Phe Leu Leu Phe
1715                1720                1725

Gly Ile Gln Asp Gly Lys Arg Arg Ser Pro Val Ser Val Glu Ala
1730                1735                1740

Lys Thr Val Ala Arg Gly Asp Ala Ser Pro Gly Ala Pro Pro Arg
1745                1750                1755

Leu Gly Glu Leu Trp Val Thr Asp Pro Thr Pro Asp Ser Leu Arg
1760                1765                1770

Leu Ser Trp Thr Val Pro Glu Gly Gln Phe Asp Ser Phe Val Val
1775                1780                1785

Gln Phe Lys Asp Lys Asp Gly Pro Gln Val Val Pro Val Glu Gly
1790                1795                1800

His Glu Arg Ser Val Thr Val Thr Pro Leu Asp Ala Gly Arg Lys
1805                1810                1815

Tyr Arg Phe Leu Leu Tyr Gly Leu Leu Gly Lys Lys Arg His Gly
1820                1825                1830

Pro Leu Thr Ala Asp Gly Thr Thr Glu Ala Arg Ser Ala Met Asp
1835                1840                1845

Asp Thr Gly Thr Lys Arg Pro Pro Lys Pro Arg Leu Gly Glu Glu
1850                1855                1860

Leu Gln Val Thr Thr Val Thr Gln Asn Ser Val Gly Leu Ser Trp
1865                1870                1875

Thr Val Pro Glu Gly Gln Phe Asp Ser Phe Val Val Gln Tyr Lys
```

-continued

```
            1880                1885                1890
Asp Arg Asp Gly Gln Pro Gln Val Val Pro Val Glu Gly Ser Leu
    1895                1900                1905
Arg Glu Val Ser Val Pro Gly Leu Asp Pro Ala His Arg Tyr Lys
    1910                1915                1920
Leu Leu Leu Tyr Gly Leu His His Gly Lys Arg Val Gly Pro Ile
    1925                1930                1935
Ser Ala Val Ala Ile Thr Ala Gly Arg Glu Thr Glu Thr Glu
    1940                1945                1950
Thr Thr Ala Pro Thr Pro Pro Ala Pro Glu Pro His Leu Gly Glu
    1955                1960                1965
Leu Thr Val Glu Glu Ala Thr Ser His Thr Leu His Leu Ser Trp
    1970                1975                1980
Met Val Thr Glu Gly Glu Phe Asp Ser Phe Glu Ile Gln Tyr Thr
    1985                1990                1995
Asp Arg Asp Gly Gln Leu Gln Met Val Arg Ile Gly Gly Asp Arg
    2000                2005                2010
Asn Asp Ile Thr Leu Ser Gly Leu Glu Ser Asp His Arg Tyr Leu
    2015                2020                2025
Val Thr Leu Tyr Gly Phe Ser Asp Gly Lys His Val Gly Pro Val
    2030                2035                2040
His Val Glu Ala Leu Thr Val Pro Glu Glu Lys Pro Ser Glu
    2045                2050                2055
Pro Pro Thr Ala Thr Pro Glu Pro Pro Ile Lys Pro Arg Leu Gly
    2060                2065                2070
Glu Leu Thr Val Thr Asp Ala Thr Pro Asp Ser Leu Ser Leu Ser
    2075                2080                2085
Trp Thr Val Pro Glu Gly Gln Phe Asp His Phe Leu Val Gln Tyr
    2090                2095                2100
Arg Asn Gly Asp Gly Gln Pro Lys Ala Val Arg Val Pro Gly His
    2105                2110                2115
Glu Glu Gly Val Thr Ile Ser Gly Leu Glu Pro Asp His Lys Tyr
    2120                2125                2130
Lys Met Asn Leu Tyr Gly Phe His Gly Gly Gln Arg Met Gly Pro
    2135                2140                2145
Val Ser Val Val Gly Val Thr Glu Pro Ser Met Glu Ala Pro Glu
    2150                2155                2160
Pro Ala Glu Glu Pro Leu Leu Gly Glu Leu Thr Val Thr Gly Ser
    2165                2170                2175
Ser Pro Asp Ser Leu Ser Leu Ser Trp Thr Val Pro Gln Gly Arg
    2180                2185                2190
Phe Asp Ser Phe Thr Val Gln Tyr Lys Asp Arg Asp Gly Arg Pro
    2195                2200                2205
Gln Val Val Arg Val Gly Gly Glu Glu Ser Glu Val Thr Val Gly
    2210                2215                2220
Gly Leu Glu Pro Gly Arg Lys Tyr Lys Met His Leu Tyr Gly Leu
    2225                2230                2235
His Glu Gly Arg Arg Val Gly Pro Val Ser Ala Val Gly Val Thr
    2240                2245                2250
Ala Pro Glu Glu Glu Ser Pro Asp Ala Pro Leu Ala Lys Leu Arg
    2255                2260                2265
Leu Gly Gln Met Thr Val Arg Asp Ile Thr Ser Asp Ser Leu Ser
    2270                2275                2280
```

Leu Ser Trp Thr Val Pro Glu Gly Gln Phe Asp His Phe Leu Val
    2285             2290             2295

Gln Phe Lys Asn Gly Asp Gly Gln Pro Lys Ala Val Arg Val Pro
2300             2305             2310

Gly His Glu Asp Gly Val Thr Ile Ser Gly Leu Glu Pro Asp His
    2315             2320             2325

Lys Tyr Lys Met Asn Leu Tyr Gly Phe His Gly Gln Arg Val
    2330             2335             2340

Gly Pro Val Ser Ala Val Gly Leu Thr Ala Ser Thr Glu Pro Pro
    2345             2350             2355

Thr Pro Glu Pro Pro Ile Lys Pro Arg Leu Glu Glu Leu Thr Val
    2360             2365             2370

Thr Asp Ala Thr Pro Asp Ser Leu Ser Leu Ser Trp Thr Val Pro
    2375             2380             2385

Glu Gly Gln Phe Asp His Phe Leu Val Gln Tyr Lys Asn Gly Asp
    2390             2395             2400

Gly Gln Pro Lys Ala Thr Arg Val Pro Gly His Glu Asp Arg Val
    2405             2410             2415

Thr Ile Ser Gly Leu Glu Pro Asp Asn Lys Tyr Lys Met Asn Leu
    2420             2425             2430

Tyr Gly Phe His Gly Gly Gln Arg Val Gly Pro Val Ser Ala Ile
    2435             2440             2445

Gly Val Thr Glu Glu Glu Thr Pro Ser Pro Thr Glu Pro Ser Met
    2450             2455             2460

Glu Ala Pro Glu Pro Pro Glu Pro Leu Leu Gly Glu Leu Thr
    2465             2470             2475

Val Thr Gly Ser Ser Pro Asp Ser Leu Ser Leu Ser Trp Thr Val
    2480             2485             2490

Pro Gln Gly Arg Phe Asp Ser Phe Thr Val Gln Tyr Lys Asp Arg
    2495             2500             2505

Asp Gly Arg Pro Gln Val Val Arg Val Gly Gly Glu Glu Ser Glu
    2510             2515             2520

Val Thr Val Gly Gly Leu Glu Pro Gly Arg Lys Tyr Lys Met His
    2525             2530             2535

Leu Tyr Gly Leu His Glu Gly Arg Arg Val Gly Pro Val Ser Thr
    2540             2545             2550

Val Gly Val Thr Ala Pro Gln Glu Asp Val Asp Glu Thr Pro Ser
    2555             2560             2565

Pro Thr Glu Pro Gly Thr Glu Ala Pro Gly Pro Pro Glu Glu Pro
    2570             2575             2580

Leu Leu Gly Glu Leu Thr Val Thr Gly Ser Ser Pro Asp Ser Leu
    2585             2590             2595

Ser Leu Ser Trp Thr Val Pro Gln Gly Arg Phe Asp Ser Phe Thr
    2600             2605             2610

Val Gln Tyr Lys Asp Arg Asp Gly Arg Pro Gln Ala Val Arg Val
    2615             2620             2625

Gly Gly Gln Glu Ser Lys Val Thr Val Arg Gly Leu Glu Pro Gly
    2630             2635             2640

Arg Lys Tyr Lys Met His Leu Tyr Gly Leu His Glu Gly Arg Arg
    2645             2650             2655

Leu Gly Pro Val Ser Ala Val Gly Val Thr Glu Asp Glu Ala Glu
    2660             2665             2670

```
Thr Thr Gln Ala Val Pro Thr Met Thr Pro Glu Pro Pro Ile Lys
2675                2680                2685

Pro Arg Leu Gly Glu Leu Thr Met Thr Asp Ala Thr Pro Asp Ser
2690                2695                2700

Leu Ser Leu Ser Trp Thr Val Pro Glu Gly Gln Phe Asp His Phe
2705                2710                2715

Leu Val Gln Tyr Arg Asn Gly Asp Gly Gln Pro Lys Ala Val Arg
2720                2725                2730

Val Pro Gly His Glu Asp Gly Val Thr Ile Ser Gly Leu Glu Pro
2735                2740                2745

Asp His Lys Tyr Lys Met Asn Leu Tyr Gly Phe His Gly Gly Gln
2750                2755                2760

Arg Val Gly Pro Ile Ser Val Ile Gly Val Thr Glu Glu Glu Thr
2765                2770                2775

Pro Ser Pro Thr Glu Leu Ser Thr Glu Ala Pro Glu Pro Pro Glu
2780                2785                2790

Glu Pro Leu Leu Gly Glu Leu Thr Val Thr Gly Ser Ser Pro Asp
2795                2800                2805

Ser Leu Ser Leu Ser Trp Thr Ile Pro Gln Gly His Phe Asp Ser
2810                2815                2820

Phe Thr Val Gln Tyr Lys Asp Arg Asp Gly Arg Pro Gln Val Met
2825                2830                2835

Arg Val Arg Gly Glu Glu Ser Glu Val Thr Val Gly Gly Leu Glu
2840                2845                2850

Pro Gly Arg Lys Tyr Lys Met His Leu Tyr Gly Leu His Glu Gly
2855                2860                2865

Arg Arg Val Gly Pro Val Ser Thr Val Gly Val Thr Val Pro Thr
2870                2875                2880

Thr Thr Pro Glu Pro Pro Asn Lys Pro Arg Leu Gly Glu Leu Thr
2885                2890                2895

Val Thr Asp Ala Thr Pro Asp Ser Leu Ser Leu Ser Trp Met Val
2900                2905                2910

Pro Glu Gly Gln Phe Asp His Phe Leu Val Gln Tyr Arg Asn Gly
2915                2920                2925

Asp Gly Gln Pro Lys Val Val Arg Val Pro Gly His Glu Asp Gly
2930                2935                2940

Val Thr Ile Ser Gly Leu Glu Pro Asp His Lys Tyr Lys Met Asn
2945                2950                2955

Leu Tyr Gly Phe His Gly Gly Gln Arg Val Gly Pro Ile Ser Val
2960                2965                2970

Ile Gly Val Thr Glu Glu Glu Thr Pro Ala Pro Thr Glu Pro Ser
2975                2980                2985

Thr Glu Ala Pro Glu Pro Pro Glu Glu Pro Leu Leu Gly Glu Leu
2990                2995                3000

Thr Val Thr Gly Ser Ser Pro Asp Ser Leu Ser Leu Ser Trp Thr
3005                3010                3015

Ile Pro Gln Gly Arg Phe Asp Ser Phe Thr Val Gln Tyr Lys Asp
3020                3025                3030

Arg Asp Gly Arg Pro Gln Val Val Arg Val Arg Gly Glu Glu Ser
3035                3040                3045

Glu Val Thr Val Gly Gly Leu Glu Pro Gly Cys Lys Tyr Lys Met
3050                3055                3060

His Leu Tyr Gly Leu His Glu Gly Gln Arg Val Gly Pro Val Ser
```

-continued

```
              3065                3070                3075
Ala Val Gly Val Thr Ala Pro Lys Asp Glu Ala Glu Thr Thr Gln
        3080                3085                3090
Ala Val Pro Thr Met Thr Pro Glu Pro Pro Ile Lys Pro Arg Leu
        3095                3100                3105
Gly Glu Leu Thr Val Thr Asp Ala Thr Pro Asp Ser Leu Ser Leu
        3110                3115                3120
Ser Trp Met Val Pro Glu Gly Gln Phe Asp His Phe Leu Val Gln
        3125                3130                3135
Tyr Arg Asn Gly Asp Gly Gln Pro Lys Ala Val Arg Val Pro Gly
        3140                3145                3150
His Glu Asp Gly Val Thr Ile Ser Gly Leu Glu Pro Asp His Lys
        3155                3160                3165
Tyr Lys Met Asn Leu Tyr Gly Phe His Gly Gly Gln Arg Val Gly
        3170                3175                3180
Pro Val Ser Ala Ile Gly Val Thr Glu Glu Thr Pro Ser Pro
        3185                3190                3195
Thr Glu Pro Ser Thr Glu Ala Pro Glu Ala Pro Glu Glu Pro Leu
        3200                3205                3210
Leu Gly Glu Leu Thr Val Thr Gly Ser Ser Pro Asp Ser Leu Ser
        3215                3220                3225
Leu Ser Trp Thr Val Pro Gln Gly Arg Phe Asp Ser Phe Thr Val
        3230                3235                3240
Gln Tyr Lys Asp Arg Asp Gly Gln Pro Gln Val Val Arg Val Arg
        3245                3250                3255
Gly Glu Glu Ser Glu Val Thr Val Gly Gly Leu Glu Pro Gly Arg
        3260                3265                3270
Lys Tyr Lys Met His Leu Tyr Gly Leu His Glu Gly Gln Arg Val
        3275                3280                3285
Gly Pro Val Ser Thr Val Gly Ile Thr Ala Pro Leu Pro Thr Pro
        3290                3295                3300
Leu Pro Val Glu Pro Arg Leu Gly Glu Leu Ala Val Ala Ala Val
        3305                3310                3315
Thr Ser Asp Ser Val Gly Leu Ser Trp Thr Val Ala Gln Gly Pro
        3320                3325                3330
Phe Asp Ser Phe Leu Val Gln Tyr Arg Asp Ala Gln Gly Gln Pro
        3335                3340                3345
Gln Ala Val Pro Val Ser Gly Asp Leu Arg Ala Val Ala Val Ser
        3350                3355                3360
Gly Leu Asp Pro Ala Arg Lys Tyr Lys Phe Leu Leu Phe Gly Leu
        3365                3370                3375
Gln Asn Gly Lys Arg His Gly Pro Val Pro Val Glu Ala Arg Thr
        3380                3385                3390
Ala Pro Asp Thr Lys Pro Ser Pro Arg Leu Gly Glu Leu Thr Val
        3395                3400                3405
Thr Asp Ala Thr Pro Asp Ser Val Gly Leu Ser Trp Thr Val Pro
        3410                3415                3420
Glu Gly Glu Phe Asp Ser Phe Val Val Gln Tyr Lys Asp Lys Asp
        3425                3430                3435
Gly Arg Leu Gln Val Val Pro Val Ala Ala Asn Gln Arg Glu Val
        3440                3445                3450
Thr Val Gln Gly Leu Glu Pro Ser Arg Lys Tyr Arg Phe Leu Leu
        3455                3460                3465
```

-continued

```
Tyr Gly Leu Ser Gly Arg Lys Arg Leu Gly Pro Ile Ser Ala Asp
        3470            3475                3480

Ser Thr Thr Ala Pro Leu Glu Lys Glu Leu Pro His Leu Gly
    3485            3490                3495

Glu Leu Thr Val Ala Glu Glu Thr Ser Ser Leu Arg Leu Ser
    3500            3505                3510

Trp Thr Val Ala Gln Gly Pro Phe Asp Ser Phe Val Gln Tyr
    3515            3520                3525

Arg Asp Thr Asp Gly Gln Pro Arg Ala Val Pro Val Ala Ala Asp
        3530            3535                3540

Gln Arg Thr Val Thr Val Glu Asp Leu Glu Pro Gly Lys Lys Tyr
        3545            3550                3555

Lys Phe Leu Leu Tyr Gly Leu Leu Gly Gly Lys Arg Leu Gly Pro
        3560            3565                3570

Val Ser Ala Leu Gly Met Thr Ala Pro Glu Glu Asp Thr Pro Ala
        3575            3580                3585

Pro Glu Leu Ala Pro Glu Ala Pro Glu Pro Pro Glu Glu Pro Arg
        3590            3595                3600

Leu Gly Val Leu Thr Val Thr Asp Thr Thr Pro Asp Ser Met Arg
        3605            3610                3615

Leu Ser Trp Ser Val Ala Gln Gly Pro Phe Asp Ser Phe Val Val
        3620            3625                3630

Gln Tyr Glu Asp Thr Asn Gly Gln Pro Gln Ala Leu Leu Val Asp
        3635            3640                3645

Gly Asp Gln Ser Lys Ile Leu Ile Ser Gly Leu Glu Pro Ser Thr
        3650            3655                3660

Pro Tyr Arg Phe Leu Leu Tyr Gly Leu His Glu Gly Lys Arg Leu
        3665            3670                3675

Gly Pro Leu Ser Ala Glu Gly Thr Thr Gly Leu Ala Pro Ala Gly
        3680            3685                3690

Gln Thr Ser Glu Glu Ser Arg Pro Arg Leu Ser Gln Leu Ser Val
        3695            3700                3705

Thr Asp Val Thr Thr Ser Ser Leu Arg Leu Asn Trp Glu Ala Pro
        3710            3715                3720

Pro Gly Ala Phe Asp Ser Phe Leu Leu Arg Phe Gly Val Pro Ser
        3725            3730                3735

Pro Ser Thr Leu Glu Pro His Pro Arg Pro Leu Leu Gln Arg Glu
        3740            3745                3750

Leu Met Val Pro Gly Thr Arg His Ser Ala Val Leu Arg Asp Leu
        3755            3760                3765

Arg Ser Gly Thr Leu Tyr Ser Leu Thr Leu Tyr Gly Leu Arg Gly
        3770            3775                3780

Pro His Lys Ala Asp Ser Ile Gln Gly Thr Ala Arg Thr Leu Ser
        3785            3790                3795

Pro Val Leu Glu Ser Pro Arg Asp Leu Gln Phe Ser Glu Ile Arg
        3800            3805                3810

Glu Thr Ser Ala Lys Val Asn Trp Met Pro Pro Ser Arg Ala
        3815            3820                3825

Asp Ser Phe Lys Val Ser Tyr Gln Leu Ala Asp Gly Gly Glu Pro
        3830            3835                3840

Gln Ser Val Gln Val Asp Gly Gln Ala Arg Thr Gln Lys Leu Gln
        3845            3850                3855
```

Gly Leu Ile Pro Gly Ala Arg Tyr Glu Val Thr Val Val Ser Val
3860          3865               3870

Arg Gly Phe Glu Glu Ser Glu Pro Leu Thr Gly Phe Leu Thr Thr
3875          3880               3885

Val Pro Asp Gly Pro Thr Gln Leu Arg Ala Leu Asn Leu Thr Glu
3890          3895               3900

Gly Phe Ala Val Leu His Trp Lys Pro Pro Gln Asn Pro Val Asp
3905          3910               3915

Thr Tyr Asp Val Gln Val Thr Ala Pro Gly Ala Pro Pro Leu Gln
3920          3925               3930

Ala Glu Thr Pro Gly Ser Ala Val Asp Tyr Pro Leu His Asp Leu
3935          3940               3945

Val Leu His Thr Asn Tyr Thr Ala Thr Val Arg Gly Leu Arg Gly
3950          3955               3960

Pro Asn Leu Thr Ser Pro Ala Ser Ile Thr Phe Thr Thr Gly Leu
3965          3970               3975

Glu Ala Pro Arg Asp Leu Glu Ala Lys Glu Val Thr Pro Arg Thr
3980          3985               3990

Ala Leu Leu Thr Trp Thr Glu Pro Pro Val Arg Pro Ala Gly Tyr
3995          4000               4005

Leu Leu Ser Phe His Thr Pro Gly Gly Gln Asn Gln Glu Ile Leu
4010          4015               4020

Leu Pro Gly Gly Ile Thr Ser His Gln Leu Leu Gly Leu Phe Pro
4025          4030               4035

Ser Thr Ser Tyr Asn Ala Arg Leu Gln Ala Met Trp Gly Gln Ser
4040          4045               4050

Leu Leu Pro Pro Val Ser Ser Phe Thr Thr Gly Gly Leu Arg
4055          4060               4065

Ile Pro Phe Pro Arg Asp Cys Gly Glu Glu Met Gln Asn Gly Ala
4070          4075               4080

Gly Ala Ser Arg Thr Ser Thr Ile Phe Leu Asn Gly Asn Arg Glu
4085          4090               4095

Arg Pro Leu Asn Val Phe Cys Asp Met Glu Thr Asp Gly Gly Gly
4100          4105               4110

Trp Leu Val Phe Gln Arg Arg Met Asp Gly Gln Thr Asp Phe Trp
4115          4120               4125

Arg Asp Trp Glu Asp Tyr Ala His Gly Phe Gly Asn Ile Ser Gly
4130          4135               4140

Glu Phe Trp Leu Gly Asn Glu Ala Leu His Ser Leu Thr Gln Ala
4145          4150               4155

Gly Asp Tyr Ser Met Arg Val Asp Leu Arg Ala Gly Asp Glu Ala
4160          4165               4170

Val Phe Ala Gln Tyr Asp Ser Phe His Val Asp Ser Ala Ala Glu
4175          4180               4185

Tyr Tyr Arg Leu His Leu Glu Gly Tyr His Gly Thr Ala Gly Asp
4190          4195               4200

Ser Met Ser Tyr His Ser Gly Ser Val Phe Ser Ala Arg Asp Arg
4205          4210               4215

Asp Pro Asn Ser Leu Leu Ile Ser Cys Ala Val Ser Tyr Arg Gly
4220          4225               4230

Ala Trp Trp Tyr Arg Asn Cys His Tyr Ala Asn Leu Asn Gly Leu
4235          4240               4245

Tyr Gly Ser Thr Val Asp His Gln Gly Val Ser Trp Tyr His Trp

```
               4250                4255                4260
Lys Gly Phe Glu Phe Ser Val Pro Phe Thr Glu Met Lys Leu Arg
           4265                4270                4275
Pro Arg Asn Phe Arg Ser Pro Ala Gly Gly Gly
           4280                4285

<210> SEQ ID NO 9
<211> LENGTH: 613
<212> TYPE: PRT
<213> ORGANISM: Homo sapiens

<400> SEQUENCE: 9

Met Phe Arg Cys Gly Gly Leu Ala Ala Gly Ala Leu Lys Gln Lys Leu
1               5                   10                  15

Val Pro Leu Val Arg Thr Val Cys Val Arg Ser Pro Arg Gln Arg Asn
            20                  25                  30

Arg Leu Pro Gly Asn Leu Phe Gln Arg Trp His Val Pro Leu Glu Leu
        35                  40                  45

Gln Met Thr Arg Gln Met Ala Ser Ser Gly Ala Ser Gly Gly Lys Ile
    50                  55                  60

Asp Asn Ser Val Leu Val Leu Ile Val Gly Leu Ser Thr Val Gly Ala
65                  70                  75                  80

Gly Ala Tyr Ala Tyr Lys Thr Met Lys Glu Asp Glu Lys Arg Tyr Asn
                85                  90                  95

Glu Arg Ile Ser Gly Leu Gly Leu Thr Pro Glu Gln Lys Gln Lys Lys
            100                 105                 110

Ala Ala Leu Ser Ala Ser Glu Gly Glu Glu Val Pro Gln Asp Lys Ala
        115                 120                 125

Pro Ser His Val Pro Phe Leu Leu Ile Gly Gly Thr Ala Ala Phe
    130                 135                 140

Ala Ala Ala Arg Ser Ile Arg Ala Arg Asp Pro Gly Ala Arg Val Leu
145                 150                 155                 160

Ile Val Ser Glu Asp Pro Glu Leu Pro Tyr Met Arg Pro Pro Leu Ser
                165                 170                 175

Lys Glu Leu Trp Phe Ser Asp Asp Pro Asn Val Thr Lys Thr Leu Arg
            180                 185                 190

Phe Lys Gln Trp Asn Gly Lys Glu Arg Ser Ile Tyr Phe Gln Pro Pro
        195                 200                 205

Ser Phe Tyr Val Ser Ala Gln Asp Leu Pro His Ile Glu Asn Gly Gly
    210                 215                 220

Val Ala Val Leu Thr Gly Lys Lys Val Val Gln Leu Asp Val Arg Asp
225                 230                 235                 240

Asn Met Val Lys Leu Asn Asp Gly Ser Gln Ile Thr Tyr Glu Lys Cys
                245                 250                 255

Leu Ile Ala Thr Gly Gly Thr Pro Arg Ser Leu Ser Ala Ile Asp Arg
            260                 265                 270

Ala Gly Ala Glu Val Lys Ser Arg Thr Thr Leu Phe Arg Lys Ile Gly
        275                 280                 285

Asp Phe Arg Ser Leu Glu Lys Ile Ser Arg Glu Val Lys Ser Ile Thr
    290                 295                 300

Ile Ile Gly Gly Gly Phe Leu Gly Ser Glu Leu Ala Cys Ala Leu Gly
305                 310                 315                 320

Arg Lys Ala Arg Ala Leu Gly Thr Glu Val Ile Gln Leu Phe Pro Glu
                325                 330                 335
```

```
Lys Gly Asn Met Gly Lys Ile Leu Pro Glu Tyr Leu Ser Asn Trp Thr
                340                 345                 350

Met Glu Lys Val Arg Arg Glu Gly Val Lys Val Met Pro Asn Ala Ile
            355                 360                 365

Val Gln Ser Val Gly Val Ser Ser Gly Lys Leu Leu Ile Lys Leu Lys
        370                 375                 380

Asp Gly Arg Lys Val Glu Thr Asp His Ile Val Ala Ala Val Gly Leu
385                 390                 395                 400

Glu Pro Asn Val Glu Leu Ala Lys Thr Gly Gly Leu Glu Ile Asp Ser
                405                 410                 415

Asp Phe Gly Gly Phe Arg Val Asn Ala Glu Leu Gln Ala Arg Ser Asn
            420                 425                 430

Ile Trp Val Ala Gly Asp Ala Ala Cys Phe Tyr Asp Ile Lys Leu Gly
        435                 440                 445

Arg Arg Arg Val Glu His His Asp His Ala Val Val Ser Gly Arg Leu
450                 455                 460

Ala Gly Glu Asn Met Thr Gly Ala Ala Lys Pro Tyr Trp His Gln Ser
465                 470                 475                 480

Met Phe Trp Ser Asp Leu Gly Pro Asp Val Gly Tyr Glu Ala Ile Gly
            485                 490                 495

Leu Val Asp Ser Ser Leu Pro Thr Val Gly Val Phe Ala Lys Ala Thr
        500                 505                 510

Ala Gln Asp Asn Pro Lys Ser Ala Thr Glu Gln Ser Gly Thr Gly Ile
            515                 520                 525

Arg Ser Glu Ser Glu Thr Glu Ser Glu Ala Ser Glu Ile Thr Ile Pro
530                 535                 540

Pro Ser Thr Pro Ala Val Pro Gln Ala Pro Val Gln Gly Glu Asp Tyr
545                 550                 555                 560

Gly Lys Gly Val Ile Phe Tyr Leu Arg Asp Lys Val Val Val Gly Ile
            565                 570                 575

Val Leu Trp Asn Ile Phe Asn Arg Met Pro Ile Ala Arg Lys Ile Ile
        580                 585                 590

Lys Asp Gly Glu Gln His Glu Asp Leu Asn Glu Val Ala Lys Leu Phe
            595                 600                 605

Asn Ile His Glu Asp
        610

<210> SEQ ID NO 10
<211> LENGTH: 291
<212> TYPE: PRT
<213> ORGANISM: Homo sapiens

<400> SEQUENCE: 10

Met Gln Arg Ala Arg Pro Thr Leu Trp Ala Ala Ala Leu Thr Leu Leu
1               5                   10                  15

Val Leu Leu Arg Gly Pro Pro Val Ala Arg Ala Gly Ala Ser Ser Ala
            20                  25                  30

Gly Leu Gly Pro Val Val Arg Cys Glu Pro Cys Asp Ala Arg Ala Leu
        35                  40                  45

Ala Gln Cys Ala Pro Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
            85                  90                  95
```

-continued

```
Ser Pro Asp Glu Ala Arg Pro Leu Gln Ala Leu Leu Asp Gly Arg Gly
            100                 105                 110

Leu Cys Val Asn Ala Ser Ala Val Ser Arg Leu Arg Ala Tyr Leu Leu
        115                 120                 125

Pro Ala Pro Pro Ala Pro Gly Asn Ala Ser Glu Ser Glu Asp Arg
130                 135                 140

Ser Ala Gly Ser Val Glu Ser Pro Ser Val Ser Ser Thr His Arg Val
145                 150                 155                 160

Ser Asp Pro Lys Phe His Pro Leu His Ser Lys Ile Ile Ile Lys
                165                 170                 175

Lys Gly His Ala Lys Asp Ser Gln Arg Tyr Lys Val Asp Tyr Glu Ser
            180                 185                 190

Gln Ser Thr Asp Thr Gln Asn Phe Ser Ser Glu Ser Lys Arg Glu Thr
        195                 200                 205

Glu Tyr Gly Pro Cys Arg Arg Glu Met Glu Asp Thr Leu Asn His Leu
    210                 215                 220

Lys Phe Leu Asn Val Leu Ser Pro Arg Gly Val His Ile Pro Asn Cys
225                 230                 235                 240

Asp Lys Lys Gly Phe Tyr Lys Lys Gln Cys Arg Pro Ser Lys Gly
                245                 250                 255

Arg Lys Arg Gly Phe Cys Trp Cys Val Asp Lys Tyr Gly Gln Pro Leu
            260                 265                 270

Pro Gly Tyr Thr Thr Lys Gly Lys Glu Asp Val His Cys Tyr Ser Met
        275                 280                 285

Gln Ser Lys
    290

<210> SEQ ID NO 11
<211> LENGTH: 1373
<212> TYPE: PRT
<213> ORGANISM: Homo sapiens

<400> SEQUENCE: 11

Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
            20                  25                  30

Gly Ala Ser Gln Ala Gly Ala Pro Gln Gly Arg Val Pro Glu Ala Arg
        35                  40                  45

Pro Asn Ser Met Val Val Glu His Pro Glu Phe Leu Lys Ala Gly Lys
    50                  55                  60

Glu Pro Gly Leu Gln Ile Trp Arg Val Glu Lys Phe Asp Leu Val Pro
65                  70                  75                  80

Val Pro Thr Asn Leu Tyr Gly Asp Phe Phe Thr Gly Asp Ala Tyr Val
                85                  90                  95

Ile Leu Lys Thr Val Gln Leu Arg Asn Gly Asn Leu Gln Tyr Asp Leu
            100                 105                 110

His Tyr Trp Leu Gly Asn Glu Cys Ser Gln Asp Glu Ser Gly Ala Ala
        115                 120                 125

Ala Ile Phe Thr Val Gln Leu Asp Asp Tyr Leu Asn Gly Arg Ala Val
    130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Gly Val Ala Ser Gly Phe
```

```
                165                 170                 175
Lys His Val Val Pro Asn Glu Val Val Gln Arg Leu Phe Gln Val
                180                 185                 190

Lys Gly Arg Arg Val Val Arg Ala Thr Glu Val Pro Val Ser Trp Glu
    195                 200                 205

Ser Phe Asn Asn Gly Asp Cys Phe Ile Leu Asp Leu Gly Asn Asn Ile
    210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Gly Thr Glu Pro Glu Ala Met Leu Gln
                260                 265                 270

Val Leu Gly Pro Lys Pro Ala Leu Pro Ala Gly Thr Glu Asp Thr Ala
            275                 280                 285

Lys Glu Asp Ala Ala Asn Arg Lys Leu Ala Lys Leu Tyr Lys Val Ser
            290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
            340                 345                 350

Glu Glu Arg Lys Ala Ala Leu Lys Thr Ala Ser Asp Phe Ile Thr Lys
            355                 360                 365

Met Asp Tyr Pro Lys Gln Thr Gln Val Ser Val Leu Pro Glu Gly Gly
        370                 375                 380

Glu Thr Pro Leu Phe Lys Gln Phe Phe Lys Asn Trp Arg Asp Pro Asp
385                 390                 395                 400

Gln Thr Asp Gly Leu Gly Leu Ser Tyr Leu Ser Ser His Ile Ala Asn
            405                 410                 415

Val Glu Arg Val Pro Phe Asp Ala Ala Thr Leu His Thr Ser Thr Ala
            420                 425                 430

Met Ala Ala Gln His Gly Met Asp Asp Asp Gly Thr Gly Gln Lys Gln
        435                 440                 445

Ile Trp Arg Ile Glu Gly Ser Asn Lys Val Pro Val Asp Pro Ala Thr
450                 455                 460

Tyr Gly Gln Phe Tyr Gly Gly Asp Ser Tyr Ile Ile Leu Tyr Asn Tyr
465                 470                 475                 480

Arg His Gly Gly Arg Gln Gly Gln Ile Ile Tyr Asn Trp Gln Gly Ala
            485                 490                 495

Gln Ser Thr Gln Asp Glu Val Ala Ala Ser Ala Ile Leu Thr Ala Gln
        500                 505                 510

Leu Asp Glu Glu Leu Gly Gly Thr Pro Val Gln Ser Arg Val Val Gln
        515                 520                 525

Gly Lys Glu Pro Ala His Leu Met Ser Leu Phe Gly Gly Lys Pro Met
        530                 535                 540

Ile Ile Tyr Lys Gly Gly Thr Ser Arg Glu Gly Gly Asn Thr Ala Pro
545                 550                 555                 560

Ala Ser Thr Arg Leu Phe Gln Val Arg Ala Asn Ser Ala Gly Ala Thr
            565                 570                 575

Arg Ala Val Glu Val Leu Pro Lys Ala Gly Ala Leu Asn Ser Asn Asp
        580                 585                 590
```

```
Ala Phe Val Leu Lys Thr Pro Ser Ala Ala Tyr Leu Trp Val Gly Thr
        595                 600                 605

Gly Ala Ser Glu Ala Glu Lys Thr Gly Ala Gln Glu Leu Leu Arg Val
        610                 615                 620

Leu Arg Ala Gln Pro Val Gln Val Ala Glu Gly Ser Glu Pro Asp Gly
625                 630                 635                 640

Phe Trp Glu Ala Leu Gly Gly Lys Ala Ala Tyr Arg Thr Ser Pro Arg
                645                 650                 655

Leu Lys Asp Lys Lys Met Asp Ala His Pro Pro Arg Leu Phe Ala Cys
                660                 665                 670

Ser Asn Lys Ile Gly Arg Phe Val Ile Glu Val Pro Gly Glu Leu
        675                 680                 685

Met Gln Glu Asp Leu Ala Thr Asp Asp Val Met Leu Leu Asp Thr Trp
        690                 695                 700

Asp Gln Val Phe Val Trp Val Gly Lys Asp Ser Gln Glu Glu Glu Lys
705                 710                 715                 720

Thr Glu Ala Leu Thr Ser Ala Lys Arg Tyr Ile Glu Thr Asp Pro Ala
                725                 730                 735

Asn Arg Asp Arg Arg Thr Pro Ile Thr Val Val Lys Gln Gly Phe Glu
                740                 745                 750

Pro Pro Ser Phe Val Gly Trp Phe Leu Gly Trp Asp Asp Asp Tyr Trp
        755                 760                 765

Ser Val Asp Pro Leu Asp Arg Ala Met Ala Glu Leu Ala Ala Gly Cys
        770                 775                 780

Gly Cys Gly Cys Cys Gly Cys Thr Gly Cys Ala Gly Gly Cys Gly
785                 790                 795                 800

Cys Thr Gly Cys Thr Gly Gly Ala Thr Gly Gly Cys Cys Gly Cys Gly
                805                 810                 815

Gly Cys Cys Thr Gly Thr Gly Cys Gly Thr Gly Ala Ala Cys Gly Cys
                820                 825                 830

Gly Ala Gly Cys Gly Cys Gly Gly Thr Gly Ala Gly Cys Cys Gly Cys
        835                 840                 845

Cys Thr Gly Cys Gly Cys Gly Cys Gly Thr Ala Thr Cys Thr Gly Cys
        850                 855                 860

Thr Gly Cys Cys Gly Gly Cys Gly Cys Gly Cys Cys Gly Gly Cys
865                 870                 875                 880

Gly Cys Cys Gly Gly Gly Cys Gly Ala Ala Cys Cys Gly Cys Cys Gly
                885                 890                 895

Gly Cys Gly Cys Cys Gly Gly Cys Ala Ala Cys Gly Cys Gly Ala
                900                 905                 910

Gly Cys Gly Ala Ala Ala Gly Cys Gly Ala Ala Gly Ala Ala Gly Ala
        915                 920                 925

Thr Cys Gly Cys Ala Gly Cys Gly Cys Gly Gly Gly Cys Ala Gly Cys
        930                 935                 940

Gly Thr Gly Gly Ala Ala Ala Gly Cys Cys Cys Gly Ala Gly Cys Gly
945                 950                 955                 960

Thr Gly Ala Gly Cys Ala Gly Cys Ala Cys Cys Ala Thr Cys Gly
                965                 970                 975

Cys Gly Thr Gly Ala Gly Cys Gly Ala Thr Cys Cys Gly Ala Ala Ala
                980                 985                 990

Thr Thr Thr Cys Ala Thr Cys Cys  Gly Cys Thr Gly Cys  Ala Thr Ala
        995                 1000                1005
```

Gly Cys Ala Ala Ala Ala Thr Thr Ala Thr Thr Ala Thr Thr Ala
1010                1015                1020

Thr Thr Ala Ala Ala Ala Ala Ala Gly Gly Cys Cys Ala Thr Gly
1025                1030                1035

Cys Gly Ala Ala Ala Gly Ala Thr Ala Gly Cys Cys Ala Gly Cys
1040                1045                1050

Gly Cys Thr Ala Thr Ala Ala Ala Gly Thr Gly Gly Ala Thr Thr
1055                1060                1065

Ala Thr Gly Ala Ala Ala Gly Cys Cys Ala Gly Ala Gly Cys Ala
1070                1075                1080

Cys Cys Gly Ala Thr Ala Cys Cys Cys Ala Gly Ala Ala Cys Thr
1085                1090                1095

Thr Thr Ala Gly Cys Ala Gly Cys Gly Ala Ala Ala Gly Cys Ala
1100                1105                1110

Ala Ala Cys Gly Cys Gly Ala Ala Ala Cys Cys Gly Ala Ala Thr
1115                1120                1125

Ala Thr Gly Gly Cys Cys Cys Gly Thr Gly Cys Cys Gly Cys Cys
1130                1135                1140

Gly Cys Gly Ala Ala Ala Thr Gly Gly Ala Ala Gly Ala Thr Ala
1145                1150                1155

Cys Cys Cys Thr Gly Ala Ala Cys Cys Ala Thr Cys Thr Gly Ala
1160                1165                1170

Ala Ala Thr Thr Thr Cys Thr Gly Ala Ala Cys Gly Thr Gly Cys
1175                1180                1185

Thr Gly Ala Gly Cys Cys Cys Gly Cys Gly Cys Gly Gly Cys Gly
1190                1195                1200

Thr Gly Cys Ala Thr Ala Thr Thr Cys Cys Gly Ala Ala Cys Thr
1205                1210                1215

Gly Cys Gly Ala Thr Ala Ala Ala Ala Ala Gly Gly Cys Thr
1220                1225                1230

Thr Thr Thr Ala Thr Ala Ala Ala Ala Ala Ala Ala Ala Ala Cys
1235                1240                1245

Ala Gly Thr Gly Cys Cys Gly Cys Cys Cys Gly Ala Gly Cys Ala
1250                1255                1260

Ala Ala Gly Gly Cys Cys Gly Cys Ala Ala Cys Gly Cys Gly
1265                1270                1275

Gly Cys Thr Thr Thr Thr Gly Cys Thr Gly Gly Thr Gly Cys Gly
1280                1285                1290

Thr Gly Gly Ala Thr Ala Ala Thr Ala Thr Gly Gly Cys Cys
1295                1300                1305

Ala Gly Cys Cys Gly Cys Thr Gly Cys Cys Gly Gly Gly Cys Thr
1310                1315                1320

Ala Thr Ala Cys Cys Ala Cys Cys Ala Ala Gly Gly Cys Ala
1325                1330                1335

Ala Ala Gly Ala Ala Gly Ala Thr Gly Thr Gly Cys Ala Thr Thr
1340                1345                1350

Gly Cys Thr Ala Thr Ala Gly Cys Ala Thr Gly Cys Ala Gly Ala
1355                1360                1365

Gly Cys Ala Ala Ala
1370

<210> SEQ ID NO 12
<211> LENGTH: 699
<212> TYPE: PRT

<213> ORGANISM: Homo sapiens

<400> SEQUENCE: 12

```
Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
        355                 360                 365

Ala Pro Gly Glu Leu Glu His Gly Leu Ile Thr Phe Ser Thr Arg Asn
    370                 375                 380

Asn Leu Thr Thr Tyr Lys Ser Glu Ile Lys Tyr Ser Cys Gln Glu Pro
385                 390                 395                 400
```

-continued

Tyr Tyr Lys Met Leu Asn Asn Asn Thr Gly Ile Tyr Thr Cys Ser Ala
        405                 410                 415

Gln Gly Val Trp Met Asn Lys Val Leu Gly Arg Ser Leu Pro Thr Cys
    420                 425                 430

Leu Pro Val Cys Gly Leu Pro Lys Phe Ser Arg Lys Leu Met Ala Arg
            435                 440                 445

Ile Phe Asn Gly Arg Pro Ala Gln Lys Gly Thr Thr Pro Trp Ile Ala
450                 455                 460

Met Leu Ser His Leu Asn Gly Gln Pro Phe Cys Gly Gly Ser Leu Leu
465                 470                 475                 480

Gly Ser Ser Trp Ile Val Thr Ala Ala His Cys Leu His Gln Ser Leu
                485                 490                 495

Asp Pro Glu Asp Pro Thr Leu Arg Asp Ser Asp Leu Leu Ser Pro Ser
            500                 505                 510

Asp Phe Lys Ile Ile Leu Gly Lys His Trp Arg Leu Arg Ser Asp Glu
        515                 520                 525

Asn Glu Gln His Leu Gly Val Lys His Thr Thr Leu His Pro Gln Tyr
    530                 535                 540

Asp Pro Asn Thr Phe Glu Asn Asp Val Ala Leu Val Glu Leu Leu Glu
545                 550                 555                 560

Ser Pro Val Leu Asn Ala Phe Val Met Pro Ile Cys Leu Pro Glu Gly
                565                 570                 575

Pro Gln Gln Glu Gly Ala Met Val Ile Val Ser Gly Trp Gly Lys Gln
            580                 585                 590

Phe Leu Gln Arg Phe Pro Glu Thr Leu Met Glu Ile Glu Ile Pro Ile
        595                 600                 605

Val Asp His Ser Thr Cys Gln Lys Ala Tyr Ala Pro Leu Lys Lys Lys
    610                 615                 620

Val Thr Arg Asp Met Ile Cys Ala Gly Glu Lys Gly Gly Lys Asp
625                 630                 635                 640

Ala Cys Ala Gly Asp Ser Gly Gly Pro Met Val Thr Leu Asn Arg Glu
                645                 650                 655

Arg Gly Gln Trp Tyr Leu Val Gly Thr Val Ser Trp Gly Asp Asp Cys
            660                 665                 670

Gly Lys Lys Asp Arg Tyr Gly Val Tyr Ser Tyr Ile His His Asn Lys
        675                 680                 685

Asp Trp Ile Gln Arg Val Thr Gly Val Arg Asn
    690                 695

<210> SEQ ID NO 13
<211> LENGTH: 1754
<212> TYPE: PRT
<213> ORGANISM: Homo sapiens

<400> SEQUENCE: 13

Met Ala Pro Tyr Pro Cys Gly Cys His Ile Leu Leu Leu Phe Cys
1               5                   10                  15

Cys Leu Ala Ala Ala Arg Ala Asn Leu Leu Asn Leu Asn Trp Leu Trp
            20                  25                  30

Phe Asn Asn Glu Asp Thr Ser His Ala Ala Thr Thr Ile Pro Glu Pro
        35                  40                  45

Gln Gly Pro Leu Pro Val Gln Pro Thr Ala Asp Thr Thr His Val
    50                  55                  60

Thr Pro Arg Asn Gly Ser Thr Glu Pro Ala Thr Ala Pro Gly Ser Pro
65                  70                  75                  80

```
Glu Pro Pro Ser Glu Leu Leu Glu Asp Gly Gln Asp Thr Pro Thr Ser
                85                  90                  95

Ala Glu Ser Pro Asp Ala Pro Glu Glu Asn Ile Ala Gly Val Gly Ala
            100                 105                 110

Glu Ile Leu Asn Val Ala Lys Gly Ile Arg Ser Phe Val Gln Leu Trp
        115                 120                 125

Asn Asp Thr Val Pro Thr Glu Ser Leu Ala Arg Ala Glu Thr Leu Val
    130                 135                 140

Leu Glu Thr Pro Val Gly Pro Leu Ala Leu Ala Gly Pro Ser Ser Thr
145                 150                 155                 160

Pro Gln Glu Asn Gly Thr Thr Leu Trp Pro Ser Arg Gly Ile Pro Ser
                165                 170                 175

Ser Pro Gly Ala His Thr Thr Glu Ala Gly Thr Leu Pro Ala Pro Thr
            180                 185                 190

Pro Ser Pro Pro Ser Leu Gly Arg Pro Trp Ala Pro Leu Thr Gly Pro
        195                 200                 205

Ser Val Pro Pro Pro Ser Ser Gly Arg Ala Ser Leu Ser Ser Leu Leu
    210                 215                 220

Gly Gly Ala Pro Pro Trp Gly Ser Leu Gln Asp Pro Asp Ser Gln Gly
225                 230                 235                 240

Leu Ser Pro Ala Ala Ala Pro Ser Gln Gln Leu Gln Arg Pro Arg Asp
                245                 250                 255

Val Arg Leu Arg Thr Pro Leu Leu His Pro Leu Val Met Gly Ser Leu
            260                 265                 270

Gly Lys His Ala Ala Pro Ser Ala Phe Ser Ser Gly Leu Pro Gly Ala
        275                 280                 285

Leu Ser Gln Val Ala Val Thr Thr Leu Thr Arg Asp Ser Gly Ala Trp
    290                 295                 300

Val Ser His Val Ala Asn Ser Val Gly Pro Gly Leu Ala Asn Asn Ser
305                 310                 315                 320

Ala Leu Leu Gly Ala Asp Pro Glu Ala Pro Ala Gly Arg Cys Leu Pro
                325                 330                 335

Leu Pro Pro Ser Leu Pro Val Cys Gly His Leu Gly Ile Ser Arg Phe
            340                 345                 350

Trp Leu Pro Asn His Leu His His Glu Ser Gly Glu Gln Val Arg Ala
        355                 360                 365

Gly Ala Arg Ala Trp Gly Gly Leu Leu Gln Thr His Cys His Pro Phe
    370                 375                 380

Leu Ala Trp Phe Phe Cys Leu Leu Leu Val Pro Cys Gly Ser Val
385                 390                 395                 400

Pro Pro Pro Ala Pro Pro Cys Cys Gln Phe Cys Glu Ala Leu Gln
                405                 410                 415

Asp Ala Cys Trp Ser Arg Leu Gly Gly Gly Arg Leu Pro Val Ala Cys
            420                 425                 430

Ala Ser Leu Pro Thr Gln Glu Asp Gly Tyr Cys Val Leu Ile Gly Pro
        435                 440                 445

Ala Ala Glu Arg Ile Ser Glu Glu Val Gly Leu Leu Gln Leu Leu Gly
    450                 455                 460

Asp Pro Pro Pro Gln Gln Val Thr Gln Thr Asp Asp Pro Asp Val Gly
465                 470                 475                 480

Leu Ala Tyr Val Phe Gly Pro Asp Ala Asn Ser Gly Gln Val Ala Arg
                485                 490                 495
```

-continued

```
Tyr His Phe Pro Ser Leu Phe Phe Arg Asp Phe Ser Leu Leu Phe His
            500                 505                 510

Ile Arg Pro Ala Thr Glu Gly Pro Gly Val Leu Phe Ala Ile Thr Asp
        515                 520                 525

Ser Ala Gln Ala Met Val Leu Leu Gly Val Lys Leu Ser Gly Val Gln
    530                 535                 540

Asp Gly His Gln Asp Ile Ser Leu Leu Tyr Thr Glu Pro Gly Ala Gly
545                 550                 555                 560

Gln Thr His Thr Ala Ala Ser Phe Arg Leu Pro Ala Phe Val Gly Gln
                565                 570                 575

Trp Thr His Leu Ala Leu Ser Val Ala Gly Gly Phe Val Ala Leu Tyr
            580                 585                 590

Val Asp Cys Glu Glu Phe Gln Arg Met Pro Leu Ala Arg Ser Ser Arg
        595                 600                 605

Gly Leu Glu Leu Glu Pro Gly Ala Gly Leu Phe Val Ala Gln Ala Gly
    610                 615                 620

Gly Ala Asp Pro Asp Lys Phe Gln Gly Val Ile Ala Glu Leu Lys Val
625                 630                 635                 640

Arg Arg Asp Pro Gln Val Ser Pro Met His Cys Leu Asp Glu Glu Gly
                645                 650                 655

Asp Asp Ser Asp Gly Ala Ser Gly Asp Ser Gly Ser Gly Leu Gly Asp
            660                 665                 670

Ala Arg Glu Leu Leu Arg Glu Thr Gly Ala Ala Leu Lys Pro Arg
        675                 680                 685

Leu Pro Ala Pro Pro Val Thr Thr Pro Pro Leu Ala Gly Gly Ser
    690                 695                 700

Ser Thr Glu Asp Ser Arg Ser Glu Glu Val Glu Glu Gln Thr Thr Val
705                 710                 715                 720

Ala Ser Leu Gly Ala Gln Thr Leu Pro Gly Ser Asp Ser Val Ser Thr
                725                 730                 735

Trp Asp Gly Ser Val Arg Thr Pro Gly Gly Arg Val Lys Glu Gly Gly
            740                 745                 750

Leu Lys Gly Gln Lys Gly Glu Pro Gly Val Pro Gly Pro Gly Arg
        755                 760                 765

Ala Gly Pro Pro Gly Ser Pro Cys Leu Pro Gly Pro Pro Gly Leu Pro
    770                 775                 780

Cys Pro Val Ser Pro Leu Gly Pro Ala Gly Pro Ala Leu Gln Thr Val
785                 790                 795                 800

Pro Gly Pro Gln Gly Pro Pro Gly Pro Pro Gly Arg Asp Gly Thr Pro
                805                 810                 815

Gly Arg Asp Gly Glu Pro Gly Asp Pro Gly Glu Asp Gly Lys Pro Gly
            820                 825                 830

Asp Thr Gly Pro Gln Gly Phe Pro Gly Thr Pro Gly Asp Val Gly Pro
        835                 840                 845

Lys Gly Asp Lys Gly Asp Pro Gly Val Gly Glu Arg Gly Pro Pro Gly
    850                 855                 860

Pro Gln Gly Pro Pro Gly Pro Pro Gly Pro Ser Phe Arg His Asp Lys
865                 870                 875                 880

Leu Thr Phe Ile Asp Met Glu Gly Ser Gly Phe Gly Gly Asp Leu Glu
                885                 890                 895

Ala Leu Arg Gly Pro Arg Gly Phe Pro Gly Pro Pro Gly Pro Pro Gly
            900                 905                 910

Val Pro Gly Leu Pro Gly Glu Pro Gly Arg Phe Gly Val Asn Ser Ser
```

```
            915                 920                 925
Asp Val Pro Gly Pro Ala Gly Leu Pro Gly Val Pro Gly Arg Glu Gly
            930                 935                 940

Pro Pro Gly Phe Pro Gly Leu Pro Gly Pro Pro Gly Pro Pro Gly Arg
945                 950                 955                 960

Glu Gly Pro Pro Gly Arg Thr Gly Gln Lys Gly Ser Leu Gly Glu Ala
                965                 970                 975

Gly Ala Pro Gly His Lys Gly Ser Lys Gly Ala Pro Gly Pro Ala Gly
            980                 985                 990

Ala Arg Gly Glu Ser Gly Leu Ala Gly Ala Pro Gly Pro Ala Gly Pro
            995                 1000                1005

Pro Gly Pro Pro Gly Pro Pro Gly Pro Pro Gly Pro Gly Leu Pro
        1010                1015                1020

Ala Gly Phe Asp Asp Met Glu Gly Ser Gly Gly Pro Phe Trp Ser
        1025                1030                1035

Thr Ala Arg Ser Ala Asp Gly Pro Gln Gly Pro Pro Gly Leu Pro
        1040                1045                1050

Gly Leu Lys Gly Asp Pro Gly Val Pro Gly Leu Pro Gly Ala Lys
        1055                1060                1065

Gly Glu Val Gly Ala Asp Gly Val Pro Gly Phe Pro Gly Leu Pro
        1070                1075                1080

Gly Arg Glu Gly Ile Ala Gly Pro Gln Gly Pro Lys Gly Asp Arg
        1085                1090                1095

Gly Ser Arg Gly Glu Lys Gly Asp Pro Gly Lys Asp Gly Val Gly
        1100                1105                1110

Gln Pro Gly Leu Pro Gly Pro Pro Gly Pro Pro Gly Pro Val Val
        1115                1120                1125

Tyr Val Ser Glu Gln Asp Gly Ser Val Leu Ser Val Pro Gly Pro
        1130                1135                1140

Glu Gly Arg Pro Gly Phe Ala Gly Phe Pro Gly Pro Ala Gly Pro
        1145                1150                1155

Lys Gly Asn Leu Gly Ser Lys Gly Glu Arg Gly Ser Pro Gly Pro
        1160                1165                1170

Lys Gly Glu Lys Gly Glu Pro Gly Ser Ile Phe Ser Pro Asp Gly
        1175                1180                1185

Gly Ala Leu Gly Pro Ala Gln Lys Gly Ala Lys Gly Glu Pro Gly
        1190                1195                1200

Phe Arg Gly Pro Pro Gly Pro Tyr Gly Arg Pro Gly Tyr Lys Gly
        1205                1210                1215

Glu Ile Gly Phe Pro Gly Arg Pro Gly Arg Pro Gly Met Asn Gly
        1220                1225                1230

Leu Lys Gly Glu Lys Gly Glu Pro Gly Asp Ala Ser Leu Gly Phe
        1235                1240                1245

Gly Met Arg Gly Met Pro Gly Pro Pro Gly Pro Pro Gly Pro Pro
        1250                1255                1260

Gly Pro Pro Gly Thr Pro Val Tyr Asp Ser Asn Val Phe Ala Glu
        1265                1270                1275

Ser Ser Arg Pro Gly Pro Pro Gly Leu Pro Gly Asn Gln Gly Pro
        1280                1285                1290

Pro Gly Pro Lys Gly Ala Lys Gly Glu Val Gly Pro Pro Gly Pro
        1295                1300                1305

Pro Gly Gln Phe Pro Phe Asp Phe Leu Gln Leu Glu Ala Glu Met
        1310                1315                1320
```

-continued

Lys Gly Glu Lys Gly Asp Arg Gly Asp Ala Gly Gln Lys Gly Glu
1325                1330                1335

Arg Gly Glu Pro Gly Gly Gly Phe Phe Gly Ser Ser Leu Pro
1340                1345                1350

Gly Pro Pro Gly Pro Pro Gly Pro Pro Gly Pro Arg Gly Tyr Pro
1355                1360                1365

Gly Ile Pro Gly Pro Lys Gly Glu Ser Ile Arg Gly Gln Pro Gly
1370                1375                1380

Pro Pro Gly Pro Gln Gly Pro Pro Gly Ile Gly Tyr Glu Gly Arg
1385                1390                1395

Gln Gly Pro Pro Gly Pro Pro Gly Pro Pro Gly Pro Pro Ser Phe
1400                1405                1410

Pro Gly Pro His Arg Gln Thr Ile Ser Val Pro Gly Pro Pro Gly
1415                1420                1425

Pro Pro Gly Pro Pro Gly Pro Gly Thr Met Gly Ala Ser Ser
1430                1435                1440

Gly Val Arg Leu Trp Ala Thr Arg Gln Ala Met Leu Gly Gln Val
1445                1450                1455

His Glu Val Pro Glu Gly Trp Leu Ile Phe Val Ala Glu Gln Glu
1460                1465                1470

Glu Leu Tyr Val Arg Val Gln Asn Gly Phe Arg Lys Val Gln Leu
1475                1480                1485

Glu Ala Arg Thr Pro Leu Pro Arg Gly Thr Asp Asn Glu Val Ala
1490                1495                1500

Ala Leu Gln Pro Pro Val Val Gln Leu His Asp Ser Asn Pro Tyr
1505                1510                1515

Pro Arg Arg Glu His Pro His Pro Thr Ala Arg Pro Trp Arg Ala
1520                1525                1530

Asp Asp Ile Leu Ala Ser Pro Pro Arg Leu Pro Glu Pro Gln Pro
1535                1540                1545

Tyr Pro Gly Ala Pro His His Ser Ser Tyr Val His Leu Arg Pro
1550                1555                1560

Ala Arg Pro Thr Ser Pro Pro Ala His Ser His Arg Asp Phe Gln
1565                1570                1575

Pro Val Leu His Leu Val Ala Leu Asn Ser Pro Leu Ser Gly Gly
1580                1585                1590

Met Arg Gly Ile Arg Gly Ala Asp Phe Gln Cys Phe Gln Gln Ala
1595                1600                1605

Arg Ala Val Gly Leu Ala Gly Thr Phe Arg Ala Phe Leu Ser Ser
1610                1615                1620

Arg Leu Gln Asp Leu Tyr Ser Ile Val Arg Arg Ala Asp Arg Ala
1625                1630                1635

Ala Val Pro Ile Val Asn Leu Lys Asp Glu Leu Leu Phe Pro Ser
1640                1645                1650

Trp Glu Ala Leu Phe Ser Gly Ser Glu Gly Pro Leu Lys Pro Gly
1655                1660                1665

Ala Arg Ile Phe Ser Phe Asp Gly Lys Asp Val Leu Arg His Pro
1670                1675                1680

Thr Trp Pro Gln Lys Ser Val Trp His Gly Ser Asp Pro Asn Gly
1685                1690                1695

Arg Arg Leu Thr Glu Ser Tyr Cys Glu Thr Trp Arg Thr Glu Ala
1700                1705                1710

-continued

```
Pro Ser Ala Thr Gly Gln Ala Ser Ser Leu Leu Gly Gly Arg Leu
    1715                1720                1725

Leu Gly Gln Ser Ala Ala Ser Cys His His Ala Tyr Ile Val Leu
    1730                1735                1740

Cys Ile Glu Asn Ser Phe Met Thr Ala Ser Lys
    1745                1750

<210> SEQ ID NO 14
<211> LENGTH: 654
<212> TYPE: PRT
<213> ORGANISM: Homo sapiens

<400> SEQUENCE: 14

Met Lys Leu Ser Leu Val Ala Ala Met Leu Leu Leu Ser Ala Ala
1               5                   10                  15

Arg Ala Glu Glu Glu Asp Lys Lys Glu Asp Val Gly Thr Val Val
                20                  25                  30

Ile Asp Leu Gly Thr Thr Tyr Ser Cys Val Gly Val Phe Lys Asn
                35                  40                  45

Arg Val Glu Ile Ile Ala Asn Asp Gln Gly Asn Arg Ile Thr Pro Ser
    50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
                100                 105                 110

Lys Phe Leu Pro Phe Lys Val Val Glu Lys Lys Thr Lys Pro Tyr Ile
            115                 120                 125

Gln Val Asp Ile Gly Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
                180                 185                 190

Leu Asn Val Met Arg Ile Ile Asn Glu Pro Thr Ala Ala Ala Ile Ala
            195                 200                 205

Tyr Gly Leu Asp Lys Arg Glu Gly Glu Lys Asn Ile Leu Val Phe Asp
    210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
                260                 265                 270

Lys Thr Gly Lys Asp Val Arg Lys Asp Asn Arg Ala Val Gln Lys Leu
            275                 280                 285

Arg Arg Glu Val Glu Lys Ala Lys Arg Ala Leu Ser Ser Gln His Gln
    290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335
```

```
Ser Thr Met Lys Pro Val Gln Lys Val Leu Glu Asp Ser Asp Leu Lys
            340                 345                 350

Lys Ser Asp Ile Asp Glu Ile Val Leu Val Gly Ser Thr Arg Ile
        355                 360                 365

Pro Lys Ile Gln Gln Leu Val Lys Glu Phe Phe Asn Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Val Pro Thr Lys Lys Ser
        435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
            500                 505                 510

Ala Glu Asp Lys Gly Thr Gly Asn Lys Asn Lys Ile Thr Ile Thr Asn
        515                 520                 525

Asp Gln Asn Arg Leu Thr Pro Glu Glu Ile Glu Arg Met Val Asn Asp
    530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
                565                 570                 575

Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
        595                 600                 605

Gln Asp Ala Asp Ile Glu Asp Phe Lys Ala Lys Lys Lys Glu Leu Glu
    610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 15
<211> LENGTH: 976
<212> TYPE: PRT
<213> ORGANISM: Homo sapiens

<400> SEQUENCE: 15

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
```

```
                50                  55                  60
Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
                100                 105                 110

Asp Pro Ala Lys Leu Phe Leu Val Asp Arg Ser Leu Tyr Gly Lys Glu
                115                 120                 125

Asp Asn Asp Thr Leu Val Arg Cys Pro Leu Thr Asp Pro Glu Val Thr
                130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
                180                 185                 190

Lys Ser Val Leu Ser Glu Lys Phe Ile Leu Lys Val Arg Pro Ala Phe
                195                 200                 205

Lys Ala Val Pro Val Val Ser Val Ser Lys Ala Ser Tyr Leu Leu Arg
                210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
                260                 265                 270

Ala Thr Leu Thr Ile Ser Ser Ala Arg Val Asn Asp Ser Gly Val Phe
                275                 280                 285

Met Cys Tyr Ala Asn Asn Thr Phe Gly Ser Ala Asn Val Thr Thr Thr
                290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
                340                 345                 350

Arg Thr Phe Thr Asp Lys Trp Glu Asp Tyr Pro Lys Ser Glu Asn Glu
                355                 360                 365

Ser Asn Ile Arg Tyr Val Ser Glu Leu His Leu Thr Arg Leu Lys Gly
370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
                420                 425                 430

Phe Pro Glu Pro Thr Ile Asp Trp Tyr Phe Cys Pro Gly Thr Glu Gln
                435                 440                 445

Arg Cys Ser Ala Ser Val Leu Pro Val Asp Val Gln Thr Leu Asn Ser
                450                 455                 460

Ser Gly Pro Pro Phe Gly Lys Leu Val Val Gln Ser Ser Ile Asp Ser
465                 470                 475                 480
```

```
Ser Ala Phe Lys His Asn Gly Thr Val Glu Cys Lys Ala Tyr Asn Asp
            485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
            515                 520                 525

Phe Val Ile Val Ala Gly Met Met Cys Ile Ile Val Met Ile Leu Thr
            530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
            595                 600                 605

Tyr Gly Leu Ile Lys Ser Asp Ala Ala Met Thr Val Ala Val Lys Met
            610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
            690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
            755                 760                 765

Leu Leu Ser Phe Ser Tyr Gln Val Ala Lys Gly Met Ala Phe Leu Ala
770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895
```

```
Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
    930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 16
<211> LENGTH: 4544
<212> TYPE: PRT
<213> ORGANISM: Homo sapiens

<400> SEQUENCE: 16

Met Leu Thr Pro Pro Leu Leu Leu Leu Pro Leu Leu Ser Ala Leu
1               5                   10                  15

Val Ala Ala Ala Ile Asp Ala Pro Lys Thr Cys Ser Pro Lys Gln Phe
            20                  25                  30

Ala Cys Arg Asp Gln Ile Thr Cys Ile Ser Lys Gly Trp Arg Cys Asp
        35                  40                  45

Gly Glu Arg Asp Cys Pro Asp Gly Ser Asp Glu Ala Pro Glu Ile Cys
50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
            100                 105                 110

Gly Asn Cys Ser Arg Leu Gly Cys Gln His His Cys Val Pro Thr Leu
        115                 120                 125

Asp Gly Pro Thr Cys Tyr Cys Asn Ser Ser Phe Gln Leu Gln Ala Asp
    130                 135                 140

Gly Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
        195                 200                 205

Ile Leu Ala Thr Tyr Leu Ser Gly Ala Gln Val Ser Thr Ile Thr Pro
    210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
        275                 280                 285

Trp Leu Thr Gly Asn Phe Tyr Phe Val Asp Asp Ile Asp Arg Ile
    290                 295                 300
```

-continued

```
Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
            325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
            355                 360                 365

Pro His Gly Ile Thr Leu Asp Leu Val Ser Arg Leu Val Tyr Trp Ala
            370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
            405                 410                 415

Thr Val Phe Glu Asn Tyr Leu Tyr Ala Thr Asn Ser Asp Asn Ala Asn
            420                 425                 430

Ala Gln Gln Lys Thr Ser Val Ile Arg Val Asn Arg Phe Asn Ser Thr
            435                 440                 445

Glu Tyr Gln Val Val Thr Arg Val Asp Lys Gly Gly Ala Leu His Ile
450                 455                 460

Tyr His Gln Arg Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
            485                 490                 495

Asn Ser His Lys Ala Arg Thr Cys Arg Cys Arg Ser Gly Phe Ser Leu
            500                 505                 510

Gly Ser Asp Gly Lys Ser Cys Lys Lys Pro Glu His Glu Leu Phe Leu
            515                 520                 525

Val Tyr Gly Lys Gly Arg Pro Gly Ile Ile Arg Gly Met Asp Met Gly
            530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
            565                 570                 575

Asp Thr Thr Ser Tyr Leu Ile Gly Arg Gln Lys Ile Asp Gly Thr Glu
            580                 585                 590

Arg Glu Thr Ile Leu Lys Asp Gly Ile His Asn Val Glu Gly Val Ala
            595                 600                 605

Val Asp Trp Met Gly Asp Asn Leu Tyr Trp Thr Asp Asp Gly Pro Lys
            610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
            645                 650                 655

Pro Leu Asn Gly Trp Met Tyr Trp Thr Asp Trp Glu Glu Asp Pro Lys
            660                 665                 670

Asp Ser Arg Arg Gly Arg Leu Glu Arg Ala Trp Met Asp Gly Ser His
            675                 680                 685

Arg Asp Ile Phe Val Thr Ser Lys Thr Val Leu Trp Pro Asn Gly Leu
            690                 695                 700

Ser Leu Asp Ile Pro Ala Gly Arg Leu Tyr Trp Val Asp Ala Phe Tyr
705                 710                 715                 720
```

-continued

Asp Arg Ile Glu Thr Ile Leu Leu Asn Gly Thr Asp Arg Lys Ile Val
            725                 730                 735

Tyr Glu Gly Pro Glu Leu Asn His Ala Phe Gly Leu Cys His His Gly
        740                 745                 750

Asn Tyr Leu Phe Trp Thr Glu Tyr Arg Ser Gly Ser Val Tyr Arg Leu
        755                 760                 765

Glu Arg Gly Val Gly Gly Ala Pro Pro Thr Val Thr Leu Leu Arg Ser
    770                 775                 780

Glu Arg Pro Pro Ile Phe Glu Ile Arg Met Tyr Asp Ala Gln Gln Gln
785                 790                 795                 800

Gln Val Gly Thr Asn Lys Cys Arg Val Asn Asn Gly Gly Cys Ser Ser
                805                 810                 815

Leu Cys Leu Ala Thr Pro Gly Ser Arg Gln Cys Ala Cys Ala Glu Asp
            820                 825                 830

Gln Val Leu Asp Ala Asp Gly Val Thr Cys Leu Ala Asn Pro Ser Tyr
        835                 840                 845

Val Pro Pro Pro Gln Cys Gln Pro Gly Glu Phe Ala Cys Ala Asn Ser
    850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
                885                 890                 895

Ser Asp Arg Phe Lys Cys Glu Asn Asn Arg Cys Ile Pro Asn Arg Trp
            900                 905                 910

Leu Cys Asp Gly Asp Asn Asp Cys Gly Asn Ser Glu Asp Glu Ser Asn
        915                 920                 925

Ala Thr Cys Ser Ala Arg Thr Cys Pro Pro Asn Gln Phe Ser Cys Ala
    930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
                965                 970                 975

Phe Pro Leu Thr Gln Phe Thr Cys Asn Asn Gly Arg Cys Ile Asn Ile
            980                 985                 990

Asn Trp Arg Cys Asp Asn Asp Asn  Asp Cys Gly Asp Asn  Ser Asp Glu
        995                 1000                    1005

Ala Gly  Cys Ser His Ser Cys  Ser Ser Thr Gln Phe  Lys Cys Asn
    1010                    1015                    1020

Ser Gly  Arg Cys Ile Pro Glu  His Trp Thr Cys Asp  Gly Asp Asn
    1025                    1030                    1035

Asp Cys  Gly Asp Tyr Ser Asp  Glu Thr His Ala Asn  Cys Thr Asn
    1040                    1045                    1050

Gln Ala  Thr Arg Pro Pro Gly  Gly Cys His Thr Asp  Glu Phe Gln
    1055                    1060                    1065

Cys Arg  Leu Asp Gly Leu Cys  Ile Pro Leu Arg Trp  Arg Cys Asp
    1070                    1075                    1080

Gly Asp  Thr Asp Cys Met Asp  Ser Ser Asp Glu Lys  Ser Cys Glu
    1085                    1090                    1095

Gly Val  Thr His Val Cys Asp  Pro Ser Val Lys Phe  Gly Cys Lys
    1100                    1105                    1110

Asp Ser  Ala Arg Cys Ile Ser  Lys Ala Trp Val Cys  Asp Gly Asp
    1115                    1120                    1125

Asn Asp  Cys Glu Asp Asn Ser  Asp Glu Glu Asn Cys  Glu Ser Leu

```
              1130                1135                1140

Ala Cys Arg Pro Pro Ser His Pro Cys Ala Asn Asn Thr Ser Val
              1145                1150                1155

Cys Leu Pro Pro Asp Lys Leu Cys Asp Gly Asn Asp Asp Cys Gly
              1160                1165                1170

Asp Gly Ser Asp Glu Gly Glu Leu Cys Asp Gln Cys Ser Leu Asn
              1175                1180                1185

Asn Gly Gly Cys Ser His Asn Cys Ser Val Ala Pro Gly Glu Gly
              1190                1195                1200

Ile Val Cys Ser Cys Pro Leu Gly Met Glu Leu Gly Pro Asp Asn
              1205                1210                1215

His Thr Cys Gln Ile Gln Ser Tyr Cys Ala Lys His Leu Lys Cys
              1220                1225                1230

Ser Gln Lys Cys Asp Gln Asn Lys Phe Ser Val Lys Cys Ser Cys
              1235                1240                1245

Tyr Glu Gly Trp Val Leu Glu Pro Asp Gly Glu Ser Cys Arg Ser
              1250                1255                1260

Leu Asp Pro Phe Lys Pro Phe Ile Ile Phe Ser Asn Arg His Glu
              1265                1270                1275

Ile Arg Arg Ile Asp Leu His Lys Gly Asp Tyr Ser Val Leu Val
              1280                1285                1290

Pro Gly Leu Arg Asn Thr Ile Ala Leu Asp Phe His Leu Ser Gln
              1295                1300                1305

Ser Ala Leu Tyr Trp Thr Asp Val Val Glu Asp Lys Ile Tyr Arg
              1310                1315                1320

Gly Lys Leu Leu Asp Asn Gly Ala Leu Thr Ser Phe Glu Val Val
              1325                1330                1335

Ile Gln Tyr Gly Leu Ala Thr Pro Glu Gly Leu Ala Val Asp Trp
              1340                1345                1350

Ile Ala Gly Asn Ile Tyr Trp Val Glu Ser Asn Leu Asp Gln Ile
              1355                1360                1365

Glu Val Ala Lys Leu Asp Gly Thr Leu Arg Thr Thr Leu Leu Ala
              1370                1375                1380

Gly Asp Ile Glu His Pro Arg Ala Ile Ala Leu Asp Pro Arg Asp
              1385                1390                1395

Gly Ile Leu Phe Trp Thr Asp Trp Asp Ala Ser Leu Pro Arg Ile
              1400                1405                1410

Glu Ala Ala Ser Met Ser Gly Ala Gly Arg Arg Thr Val His Arg
              1415                1420                1425

Glu Thr Gly Ser Gly Gly Trp Pro Asn Gly Leu Thr Val Asp Tyr
              1430                1435                1440

Leu Glu Lys Arg Ile Leu Trp Ile Asp Ala Arg Ser Asp Ala Ile
              1445                1450                1455

Tyr Ser Ala Arg Tyr Asp Gly Ser Gly His Met Glu Val Leu Arg
              1460                1465                1470

Gly His Glu Phe Leu Ser His Pro Phe Ala Val Thr Leu Tyr Gly
              1475                1480                1485

Gly Glu Val Tyr Trp Thr Asp Trp Arg Thr Asn Thr Leu Ala Lys
              1490                1495                1500

Ala Asn Lys Trp Thr Gly His Asn Val Thr Val Val Gln Arg Thr
              1505                1510                1515

Asn Thr Gln Pro Phe Asp Leu Gln Val Tyr His Pro Ser Arg Gln
              1520                1525                1530
```

-continued

Pro Met Ala Pro Asn Pro Cys Glu Ala Asn Gly Gly Gln Gly Pro
    1535            1540                1545

Cys Ser His Leu Cys Leu Ile Asn Tyr Asn Arg Thr Val Ser Cys
    1550            1555                1560

Ala Cys Pro His Leu Met Lys Leu His Lys Asp Asn Thr Thr Cys
    1565            1570                1575

Tyr Glu Phe Lys Lys Phe Leu Leu Tyr Ala Arg Gln Met Glu Ile
    1580            1585                1590

Arg Gly Val Asp Leu Asp Ala Pro Tyr Tyr Asn Tyr Ile Ile Ser
    1595            1600                1605

Phe Thr Val Pro Asp Ile Asp Asn Val Thr Val Leu Asp Tyr Asp
    1610            1615                1620

Ala Arg Glu Gln Arg Val Tyr Trp Ser Asp Val Arg Thr Gln Ala
    1625            1630                1635

Ile Lys Arg Ala Phe Ile Asn Gly Thr Gly Val Glu Thr Val Val
    1640            1645                1650

Ser Ala Asp Leu Pro Asn Ala His Gly Leu Ala Val Asp Trp Val
    1655            1660                1665

Ser Arg Asn Leu Phe Trp Thr Ser Tyr Asp Thr Asn Lys Lys Gln
    1670            1675                1680

Ile Asn Val Ala Arg Leu Asp Gly Ser Phe Lys Asn Ala Val Val
    1685            1690                1695

Gln Gly Leu Glu Gln Pro His Gly Leu Val Val His Pro Leu Arg
    1700            1705                1710

Gly Lys Leu Tyr Trp Thr Asp Gly Asp Asn Ile Ser Met Ala Asn
    1715            1720                1725

Met Asp Gly Ser Asn Arg Thr Leu Leu Phe Ser Gly Gln Lys Gly
    1730            1735                1740

Pro Val Gly Leu Ala Ile Asp Phe Pro Glu Ser Lys Leu Tyr Trp
    1745            1750                1755

Ile Ser Ser Gly Asn His Thr Ile Asn Arg Cys Asn Leu Asp Gly
    1760            1765                1770

Ser Gly Leu Glu Val Ile Asp Ala Met Arg Ser Gln Leu Gly Lys
    1775            1780                1785

Ala Thr Ala Leu Ala Ile Met Gly Asp Lys Leu Trp Trp Ala Asp
    1790            1795                1800

Gln Val Ser Glu Lys Met Gly Thr Cys Ser Lys Ala Asp Gly Ser
    1805            1810                1815

Gly Ser Val Val Leu Arg Asn Ser Thr Thr Leu Val Met His Met
    1820            1825                1830

Lys Val Tyr Asp Glu Ser Ile Gln Leu Asp His Lys Gly Thr Asn
    1835            1840                1845

Pro Cys Ser Val Asn Asn Gly Asp Cys Ser Gln Leu Cys Leu Pro
    1850            1855                1860

Thr Ser Glu Thr Thr Arg Ser Cys Met Cys Thr Ala Gly Tyr Ser
    1865            1870                1875

Leu Arg Ser Gly Gln Gln Ala Cys Glu Gly Val Gly Ser Phe Leu
    1880            1885                1890

Leu Tyr Ser Val His Glu Gly Ile Arg Gly Ile Pro Leu Asp Pro
    1895            1900                1905

Asn Asp Lys Ser Asp Ala Leu Val Pro Val Ser Gly Thr Ser Leu
    1910            1915                1920

Ala Val Gly Ile Asp Phe His Ala Glu Asn Asp Thr Ile Tyr Trp
1925                1930                1935

Val Asp Met Gly Leu Ser Thr Ile Ser Arg Ala Lys Arg Asp Gln
1940                1945                1950

Thr Trp Arg Glu Asp Val Val Thr Asn Gly Ile Gly Arg Val Glu
1955                1960                1965

Gly Ile Ala Val Asp Trp Ile Ala Gly Asn Ile Tyr Trp Thr Asp
1970                1975                1980

Gln Gly Phe Asp Val Ile Glu Val Ala Arg Leu Asn Gly Ser Phe
1985                1990                1995

Arg Tyr Val Val Ile Ser Gln Gly Leu Asp Lys Pro Arg Ala Ile
2000                2005                2010

Thr Val His Pro Glu Lys Gly Tyr Leu Phe Trp Thr Glu Trp Gly
2015                2020                2025

Gln Tyr Pro Arg Ile Glu Arg Ser Arg Leu Asp Gly Thr Glu Arg
2030                2035                2040

Val Val Leu Val Asn Val Ser Ile Ser Trp Pro Asn Gly Ile Ser
2045                2050                2055

Val Asp Tyr Gln Asp Gly Lys Leu Tyr Trp Cys Asp Ala Arg Thr
2060                2065                2070

Asp Lys Ile Glu Arg Ile Asp Leu Glu Thr Gly Glu Asn Arg Glu
2075                2080                2085

Val Val Leu Ser Ser Asn Asn Met Asp Met Phe Ser Val Ser Val
2090                2095                2100

Phe Glu Asp Phe Ile Tyr Trp Ser Asp Arg Thr His Ala Asn Gly
2105                2110                2115

Ser Ile Lys Arg Gly Ser Lys Asp Asn Ala Thr Asp Ser Val Pro
2120                2125                2130

Leu Arg Thr Gly Ile Gly Val Gln Leu Lys Asp Ile Lys Val Phe
2135                2140                2145

Asn Arg Asp Arg Gln Lys Gly Thr Asn Val Cys Ala Val Ala Asn
2150                2155                2160

Gly Gly Cys Gln Gln Leu Cys Leu Tyr Arg Gly Arg Gly Gln Arg
2165                2170                2175

Ala Cys Ala Cys Ala His Gly Met Leu Ala Glu Asp Gly Ala Ser
2180                2185                2190

Cys Arg Glu Tyr Ala Gly Tyr Leu Leu Tyr Ser Glu Arg Thr Ile
2195                2200                2205

Leu Lys Ser Ile His Leu Ser Asp Glu Arg Asn Leu Asn Ala Pro
2210                2215                2220

Val Gln Pro Phe Glu Asp Pro Glu His Met Lys Asn Val Ile Ala
2225                2230                2235

Leu Ala Phe Asp Tyr Arg Ala Gly Thr Ser Pro Gly Thr Pro Asn
2240                2245                2250

Arg Ile Phe Phe Ser Asp Ile His Phe Gly Asn Ile Gln Gln Ile
2255                2260                2265

Asn Asp Asp Gly Ser Arg Arg Ile Thr Ile Val Glu Asn Val Gly
2270                2275                2280

Ser Val Glu Gly Leu Ala Tyr His Arg Gly Trp Asp Thr Leu Tyr
2285                2290                2295

Trp Thr Ser Tyr Thr Thr Ser Thr Ile Thr Arg His Thr Val Asp
2300                2305                2310

Gln Thr Arg Pro Gly Ala Phe Glu Arg Glu Thr Val Ile Thr Met

```
                    2315                2320                2325

Ser Gly Asp Asp His Pro Arg Ala Phe Val Leu Asp Glu Cys Gln
    2330                2335                2340

Asn Leu Met Phe Trp Thr Asn Trp Asn Glu Gln His Pro Ser Ile
    2345                2350                2355

Met Arg Ala Ala Leu Ser Gly Ala Asn Val Leu Thr Leu Ile Glu
    2360                2365                2370

Lys Asp Ile Arg Thr Pro Asn Gly Leu Ala Ile Asp His Arg Ala
    2375                2380                2385

Glu Lys Leu Tyr Phe Ser Asp Ala Thr Leu Asp Lys Ile Glu Arg
    2390                2395                2400

Cys Glu Tyr Asp Gly Ser His Arg Tyr Val Ile Leu Lys Ser Glu
    2405                2410                2415

Pro Val His Pro Phe Gly Leu Ala Val Tyr Gly Glu His Ile Phe
    2420                2425                2430

Trp Thr Asp Trp Val Arg Arg Ala Val Gln Arg Ala Asn Lys His
    2435                2440                2445

Val Gly Ser Asn Met Lys Leu Leu Arg Val Asp Ile Pro Gln Gln
    2450                2455                2460

Pro Met Gly Ile Ile Ala Val Ala Asn Asp Thr Asn Ser Cys Glu
    2465                2470                2475

Leu Ser Pro Cys Arg Ile Asn Asn Gly Gly Cys Gln Asp Leu Cys
    2480                2485                2490

Leu Leu Thr His Gln Gly His Val Asn Cys Ser Cys Arg Gly Gly
    2495                2500                2505

Arg Ile Leu Gln Asp Asp Leu Thr Cys Arg Ala Val Asn Ser Ser
    2510                2515                2520

Cys Arg Ala Gln Asp Glu Phe Glu Cys Ala Asn Gly Glu Cys Ile
    2525                2530                2535

Asn Phe Ser Leu Thr Cys Asp Gly Val Pro His Cys Lys Asp Lys
    2540                2545                2550

Ser Asp Glu Lys Pro Ser Tyr Cys Asn Ser Arg Arg Cys Lys Lys
    2555                2560                2565

Thr Phe Arg Gln Cys Ser Asn Gly Arg Cys Val Ser Asn Met Leu
    2570                2575                2580

Trp Cys Asn Gly Ala Asp Asp Cys Gly Asp Gly Ser Asp Glu Ile
    2585                2590                2595

Pro Cys Asn Lys Thr Ala Cys Gly Val Gly Glu Phe Arg Cys Arg
    2600                2605                2610

Asp Gly Thr Cys Ile Gly Asn Ser Ser Arg Cys Asn Gln Phe Val
    2615                2620                2625

Asp Cys Glu Asp Ala Ser Asp Glu Met Asn Cys Ser Ala Thr Asp
    2630                2635                2640

Cys Ser Ser Tyr Phe Arg Leu Gly Val Lys Gly Val Leu Phe Gln
    2645                2650                2655

Pro Cys Glu Arg Thr Ser Leu Cys Tyr Ala Pro Ser Trp Val Cys
    2660                2665                2670

Asp Gly Ala Asn Asp Cys Gly Asp Tyr Ser Asp Glu Arg Asp Cys
    2675                2680                2685

Pro Gly Val Lys Arg Pro Arg Cys Pro Leu Asn Tyr Phe Ala Cys
    2690                2695                2700

Pro Ser Gly Arg Cys Ile Pro Met Ser Trp Thr Cys Asp Lys Glu
    2705                2710                2715
```

```
Asp Asp Cys Glu His Gly Glu Asp Glu Thr His Cys Asn Lys Phe
    2720            2725            2730

Cys Ser Glu Ala Gln Phe Glu Cys Gln Asn His Arg Cys Ile Ser
    2735            2740            2745

Lys Gln Trp Leu Cys Asp Gly Ser Asp Asp Cys Gly Asp Gly Ser
    2750            2755            2760

Asp Glu Ala Ala His Cys Glu Gly Lys Thr Cys Gly Pro Ser Ser
    2765            2770            2775

Phe Ser Cys Pro Gly Thr His Val Cys Val Pro Glu Arg Trp Leu
    2780            2785            2790

Cys Asp Gly Asp Lys Asp Cys Ala Asp Gly Ala Asp Glu Ser Ile
    2795            2800            2805

Ala Ala Gly Cys Leu Tyr Asn Ser Thr Cys Asp Asp Arg Glu Phe
    2810            2815            2820

Met Cys Gln Asn Arg Gln Cys Ile Pro Lys His Phe Val Cys Asp
    2825            2830            2835

His Asp Arg Asp Cys Ala Asp Gly Ser Asp Glu Ser Pro Glu Cys
    2840            2845            2850

Glu Tyr Pro Thr Cys Gly Pro Ser Glu Phe Arg Cys Ala Asn Gly
    2855            2860            2865

Arg Cys Leu Ser Ser Arg Gln Trp Glu Cys Asp Gly Glu Asn Asp
    2870            2875            2880

Cys His Asp Gln Ser Asp Glu Ala Pro Lys Asn Pro His Cys Thr
    2885            2890            2895

Ser Gln Glu His Lys Cys Asn Ala Ser Ser Gln Phe Leu Cys Ser
    2900            2905            2910

Ser Gly Arg Cys Val Ala Glu Ala Leu Leu Cys Asn Gly Gln Asp
    2915            2920            2925

Asp Cys Gly Asp Ser Ser Asp Glu Arg Gly Cys His Ile Asn Glu
    2930            2935            2940

Cys Leu Ser Arg Lys Leu Ser Gly Cys Ser Gln Asp Cys Glu Asp
    2945            2950            2955

Leu Lys Ile Gly Phe Lys Cys Arg Cys Arg Pro Gly Phe Arg Leu
    2960            2965            2970

Lys Asp Asp Gly Arg Thr Cys Ala Asp Val Asp Glu Cys Ser Thr
    2975            2980            2985

Thr Phe Pro Cys Ser Gln Arg Cys Ile Asn Thr His Gly Ser Tyr
    2990            2995            3000

Lys Cys Leu Cys Val Glu Gly Tyr Ala Pro Arg Gly Gly Asp Pro
    3005            3010            3015

His Ser Cys Lys Ala Val Thr Asp Glu Glu Pro Phe Leu Ile Phe
    3020            3025            3030

Ala Asn Arg Tyr Tyr Leu Arg Lys Leu Asn Leu Asp Gly Ser Asn
    3035            3040            3045

Tyr Thr Leu Leu Lys Gln Gly Leu Asn Asn Ala Val Ala Leu Asp
    3050            3055            3060

Phe Asp Tyr Arg Glu Gln Met Ile Tyr Trp Thr Asp Val Thr Thr
    3065            3070            3075

Gln Gly Ser Met Ile Arg Arg Met His Leu Asn Gly Ser Asn Val
    3080            3085            3090

Gln Val Leu His Arg Thr Gly Leu Ser Asn Pro Asp Gly Leu Ala
    3095            3100            3105
```

-continued

```
Val Asp Trp Val Gly Gly Asn Leu Tyr Trp Cys Asp Lys Gly Arg
3110            3115                3120
Asp Thr Ile Glu Val Ser Lys Leu Asn Gly Ala Tyr Arg Thr Val
3125            3130                3135
Leu Val Ser Ser Gly Leu Arg Glu Pro Arg Ala Leu Val Val Asp
3140            3145                3150
Val Gln Asn Gly Tyr Leu Tyr Trp Thr Asp Trp Gly Asp His Ser
3155            3160                3165
Leu Ile Gly Arg Ile Gly Met Asp Gly Ser Ser Arg Ser Val Ile
3170            3175                3180
Val Asp Thr Lys Ile Thr Trp Pro Asn Gly Leu Thr Leu Asp Tyr
3185            3190                3195
Val Thr Glu Arg Ile Tyr Trp Ala Asp Ala Arg Glu Asp Tyr Ile
3200            3205                3210
Glu Phe Ala Ser Leu Asp Gly Ser Asn Arg His Val Val Leu Ser
3215            3220                3225
Gln Asp Ile Pro His Ile Phe Ala Leu Thr Leu Phe Glu Asp Tyr
3230            3235                3240
Val Tyr Trp Thr Asp Trp Glu Thr Lys Ser Ile Asn Arg Ala His
3245            3250                3255
Lys Thr Thr Gly Thr Asn Lys Thr Leu Leu Ile Ser Thr Leu His
3260            3265                3270
Arg Pro Met Asp Leu His Val Phe His Ala Leu Arg Gln Pro Asp
3275            3280                3285
Val Pro Asn His Pro Cys Lys Val Asn Asn Gly Gly Cys Ser Asn
3290            3295                3300
Leu Cys Leu Leu Ser Pro Gly Gly Gly His Lys Cys Ala Cys Pro
3305            3310                3315
Thr Asn Phe Tyr Leu Gly Ser Asp Gly Arg Thr Cys Val Ser Asn
3320            3325                3330
Cys Thr Ala Ser Gln Phe Val Cys Lys Asn Asp Lys Cys Ile Pro
3335            3340                3345
Phe Trp Trp Lys Cys Asp Thr Glu Asp Asp Cys Gly Asp His Ser
3350            3355                3360
Asp Glu Pro Pro Asp Cys Pro Glu Phe Lys Cys Arg Pro Gly Gln
3365            3370                3375
Phe Gln Cys Ser Thr Gly Ile Cys Thr Asn Pro Ala Phe Ile Cys
3380            3385                3390
Asp Gly Asp Asn Asp Cys Gln Asp Asn Ser Asp Glu Ala Asn Cys
3395            3400                3405
Asp Ile His Val Cys Leu Pro Ser Gln Phe Lys Cys Thr Asn Thr
3410            3415                3420
Asn Arg Cys Ile Pro Gly Ile Phe Arg Cys Asn Gly Gln Asp Asn
3425            3430                3435
Cys Gly Asp Gly Glu Asp Glu Arg Asp Cys Pro Glu Val Thr Cys
3440            3445                3450
Ala Pro Asn Gln Phe Gln Cys Ser Ile Thr Lys Arg Cys Ile Pro
3455            3460                3465
Arg Val Trp Val Cys Asp Arg Asp Asn Asp Cys Val Asp Gly Ser
3470            3475                3480
Asp Glu Pro Ala Asn Cys Thr Gln Met Thr Cys Gly Val Asp Glu
3485            3490                3495
Phe Arg Cys Lys Asp Ser Gly Arg Cys Ile Pro Ala Arg Trp Lys
```

-continued

|  |  |  |  |  |  |  |  |  |  |  |  |
|---|---|---|---|---|---|---|---|---|---|---|---|
|  |  | 3500 |  |  |  | 3505 |  |  |  | 3510 |  |
| Cys | Asp<br>3515 | Gly | Glu | Asp | Asp<br>3520 | Cys | Gly | Asp | Gly<br>3525 | Ser | Asp | Glu | Pro | Lys |
| Glu | Glu<br>3530 | Cys | Asp | Glu | Arg<br>3535 | Thr | Cys | Glu | Pro<br>3540 | Tyr | Gln | Phe | Arg | Cys |
| Lys | Asn<br>3545 | Asn | Arg | Cys | Val<br>3550 | Pro | Gly | Arg | Trp<br>3555 | Gln | Cys | Asp | Tyr | Asp |
| Asn | Asp<br>3560 | Cys | Gly | Asp | Asn<br>3565 | Ser | Asp | Glu | Glu<br>3570 | Ser | Cys | Thr | Pro | Arg |
| Pro | Cys<br>3575 | Ser | Glu | Ser | Glu<br>3580 | Phe | Ser | Cys | Ala<br>3585 | Asn | Gly | Arg | Cys | Ile |
| Ala | Gly<br>3590 | Arg | Trp | Lys | Cys<br>3595 | Asp | Gly | Asp | His<br>3600 | Asp | Cys | Ala | Asp | Gly |
| Ser | Asp<br>3605 | Glu | Lys | Asp | Cys<br>3610 | Thr | Pro | Arg | Cys<br>3615 | Asp | Met | Asp | Gln | Phe |
| Gln | Cys<br>3620 | Lys | Ser | Gly | His<br>3625 | Cys | Ile | Pro | Leu<br>3630 | Arg | Trp | Arg | Cys | Asp |
| Ala | Asp<br>3635 | Ala | Asp | Cys | Met<br>3640 | Asp | Gly | Ser | Asp<br>3645 | Glu | Glu | Ala | Cys | Gly |
| Thr | Gly<br>3650 | Val | Arg | Thr | Cys<br>3655 | Pro | Leu | Asp | Glu<br>3660 | Phe | Gln | Cys | Asn | Asn |
| Thr | Leu<br>3665 | Cys | Lys | Pro | Leu<br>3670 | Ala | Trp | Lys | Cys<br>3675 | Asp | Gly | Glu | Asp | Asp |
| Cys | Gly<br>3680 | Asp | Asn | Ser | Asp<br>3685 | Glu | Asn | Pro | Glu<br>3690 | Glu | Cys | Ala | Arg | Phe |
| Val | Cys<br>3695 | Pro | Pro | Asn | Arg<br>3700 | Pro | Phe | Arg | Cys<br>3705 | Lys | Asn | Asp | Arg | Val |
| Cys | Leu<br>3710 | Trp | Ile | Gly | Arg<br>3715 | Gln | Cys | Asp | Gly<br>3720 | Thr | Asp | Asn | Cys | Gly |
| Asp | Gly<br>3725 | Thr | Asp | Glu | Glu<br>3730 | Asp | Cys | Glu | Pro<br>3735 | Pro | Thr | Ala | His | Thr |
| Thr | His<br>3740 | Cys | Lys | Asp | Lys<br>3745 | Lys | Glu | Phe | Leu<br>3750 | Cys | Arg | Asn | Gln | Arg |
| Cys | Leu<br>3755 | Ser | Ser | Ser | Leu<br>3760 | Arg | Cys | Asn | Met<br>3765 | Phe | Asp | Asp | Cys | Gly |
| Asp | Gly<br>3770 | Ser | Asp | Glu | Glu<br>3775 | Asp | Cys | Ser | Ile<br>3780 | Asp | Pro | Lys | Leu | Thr |
| Ser | Cys<br>3785 | Ala | Thr | Asn | Ala<br>3790 | Ser | Ile | Cys | Gly<br>3795 | Asp | Glu | Ala | Arg | Cys |
| Val | Arg<br>3800 | Thr | Glu | Lys | Ala<br>3805 | Ala | Tyr | Cys | Ala<br>3810 | Cys | Arg | Ser | Gly | Phe |
| His | Thr<br>3815 | Val | Pro | Gly | Gln<br>3820 | Pro | Gly | Cys | Gln<br>3825 | Asp | Ile | Asn | Glu | Cys |
| Leu | Arg<br>3830 | Phe | Gly | Thr | Cys<br>3835 | Ser | Gln | Leu | Cys<br>3840 | Asn | Asn | Thr | Lys | Gly |
| Gly | His<br>3845 | Leu | Cys | Ser | Cys<br>3850 | Ala | Arg | Asn | Phe<br>3855 | Met | Lys | Thr | His | Asn |
| Thr | Cys<br>3860 | Lys | Ala | Glu | Gly<br>3865 | Ser | Glu | Tyr | Gln<br>3870 | Val | Leu | Tyr | Ile | Ala |
| Asp | Asp<br>3875 | Asn | Glu | Ile | Arg<br>3880 | Ser | Leu | Phe | Pro<br>3885 | Gly | His | Pro | His | Ser |
| Ala | Tyr<br>3890 | Glu | Gln | Ala | Phe<br>3895 | Gln | Gly | Asp | Glu<br>3900 | Ser | Val | Arg | Ile | Asp |

-continued

```
Ala Met Asp Val His Val Lys Ala Gly Arg Val Tyr Trp Thr Asn
    3905            3910                3915
Trp His Thr Gly Thr Ile Ser Tyr Arg Ser Leu Pro Pro Ala Ala
    3920            3925                3930
Pro Pro Thr Thr Ser Asn Arg His Arg Arg Gln Ile Asp Arg Gly
    3935            3940                3945
Val Thr His Leu Asn Ile Ser Gly Leu Lys Met Pro Arg Gly Ile
    3950            3955                3960
Ala Ile Asp Trp Val Ala Gly Asn Val Tyr Trp Thr Asp Ser Gly
    3965            3970                3975
Arg Asp Val Ile Glu Val Ala Gln Met Lys Gly Glu Asn Arg Lys
    3980            3985                3990
Thr Leu Ile Ser Gly Met Ile Asp Glu Pro His Ala Ile Val Val
    3995            4000                4005
Asp Pro Leu Arg Gly Thr Met Tyr Trp Ser Asp Trp Gly Asn His
    4010            4015                4020
Pro Lys Ile Glu Thr Ala Ala Met Asp Gly Thr Leu Arg Glu Thr
    4025            4030                4035
Leu Val Gln Asp Asn Ile Gln Trp Pro Thr Gly Leu Ala Val Asp
    4040            4045                4050
Tyr His Asn Glu Arg Leu Tyr Trp Ala Asp Ala Lys Leu Ser Val
    4055            4060                4065
Ile Gly Ser Ile Arg Leu Asn Gly Thr Asp Pro Ile Val Ala Ala
    4070            4075                4080
Asp Ser Lys Arg Gly Leu Ser His Pro Phe Ser Ile Asp Val Phe
    4085            4090                4095
Glu Asp Tyr Ile Tyr Gly Val Thr Tyr Ile Asn Asn Arg Val Phe
    4100            4105                4110
Lys Ile His Lys Phe Gly His Ser Pro Leu Val Asn Leu Thr Gly
    4115            4120                4125
Gly Leu Ser His Ala Ser Asp Val Val Leu Tyr His Gln His Lys
    4130            4135                4140
Gln Pro Glu Val Thr Asn Pro Cys Asp Arg Lys Lys Cys Glu Trp
    4145            4150                4155
Leu Cys Leu Leu Ser Pro Ser Gly Pro Val Cys Thr Cys Pro Asn
    4160            4165                4170
Gly Lys Arg Leu Asp Asn Gly Thr Cys Val Pro Val Pro Ser Pro
    4175            4180                4185
Thr Pro Pro Pro Asp Ala Pro Arg Pro Gly Thr Cys Asn Leu Gln
    4190            4195                4200
Cys Phe Asn Gly Gly Ser Cys Phe Leu Asn Ala Arg Arg Gln Pro
    4205            4210                4215
Lys Cys Arg Cys Gln Pro Arg Tyr Thr Gly Asp Lys Cys Glu Leu
    4220            4225                4230
Asp Gln Cys Trp Glu His Cys Arg Asn Gly Gly Thr Cys Ala Ala
    4235            4240                4245
Ser Pro Ser Gly Met Pro Thr Cys Arg Cys Pro Thr Gly Phe Thr
    4250            4255                4260
Gly Pro Lys Cys Thr Gln Gln Val Cys Ala Gly Tyr Cys Ala Asn
    4265            4270                4275
Asn Ser Thr Cys Thr Val Asn Gln Gly Asn Gln Pro Gln Cys Arg
    4280            4285                4290
```

-continued

```
Cys Leu Pro Gly Phe Leu Gly Asp Arg Cys Gln Tyr Arg Gln Cys
    4295                4300                4305

Ser Gly Tyr Cys Glu Asn Phe Gly Thr Cys Gln Met Ala Ala Asp
    4310                4315                4320

Gly Ser Arg Gln Cys Arg Cys Thr Ala Tyr Phe Glu Gly Ser Arg
    4325                4330                4335

Cys Glu Val Asn Lys Cys Ser Arg Cys Leu Glu Gly Ala Cys Val
    4340                4345                4350

Val Asn Lys Gln Ser Gly Asp Val Thr Cys Asn Cys Thr Asp Gly
    4355                4360                4365

Arg Val Ala Pro Ser Cys Leu Thr Cys Val Gly His Cys Ser Asn
    4370                4375                4380

Gly Gly Ser Cys Thr Met Asn Ser Lys Met Met Pro Glu Cys Gln
    4385                4390                4395

Cys Pro Pro His Met Thr Gly Pro Arg Cys Glu Glu His Val Phe
    4400                4405                4410

Ser Gln Gln Gln Pro Gly His Ile Ala Ser Ile Leu Ile Pro Leu
    4415                4420                4425

Leu Leu Leu Leu Leu Leu Val Leu Val Ala Gly Val Val Phe Trp
    4430                4435                4440

Tyr Lys Arg Arg Val Gln Gly Ala Lys Gly Phe Gln His Gln Arg
    4445                4450                4455

Met Thr Asn Gly Ala Met Asn Val Glu Ile Gly Asn Pro Thr Tyr
    4460                4465                4470

Lys Met Tyr Glu Gly Gly Glu Pro Asp Asp Val Gly Gly Leu Leu
    4475                4480                4485

Asp Ala Asp Phe Ala Leu Asp Pro Asp Lys Pro Thr Asn Phe Thr
    4490                4495                4500

Asn Pro Val Tyr Ala Thr Leu Tyr Met Gly Gly His Gly Ser Arg
    4505                4510                4515

His Ser Leu Ala Ser Thr Asp Glu Lys Arg Glu Leu Leu Gly Arg
    4520                4525                4530

Gly Pro Glu Asp Glu Ile Gly Asp Pro Leu Ala
    4535                4540

<210> SEQ ID NO 17
<211> LENGTH: 418
<212> TYPE: PRT
<213> ORGANISM: Homo sapiens

<400> SEQUENCE: 17

Met Gln Ala Leu Val Leu Leu Cys Ile Gly Ala Leu Leu Gly His
1               5                   10                  15

Ser Ser Cys Gln Asn Pro Ala Ser Pro Glu Glu Gly Ser Pro Asp
                20                  25                  30

Pro Asp Ser Thr Gly Ala Leu Val Glu Glu Asp Pro Phe Phe Lys
            35                  40                  45

Val Pro Val Asn Lys Leu Ala Ala Ala Val Ser Asn Phe Gly Tyr Asp
        50                  55                  60

Leu Tyr Arg Val Arg Ser Ser Thr Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
                100                 105                 110
```

```
Ile Ser Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 18
<211> LENGTH: 338
<212> TYPE: PRT
<213> ORGANISM: Homo sapiens

<400> SEQUENCE: 18

Met Ser Leu Ser Ala Phe Thr Leu Phe Leu Ala Leu Ile Gly Gly Thr
1               5                   10                  15

Ser Gly Gln Tyr Tyr Asp Tyr Asp Phe Pro Leu Ser Ile Tyr Gly Gln
                20                  25                  30

Ser Ser Pro Asn Cys Ala Pro Glu Cys Asn Cys Pro Glu Ser Tyr Pro
            35                  40                  45

Ser Ala Met Tyr Cys Asp Glu Leu Lys Leu Lys Ser Val Pro Met Val
        50                  55                  60
```

-continued

```
Pro Pro Gly Ile Lys Tyr Leu Tyr Leu Arg Asn Asn Gln Ile Asp His
65                  70                  75                  80

Ile Asp Glu Lys Ala Phe Glu Asn Val Thr Asp Leu Gln Trp Leu Ile
                85                  90                  95

Leu Asp His Asn Leu Leu Glu Asn Ser Lys Ile Lys Gly Arg Val Phe
            100                 105                 110

Ser Lys Leu Lys Gln Leu Lys Lys Leu His Ile Asn His Asn Asn Leu
        115                 120                 125

Thr Glu Ser Val Gly Pro Leu Pro Lys Ser Leu Glu Asp Leu Gln Leu
130                 135                 140

Thr His Asn Lys Ile Thr Lys Leu Gly Ser Phe Glu Gly Leu Val Asn
145                 150                 155                 160

Leu Thr Phe Ile His Leu Gln His Asn Arg Leu Lys Glu Asp Ala Val
                165                 170                 175

Ser Ala Ala Phe Lys Gly Leu Lys Ser Leu Glu Tyr Leu Asp Leu Ser
            180                 185                 190

Phe Asn Gln Ile Ala Arg Leu Pro Ser Gly Leu Pro Val Ser Leu Leu
        195                 200                 205

Thr Leu Tyr Leu Asp Asn Asn Lys Ile Ser Asn Ile Pro Asp Glu Tyr
210                 215                 220

Phe Lys Arg Phe Asn Ala Leu Gln Tyr Leu Arg Leu Ser His Asn Glu
225                 230                 235                 240

Leu Ala Asp Ser Gly Ile Pro Gly Asn Ser Phe Asn Val Ser Ser Leu
                245                 250                 255

Val Glu Leu Asp Leu Ser Tyr Asn Lys Leu Lys Asn Ile Pro Thr Val
            260                 265                 270

Asn Glu Asn Leu Glu Asn Tyr Tyr Leu Glu Val Asn Gln Leu Glu Lys
        275                 280                 285

Phe Asp Ile Lys Ser Phe Cys Lys Ile Leu Gly Pro Leu Ser Tyr Ser
290                 295                 300

Lys Ile Lys His Leu Arg Leu Asp Gly Asn Arg Ile Ser Glu Thr Ser
305                 310                 315                 320

Leu Pro Pro Asp Met Tyr Glu Cys Leu Arg Val Ala Asn Glu Val Thr
                325                 330                 335

Leu Asn
```

<210> SEQ ID NO 19
<211> LENGTH: 1156
<212> TYPE: PRT
<213> ORGANISM: Homo sapiens

<400> SEQUENCE: 19

```
Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
                20                  25                  30

Leu Leu Leu Ser Ala Cys Phe Val Thr Ser Ser Leu Gly Gly Thr Asp
            35                  40                  45

Lys Glu Leu Arg Leu Val Asp Gly Glu Asn Lys Cys Ser Gly Arg Val
        50                  55                  60

Glu Val Lys Val Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95
```

-continued

```
Ala Ile Lys Ala Pro Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Asn Phe Asn Ile Asp His
            180                 185                 190

Ala Ser Val Ile Cys Arg Gln Leu Glu Cys Gly Ser Ala Val Ser Phe
        195                 200                 205

Ser Gly Ser Ser Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser Tyr Asp Ala Ala Val Ala Cys
    290                 295                 300

Lys Gln Leu Gly Cys Pro Thr Ala Val Thr Ala Ile Gly Arg Val Asn
305                 310                 315                 320

Ala Ser Lys Gly Phe Gly His Ile Trp Leu Asp Ser Val Ser Cys Gln
                325                 330                 335

Gly His Glu Pro Ala Ile Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
            420                 425                 430

Thr Asn Thr Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Ile Cys Asp Ser Asp Phe Ser Leu Glu Ala Ala
            500                 505                 510
```

```
Ser Val Leu Cys Arg Glu Leu Gln Cys Gly Thr Val Ser Ile Leu
        515                 520                 525

Gly Gly Ala His Phe Gly Glu Gly Asn Gly Gln Ile Trp Ala Glu Glu
530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Gly Ala Trp Gly Ser Leu Cys
        595                 600                 605

Asn Ser His Trp Asp Ile Glu Asp Ala His Val Leu Cys Gln Gln Leu
    610                 615                 620

Lys Cys Gly Val Ala Leu Ser Thr Pro Gly Gly Ala Arg Phe Gly Lys
625                 630                 635                 640

Gly Asn Gly Gln Ile Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Glu Gln Val Ala Ser Val Ile Cys Ser Gly Asn Gln Ser Gln
        675                 680                 685

Thr Leu Ser Ser Cys Asn Ser Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Thr Val Gly Lys Ser Ser Met Ser Glu Thr Thr Val Gly Val Val Cys
    850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Ser Pro Ser Glu Glu Thr Trp Ile Thr Cys Asp Asn Lys
        915                 920                 925

Ile Arg Leu Gln Glu Gly Pro Thr Ser Cys Ser Gly Arg Val Glu Ile
```

```
                930              935                940
Trp His Gly Gly Ser Trp Gly Thr Val Cys Asp Asp Ser Trp Asp Leu
945                950                955                960

Asp Asp Ala Gln Val Val Cys Gln Gln Leu Gly Cys Gly Pro Ala Leu
            965                970                975

Lys Ala Phe Lys Glu Ala Glu Phe Gly Gln Gly Thr Gly Pro Ile Trp
            980                985                990

Leu Asn Glu Val Lys Cys Lys Gly Asn Glu Ser Ser Leu Trp Asp Cys
            995                1000               1005

Pro Ala Arg Arg Trp Gly His Ser Glu Cys Gly His Lys Glu Asp
    1010                1015                1020

Ala Ala Val Asn Cys Thr Asp Ile Ser Val Gln Lys Thr Pro Gln
    1025                1030                1035

Lys Ala Thr Thr Gly Arg Ser Ser Arg Gln Ser Ser Phe Ile Ala
    1040                1045                1050

Val Gly Ile Leu Gly Val Val Leu Leu Ala Ile Phe Val Ala Leu
    1055                1060                1065

Phe Phe Leu Thr Lys Lys Arg Arg Gln Arg Gln Arg Leu Ala Val
    1070                1075                1080

Ser Ser Arg Gly Glu Asn Leu Val His Gln Ile Gln Tyr Arg Glu
    1085                1090                1095

Met Asn Ser Cys Leu Asn Ala Asp Asp Leu Asp Leu Met Asn Ser
    1100                1105                1110

Ser Glu Asn Ser His Glu Ser Ala Asp Phe Ser Ala Ala Glu Leu
    1115                1120                1125

Ile Ser Val Ser Lys Phe Leu Pro Ile Ser Gly Met Glu Lys Glu
    1130                1135                1140

Ala Ile Leu Ser His Thr Glu Lys Glu Asn Gly Asn Leu
    1145                1150                1155

<210> SEQ ID NO 20
<211> LENGTH: 1337
<212> TYPE: PRT
<213> ORGANISM: Homo sapiens

<400> SEQUENCE: 20

Met Lys Pro Ala Ala Arg Glu Ala Arg Leu Pro Pro Arg Ser Pro Gly
1               5                   10                  15

Leu Arg Trp Ala Leu Pro Leu Leu Leu Leu Leu Arg Leu Gly Gln
                20                  25                  30

Ile Leu Cys Ala Gly Gly Thr Pro Ser Pro Ile Pro Asp Pro Ser Val
            35                  40                  45

Ala Thr Val Ala Thr Gly Glu Asn Gly Ile Thr Gln Ile Ser Ser Thr
50                  55                  60

Ala Glu Ser Phe His Lys Gln Asn Gly Thr Gly Thr Pro Gln Val Glu
65                  70                  75                  80

Thr Asn Thr Ser Glu Asp Gly Glu Ser Ser Gly Ala Asn Asp Ser Leu
                85                  90                  95

Arg Thr Pro Glu Gln Gly Ser Asn Gly Thr Asp Gly Ala Ser Gln Lys
            100                 105                 110

Thr Pro Ser Ser Thr Gly Pro Ser Pro Val Phe Asp Ile Lys Ala Val
        115                 120                 125

Ser Ile Ser Pro Thr Asn Val Ile Leu Thr Trp Lys Ser Asn Asp Thr
    130                 135                 140
```

-continued

```
Ala Ala Ser Glu Tyr Lys Tyr Val Val Lys His Lys Met Glu Asn Glu
145                 150                 155                 160

Lys Thr Ile Thr Val Val His Gln Pro Trp Cys Asn Ile Thr Gly Leu
            165                 170                 175

Arg Pro Ala Thr Ser Tyr Val Phe Ser Ile Thr Pro Gly Ile Gly Asn
        180                 185                 190

Glu Thr Trp Gly Asp Pro Arg Val Ile Lys Val Ile Thr Glu Pro Ile
    195                 200                 205

Pro Val Ser Asp Leu Arg Val Ala Leu Thr Gly Val Arg Lys Ala Ala
210                 215                 220

Leu Ser Trp Ser Asn Gly Asn Gly Thr Ala Ser Cys Arg Val Leu Leu
225                 230                 235                 240

Glu Ser Ile Gly Ser His Glu Glu Leu Thr Gln Asp Ser Arg Leu Gln
                245                 250                 255

Val Asn Ile Ser Gly Leu Lys Pro Gly Val Gln Tyr Asn Ile Asn Pro
            260                 265                 270

Tyr Leu Leu Gln Ser Asn Lys Thr Lys Gly Asp Pro Leu Gly Thr Glu
        275                 280                 285

Gly Gly Leu Asp Ala Ser Asn Thr Glu Arg Ser Arg Ala Gly Ser Pro
    290                 295                 300

Thr Ala Pro Val His Asp Glu Ser Leu Val Gly Pro Val Asp Pro Ser
305                 310                 315                 320

Ser Gly Gln Gln Ser Arg Asp Thr Glu Val Leu Leu Val Gly Leu Glu
                325                 330                 335

Pro Gly Thr Arg Tyr Asn Ala Thr Val Tyr Ser Gln Ala Ala Asn Gly
            340                 345                 350

Thr Glu Gly Gln Pro Gln Ala Ile Glu Phe Arg Thr Asn Ala Ile Gln
        355                 360                 365

Val Phe Asp Val Thr Ala Val Asn Ile Ser Ala Thr Ser Leu Thr Leu
    370                 375                 380

Ile Trp Lys Val Ser Asp Asn Glu Ser Ser Ser Asn Tyr Thr Tyr Lys
385                 390                 395                 400

Ile His Val Ala Gly Glu Thr Asp Ser Ser Asn Leu Asn Val Ser Glu
                405                 410                 415

Pro Arg Ala Val Ile Pro Gly Leu Arg Ser Ser Thr Phe Tyr Asn Ile
            420                 425                 430

Thr Val Cys Pro Val Leu Gly Asp Ile Glu Gly Thr Pro Gly Phe Leu
        435                 440                 445

Gln Val His Thr Pro Pro Val Pro Val Ser Asp Phe Arg Val Thr Val
    450                 455                 460

Val Ser Thr Thr Glu Ile Gly Leu Ala Trp Ser Ser His Asp Ala Glu
465                 470                 475                 480

Ser Phe Gln Met His Ile Thr Gln Glu Gly Ala Gly Asn Ser Arg Val
                485                 490                 495

Glu Ile Thr Thr Asn Gln Ser Ile Ile Gly Gly Leu Phe Pro Gly
            500                 505                 510

Thr Lys Tyr Cys Phe Glu Ile Val Pro Lys Gly Pro Asn Gly Thr Glu
        515                 520                 525

Gly Ala Ser Arg Thr Val Cys Asn Arg Thr Val Pro Ser Ala Val Phe
    530                 535                 540

Asp Ile His Val Val Tyr Val Thr Thr Thr Glu Met Trp Leu Asp Trp
545                 550                 555                 560

Lys Ser Pro Asp Gly Ala Ser Glu Tyr Val Tyr His Leu Val Ile Glu
```

```
                565                 570                 575
Ser Lys His Gly Ser Asn His Thr Ser Thr Tyr Asp Lys Ala Ile Thr
                580                 585                 590
Leu Gln Gly Leu Ile Pro Gly Thr Leu Tyr Asn Ile Thr Ile Ser Pro
                595                 600                 605
Glu Val Asp His Val Trp Gly Asp Pro Asn Ser Thr Ala Gln Tyr Thr
                610                 615                 620
Arg Pro Ser Asn Val Ser Asn Ile Asp Val Ser Thr Asn Thr Thr Ala
625                 630                 635                 640
Ala Thr Leu Ser Trp Gln Asn Phe Asp Asp Ala Ser Pro Thr Tyr Ser
                645                 650                 655
Tyr Cys Leu Leu Ile Glu Lys Ala Gly Asn Ser Ser Asn Ala Thr Gln
                660                 665                 670
Val Val Thr Asp Ile Gly Ile Thr Asp Ala Thr Val Thr Glu Leu Ile
                675                 680                 685
Pro Gly Ser Ser Tyr Thr Val Glu Ile Phe Ala Gln Val Gly Asp Gly
                690                 695                 700
Ile Lys Ser Leu Glu Pro Gly Arg Lys Ser Phe Cys Thr Asp Pro Ala
705                 710                 715                 720
Ser Met Ala Ser Phe Asp Cys Glu Val Val Pro Lys Glu Pro Ala Leu
                725                 730                 735
Val Leu Lys Trp Thr Cys Pro Pro Gly Ala Asn Ala Gly Phe Glu Leu
                740                 745                 750
Glu Val Ser Ser Gly Ala Trp Asn Asn Ala Thr His Leu Glu Ser Cys
                755                 760                 765
Ser Ser Glu Asn Gly Thr Glu Tyr Arg Thr Glu Val Thr Tyr Leu Asn
                770                 775                 780
Phe Ser Thr Ser Tyr Asn Ile Ser Ile Thr Thr Val Ser Cys Gly Lys
785                 790                 795                 800
Met Ala Ala Pro Thr Arg Asn Thr Cys Thr Thr Gly Ile Thr Asp Pro
                805                 810                 815
Pro Pro Pro Asp Gly Ser Pro Asn Ile Thr Ser Val Ser His Asn Ser
                820                 825                 830
Val Lys Val Lys Phe Ser Gly Phe Glu Ala Ser His Gly Pro Ile Lys
                835                 840                 845
Ala Tyr Ala Val Ile Leu Thr Thr Gly Glu Ala Gly His Pro Ser Ala
                850                 855                 860
Asp Val Leu Lys Tyr Thr Tyr Glu Asp Phe Lys Lys Gly Ala Ser Asp
865                 870                 875                 880
Thr Tyr Val Thr Tyr Leu Ile Arg Thr Glu Glu Lys Gly Arg Ser Gln
                885                 890                 895
Ser Leu Ser Glu Val Leu Lys Tyr Glu Ile Asp Val Gly Asn Glu Ser
                900                 905                 910
Thr Thr Leu Gly Tyr Tyr Asn Gly Lys Leu Glu Pro Leu Gly Ser Tyr
                915                 920                 925
Arg Ala Cys Val Ala Gly Phe Thr Asn Ile Thr Phe His Pro Gln Asn
                930                 935                 940
Lys Gly Leu Ile Asp Gly Ala Glu Ser Tyr Val Ser Phe Ser Arg Tyr
945                 950                 955                 960
Ser Asp Ala Val Ser Leu Pro Gln Asp Pro Gly Val Ile Cys Gly Ala
                965                 970                 975
Val Phe Gly Cys Ile Phe Gly Ala Leu Val Ile Val Thr Val Gly Gly
                980                 985                 990
```

Phe Ile Phe Trp Arg Lys Lys Arg Lys Asp Ala Lys Asn Asn Glu Val
            995                 1000                1005

Ser Phe Ser Gln Ile Lys Pro Lys Lys Ser Lys Leu Ile Arg Val
    1010                1015                1020

Glu Asn Phe Glu Ala Tyr Phe Lys Lys Gln Gln Ala Asp Ser Asn
    1025                1030                1035

Cys Gly Phe Ala Glu Glu Tyr Glu Asp Leu Lys Leu Val Gly Ile
    1040                1045                1050

Ser Gln Pro Lys Tyr Ala Ala Glu Leu Ala Glu Asn Arg Gly Lys
    1055                1060                1065

Asn Arg Tyr Asn Asn Val Leu Pro Tyr Asp Ile Ser Arg Val Lys
    1070                1075                1080

Leu Ser Val Gln Thr His Ser Thr Asp Asp Tyr Ile Asn Ala Asn
    1085                1090                1095

Tyr Met Pro Gly Tyr His Ser Lys Lys Asp Phe Ile Ala Thr Gln
    1100                1105                1110

Gly Pro Leu Pro Asn Thr Leu Lys Asp Phe Trp Arg Met Val Trp
    1115                1120                1125

Glu Lys Asn Val Tyr Ala Ile Ile Met Leu Thr Lys Cys Val Glu
    1130                1135                1140

Gln Gly Arg Thr Lys Cys Glu Glu Tyr Trp Pro Ser Lys Gln Ala
    1145                1150                1155

Gln Asp Tyr Gly Asp Ile Thr Val Ala Met Thr Ser Glu Ile Val
    1160                1165                1170

Leu Pro Glu Trp Thr Ile Arg Asp Phe Thr Val Lys Asn Ile Gln
    1175                1180                1185

Thr Ser Glu Ser His Pro Leu Arg Gln Phe His Phe Thr Ser Trp
    1190                1195                1200

Pro Asp His Gly Val Pro Asp Thr Thr Asp Leu Leu Ile Asn Phe
    1205                1210                1215

Arg Tyr Leu Val Arg Asp Tyr Met Lys Gln Ser Pro Pro Glu Ser
    1220                1225                1230

Pro Ile Leu Val His Cys Ser Ala Gly Val Gly Arg Thr Gly Thr
    1235                1240                1245

Phe Ile Ala Ile Asp Arg Leu Ile Tyr Gln Ile Glu Asn Glu Asn
    1250                1255                1260

Thr Val Asp Val Tyr Gly Ile Val Tyr Asp Leu Arg Met His Arg
    1265                1270                1275

Pro Leu Met Val Gln Thr Glu Asp Gln Tyr Val Phe Leu Asn Gln
    1280                1285                1290

Cys Val Leu Asp Ile Val Arg Ser Gln Lys Asp Ser Lys Val Asp
    1295                1300                1305

Leu Ile Tyr Gln Asn Thr Thr Ala Met Thr Ile Tyr Glu Asn Leu
    1310                1315                1320

Ala Pro Val Thr Thr Phe Gly Lys Thr Asn Gly Tyr Ile Ala
    1325                1330                1335

<210> SEQ ID NO 21
<211> LENGTH: 364
<212> TYPE: PRT
<213> ORGANISM: Homo sapiens

<400> SEQUENCE: 21

Met Pro Tyr Gln Tyr Pro Ala Leu Thr Pro Glu Gln Lys Lys Glu Leu

```
           1               5                  10                 15
        Ser Asp Ile Ala His Arg Ile Val Ala Pro Gly Lys Gly Ile Leu Ala
                       20                 25                 30

Ala Asp Glu Ser Thr Gly Ser Ile Ala Lys Arg Leu Gln Ser Ile Gly
                       35                 40                 45

Thr Glu Asn Thr Glu Glu Asn Arg Arg Phe Tyr Arg Gln Leu Leu Leu
                       50                 55                 60

Thr Ala Asp Asp Arg Val Asn Pro Cys Ile Gly Gly Val Ile Leu Phe
         65                 70                 75                 80

His Glu Thr Leu Tyr Gln Lys Ala Asp Asp Gly Arg Pro Phe Pro Gln
                       85                 90                 95

Val Ile Lys Ser Lys Gly Gly Val Val Gly Ile Lys Val Asp Lys Gly
                       100                105                110

Val Val Pro Leu Ala Gly Thr Asn Gly Glu Thr Thr Thr Gln Gly Leu
                       115                120                125

Asp Gly Leu Ser Glu Arg Cys Ala Gln Tyr Lys Lys Asp Gly Ala Asp
                       130                135                140

Phe Ala Lys Trp Arg Cys Val Leu Lys Ile Gly Glu His Thr Pro Ser
         145                150                155                160

Ala Leu Ala Ile Met Glu Asn Ala Asn Val Leu Ala Arg Tyr Ala Ser
                       165                170                175

Ile Cys Gln Gln Asn Gly Ile Val Pro Ile Val Glu Pro Glu Ile Leu
                       180                185                190

Pro Asp Gly Asp His Asp Leu Lys Arg Cys Gln Tyr Val Thr Glu Lys
                       195                200                205

Val Leu Ala Ala Val Tyr Lys Ala Leu Ser Asp His His Ile Tyr Leu
                       210                215                220

Glu Gly Thr Leu Leu Lys Pro Asn Met Val Thr Pro Gly His Ala Cys
         225                230                235                240

Thr Gln Lys Phe Ser His Glu Glu Ile Ala Met Ala Thr Val Thr Ala
                       245                250                255

Leu Arg Arg Thr Val Pro Pro Ala Val Thr Gly Ile Thr Phe Leu Ser
                       260                265                270

Gly Gly Gln Ser Glu Glu Glu Ala Ser Ile Asn Leu Asn Ala Ile Asn
                       275                280                285

Lys Cys Pro Leu Leu Lys Pro Trp Ala Leu Thr Phe Ser Tyr Gly Arg
                       290                295                300

Ala Leu Gln Ala Ser Ala Leu Lys Ala Trp Gly Gly Lys Lys Glu Asn
         305                310                315                320

Leu Lys Ala Ala Gln Glu Glu Tyr Val Lys Arg Ala Leu Ala Asn Ser
                       325                330                335

Leu Ala Cys Gln Gly Lys Tyr Thr Pro Ser Gly Gln Ala Gly Ala Ala
                       340                345                350

Ala Ser Glu Ser Leu Phe Val Ser Asn His Ala Tyr
                       355                360

<210> SEQ ID NO 22
<211> LENGTH: 175
<212> TYPE: PRT
<213> ORGANISM: Homo sapiens

<400> SEQUENCE: 22

Met Ser Ser Gln Ile Arg Gln Asn Tyr Ser Thr Asp Val Glu Ala Ala
 1               5                  10                 15
```

Val Asn Ser Leu Val Asn Leu Tyr Leu Gln Ala Ser Tyr Thr Tyr Leu
             20                  25                  30

Ser Leu Gly Phe Tyr Phe Asp Arg Asp Val Ala Leu Glu Gly Val
         35                  40                  45

Ser His Phe Phe Arg Glu Leu Ala Glu Glu Lys Arg Glu Gly Tyr Glu
 50                  55                  60

Arg Leu Leu Lys Met Gln Asn Gln Arg Gly Gly Arg Ala Leu Phe Gln
 65                  70                  75                  80

Asp Ile Lys Lys Pro Ala Glu Asp Glu Trp Gly Lys Thr Pro Asp Ala
                 85                  90                  95

Met Lys Ala Ala Met Ala Leu Glu Lys Lys Leu Asn Gln Ala Leu Leu
                100                 105                 110

Asp Leu His Ala Leu Gly Ser Ala Arg Thr Asp Pro His Leu Cys Asp
                115                 120                 125

Phe Leu Glu Thr His Phe Leu Asp Glu Glu Val Lys Leu Ile Lys Lys
130                 135                 140

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp
                165                 170                 175

<210> SEQ ID NO 23
<211> LENGTH: 202
<212> TYPE: PRT
<213> ORGANISM: Homo sapiens

<400> SEQUENCE: 23

Met Glu Leu Trp Gly Ala Tyr Leu Leu Leu Cys Leu Phe Ser Leu Leu
 1               5                  10                  15

Thr Gln Val Thr Thr Glu Pro Pro Thr Gln Lys Pro Lys Lys Ile Val
                 20                  25                  30

Asn Ala Lys Lys Asp Val Val Asn Thr Lys Met Phe Glu Glu Leu Lys
                 35                  40                  45

Ser Arg Leu Asp Thr Leu Ala Gln Glu Val Ala Leu Leu Lys Glu Gln
 50                  55                  60

Gln Ala Leu Gln Thr Val Cys Leu Lys Gly Thr Lys Val His Met Lys
 65                  70                  75                  80

Cys Phe Leu Ala Phe Thr Gln Thr Lys Thr Phe His Glu Ala Ser Glu
                 85                  90                  95

Asp Cys Ile Ser Arg Gly Gly Thr Leu Gly Thr Pro Gln Thr Gly Ser
                100                 105                 110

Glu Asn Asp Ala Leu Tyr Glu Tyr Leu Arg Gln Ser Val Gly Asn Glu
                115                 120                 125

Ala Glu Ile Trp Leu Gly Leu Asn Asp Met Ala Ala Glu Gly Thr Trp
                130                 135                 140

Val Asp Met Thr Gly Ala Arg Ile Ala Tyr Lys Asn Trp Glu Thr Glu
145                 150                 155                 160

Ile Thr Ala Gln Pro Asp Gly Gly Lys Thr Glu Asn Cys Ala Val Leu
                165                 170                 175

Ser Gly Ala Ala Asn Gly Lys Trp Phe Asp Lys Arg Cys Arg Asp Gln
                180                 185                 190

Leu Pro Tyr Ile Cys Gln Phe Gly Ile Val
                195                 200

<210> SEQ ID NO 24

```
<211> LENGTH: 428
<212> TYPE: PRT
<213> ORGANISM: Homo sapiens

<400> SEQUENCE: 24
```

| | | | | | | | | | | | | | | |
|---|---|---|---|---|---|---|---|---|---|---|---|---|---|---|
| Met | Gln | Glu | Leu | His | Leu | Leu | Trp | Trp | Ala | Leu | Leu | Leu | Gly | Leu | Ala |
| 1 | | | | 5 | | | | | 10 | | | | | 15 | |
| Gln | Ala | Cys | Pro | Glu | Pro | Cys | Asp | Cys | Gly | Glu | Lys | Tyr | Gly | Phe | Gln |
| | | | 20 | | | | | 25 | | | | | 30 | | |
| Ile | Ala | Asp | Cys | Ala | Tyr | Arg | Asp | Leu | Glu | Ser | Val | Pro | Pro | Gly | Phe |
| | | 35 | | | | | 40 | | | | | 45 | | | |
| Pro | Ala | Asn | Val | Thr | Thr | Leu | Ser | Leu | Ser | Ala | Asn | Arg | Leu | Pro | Gly |
| | 50 | | | | | 55 | | | | | 60 | | | | |
| Leu | Pro | Glu | Gly | Ala | Phe | Arg | Glu | Val | Pro | Leu | Leu | Gln | Ser | Leu | Trp |
| 65 | | | | | 70 | | | | | 75 | | | | | 80 |
| Leu | Ala | His | Asn | Glu | Ile | Arg | Thr | Val | Ala | Ala | Gly | Ala | Leu | Ala | Ser |
| | | | | 85 | | | | | 90 | | | | | 95 | |
| Leu | Ser | His | Leu | Lys | Ser | Leu | Asp | Leu | Ser | His | Asn | Leu | Ile | Ser | Asp |
| | | | 100 | | | | | 105 | | | | | 110 | | |
| Phe | Ala | Trp | Ser | Asp | Leu | His | Asn | Leu | Ser | Ala | Leu | Gln | Leu | Leu | Lys |
| | | 115 | | | | | 120 | | | | | 125 | | | |
| Met | Asp | Ser | Asn | Glu | Leu | Thr | Phe | Ile | Pro | Arg | Asp | Ala | Phe | Arg | Ser |
| | 130 | | | | | 135 | | | | | 140 | | | | |
| Leu | Arg | Ala | Leu | Arg | Ser | Leu | Gln | Leu | Asn | His | Asn | Arg | Leu | His | Thr |
| 145 | | | | | 150 | | | | | 155 | | | | | 160 |
| Leu | Ala | Glu | Gly | Thr | Phe | Thr | Pro | Leu | Thr | Ala | Leu | Ser | His | Leu | Gln |
| | | | | 165 | | | | | 170 | | | | | 175 | |
| Ile | Asn | Glu | Asn | Pro | Phe | Asp | Cys | Thr | Cys | Gly | Ile | Val | Trp | Leu | Lys |
| | | | 180 | | | | | 185 | | | | | 190 | | |
| Thr | Trp | Ala | Leu | Thr | Thr | Ala | Val | Ser | Ile | Pro | Glu | Gln | Asp | Asn | Ile |
| | | 195 | | | | | 200 | | | | | 205 | | | |
| Ala | Cys | Thr | Ser | Pro | His | Val | Leu | Lys | Gly | Thr | Pro | Leu | Ser | Arg | Leu |
| | 210 | | | | | 215 | | | | | 220 | | | | |
| Pro | Pro | Leu | Pro | Cys | Ser | Ala | Pro | Ser | Val | Gln | Leu | Ser | Tyr | Gln | Pro |
| 225 | | | | | 230 | | | | | 235 | | | | | 240 |
| Ser | Gln | Asp | Gly | Ala | Glu | Leu | Arg | Pro | Gly | Phe | Val | Leu | Ala | Leu | His |
| | | | | 245 | | | | | 250 | | | | | 255 | |
| Cys | Asp | Val | Asp | Gly | Gln | Pro | Ala | Pro | Gln | Leu | His | Trp | His | Ile | Gln |
| | | | 260 | | | | | 265 | | | | | 270 | | |
| Ile | Pro | Ser | Gly | Ile | Val | Glu | Ile | Thr | Ser | Pro | Asn | Val | Gly | Thr | Asp |
| | | 275 | | | | | 280 | | | | | 285 | | | |
| Gly | Arg | Ala | Leu | Pro | Gly | Thr | Pro | Val | Ala | Ser | Ser | Gln | Pro | Arg | Phe |
| | 290 | | | | | 295 | | | | | 300 | | | | |
| Gln | Ala | Phe | Ala | Asn | Gly | Ser | Leu | Leu | Ile | Pro | Asp | Phe | Gly | Lys | Leu |
| 305 | | | | | 310 | | | | | 315 | | | | | 320 |
| Glu | Glu | Gly | Thr | Tyr | Ser | Cys | Leu | Ala | Thr | Asn | Glu | Leu | Gly | Ser | Ala |
| | | | | 325 | | | | | 330 | | | | | 335 | |
| Glu | Ser | Ser | Val | Asp | Val | Ala | Leu | Ala | Thr | Pro | Gly | Glu | Gly | Gly | Glu |
| | | | 340 | | | | | 345 | | | | | 350 | | |
| Asp | Thr | Leu | Gly | Arg | Arg | Phe | His | Gly | Lys | Ala | Val | Glu | Gly | Lys | Gly |
| | | 355 | | | | | 360 | | | | | 365 | | | |
| Cys | Tyr | Thr | Val | Asp | Asn | Glu | Val | Gln | Pro | Ser | Gly | Pro | Glu | Asp | Asn |
| | 370 | | | | | 375 | | | | | 380 | | | | |
| Val | Val | Ile | Ile | Tyr | Leu | Ser | Arg | Ala | Gly | Asn | Pro | Glu | Ala | Ala | Val |

```
            385                 390                 395                 400
Ala Glu Gly Val Pro Gly Gln Leu Pro Pro Gly Leu Leu Leu Gly
                405                 410                 415

Gln Ser Leu Leu Leu Phe Phe Phe Leu Thr Ser Phe
            420                 425
```

<210> SEQ ID NO 25
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 25

```
Leu Gln Ser Leu Phe Asp Ser Pro Asp Phe Ser Lys
1               5                   10
```

<210> SEQ ID NO 26
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 26

```
Thr Gly Val Ile Thr Ser Pro Asp Phe Pro Asn Pro Tyr Pro Lys
1               5                   10                  15
```

<210> SEQ ID NO 27
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 27

```
Thr Ala Ser Asp Phe Ile Thr Lys
1               5
```

<210> SEQ ID NO 28
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 28

```
Ser Leu Glu Asp Leu Gln Leu Thr His Asn Lys
1               5                   10
```

<210> SEQ ID NO 29
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 29

```
Ile Asn Pro Ala Ser Leu Asp Lys
1               5
```

<210> SEQ ID NO 30
<211> LENGTH: 12
<212> TYPE: PRT
<213> ORGANISM: Artificial Sequence
<220> FEATURE:

```
<223> OTHER INFORMATION: Synthetic Polypeptide

<400> SEQUENCE: 30

Val Ile Thr Glu Pro Ile Pro Val Ser Asp Leu Arg
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 31

Glu Leu Trp Phe Ser Asp Asp Pro Asn Val Thr Lys
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 32

Tyr Val Ser Glu Leu His Leu Thr Arg
1               5

<210> SEQ ID NO 33
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 33

Leu Gly Gly Pro Glu Ala Gly Leu Gly Glu Tyr Leu Phe Glu Arg
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 34

Thr Val Leu Trp Pro Asn Gly Leu Ser Leu Asp Ile Pro Ala Gly Arg
1               5                   10                  15

<210> SEQ ID NO 35
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 35

Ala Val Gly Leu Ala Gly Thr Phe Arg
1               5

<210> SEQ ID NO 36
<211> LENGTH: 11
<212> TYPE: PRT
<213> ORGANISM: Artificial Sequence
<220> FEATURE:
<223> OTHER INFORMATION: Synthetic Polypeptide
```

<400> SEQUENCE: 36

Gln Ile Thr Val Asn Asp Leu Pro Val Gly Arg
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 37

Tyr Glu Val Thr Val Val Ser Val Arg
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 38

Ser Gly Tyr Leu Leu Pro Asp Thr Lys
1               5

<210> SEQ ID NO 39
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 39

Thr Trp Asn Asp Pro Ser Val Gln Gln Asp Ile Lys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 40

Leu Thr Leu Leu Ala Pro Leu Asn Ser Val Phe Lys
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 41

Ala Leu Gln Ala Ser Ala Leu Lys
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Polypeptide

```
<400> SEQUENCE: 42

Tyr Tyr Ile Ala Ala Ser Tyr Val Lys
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 43

Ala Thr Val Asn Pro Ser Ala Pro Arg
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 44

Val Glu Ile Phe Tyr Arg
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 45

Gly Phe Leu Leu Leu Ala Ser Leu Arg
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 46

Phe Leu Asn Val Leu Ser Pro Arg
1               5

<210> SEQ ID NO 47
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 47

Leu Asp Thr Leu Ala Gln Glu Val Ala Leu Leu Lys
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic Polypeptide
```

```
<400> SEQUENCE: 48

Ala Leu Pro Gly Thr Pro Val Ala Ser Ser Gln Pro Arg
1               5                   10
```